US008389219B2

(12) United States Patent
Anthony et al.

(10) Patent No.: US 8,389,219 B2
(45) Date of Patent: *Mar. 5, 2013

(54) DETECTION OF NUCLEIC ACIDS BY TYPE-SPECIFIC HYBRID CAPTURE METHOD

(75) Inventors: James Anthony, Frederick, MD (US); Attila Lorincz, North Potomac, MD (US); Inna Williams, Rockville, MD (US); John Troy, Fairfax, MD (US); Yanlin Tang, Rockville, MD (US)

(73) Assignee: Qiagen Gaithersburg, Inc., Gaithersburg, MD (US)

(*) Notice: Subject to any disclaimer, the term of this patent is extended or adjusted under 35 U.S.C. 154(b) by 288 days.

This patent is subject to a terminal disclaimer.

(21) Appl. No.: 12/622,160

(22) Filed: Nov. 19, 2009

(65) Prior Publication Data
US 2011/0003288 A1 Jan. 6, 2011

Related U.S. Application Data

(63) Continuation of application No. 10/311,645, filed as application No. PCT/US01/19353 on Jun. 15, 2001, which is a continuation-in-part of application No. 09/594,839, filed on Jun. 15, 2000, now Pat. No. 7,439,016.

(51) Int. Cl.
*C12Q 1/68* (2006.01)
*C07H 21/04* (2006.01)
(52) U.S. Cl. .................. 435/6.12; 536/24.31; 536/24.32
(58) Field of Classification Search ........................ None
See application file for complete search history.

(56) References Cited

U.S. PATENT DOCUMENTS

| | | | |
|---|---|---|---|
| 4,486,536 A | 12/1984 | Baker et al. | |
| 4,486,539 A | 12/1984 | Ranki et al. | |
| 4,563,417 A | 1/1986 | Albarella et al. | |
| 4,563,419 A | 1/1986 | Ranki et al. | |
| 4,689,294 A | 8/1987 | Boguslawski et al. | |
| 4,731,325 A | 3/1988 | Palva et al. | |
| 4,732,847 A | 3/1988 | Stuart et al. | |
| 4,743,535 A | 5/1988 | Carrico | |
| 4,751,177 A | 6/1988 | Stabinsky et al. | |
| 4,775,619 A | 10/1988 | Urdea | |
| 4,833,084 A | 5/1989 | Carrico | |
| 4,851,330 A | 7/1989 | Kohne et al. | |
| 4,865,980 A | 9/1989 | Stuart et al. | |
| 4,868,105 A | 9/1989 | Urdea et al. | |
| 4,889,798 A | 12/1989 | Rabbani | |
| 4,894,325 A | 1/1990 | Englehardt et al. | |
| 5,082,830 A | 1/1992 | Brakel et al. | |
| 5,106,727 A | 4/1992 | Hartley et al. | |
| 5,116,734 A | 5/1992 | Higgs et al. | |
| 5,200,313 A | 4/1993 | Carrico | |
| 5,283,175 A * | 2/1994 | Weaver et al. | 435/6.16 |
| 5,288,611 A | 2/1994 | Kohne et al. | |
| 5,374,524 A | 12/1994 | Miller et al. | |
| 5,424,413 A | 6/1995 | Hogan et al. | |
| 5,437,977 A | 8/1995 | Segev | |
| 5,474,895 A | 12/1995 | Ishii et al. | |
| 5,484,699 A | 1/1996 | Bouma et al. | |
| 5,545,806 A | 8/1996 | Lonberg et al. | |
| 5,545,807 A | 8/1996 | Surani et al. | |
| 5,556,748 A | 9/1996 | Douglas | |
| 5,614,362 A | 3/1997 | Urdea et al. | |
| 5,623,049 A | 4/1997 | Lobberding et al. | |
| 5,627,030 A | 5/1997 | Pandian et al. | |
| 5,629,153 A | 5/1997 | Urdea | |
| 5,629,156 A | 5/1997 | Shah et al. | |
| 5,635,352 A | 6/1997 | Urdea et al. | |
| 5,641,630 A | 6/1997 | Snitman | |
| 5,656,731 A | 8/1997 | Urdea | |
| 5,681,697 A | 10/1997 | Urdea et al. | |
| 5,681,897 A | 10/1997 | Silvis et al. | |
| 5,695,926 A | 12/1997 | Cros et al. | |
| 5,702,893 A | 12/1997 | Urdea et al. | |
| 5,728,531 A | 3/1998 | Yamada et al. | |
| 5,731,153 A | 3/1998 | Lucas et al. | |
| 5,736,316 A | 4/1998 | Irvine et al. | |
| 5,747,244 A | 5/1998 | Sheridan et al. | |
| 5,747,248 A | 5/1998 | Collins | |
| 5,750,338 A * | 5/1998 | Collins et al. | 435/6.12 |
| 5,759,773 A | 6/1998 | Tyagi et al. | |
| 5,786,183 A | 7/1998 | Ryder et al. | |
| 5,792,606 A | 8/1998 | Deger et al. | |
| 5,800,994 A | 9/1998 | Martinelli et al. | |
| 5,814,492 A | 9/1998 | Carrino et al. | |
| 5,821,339 A | 10/1998 | Schafer et al. | |
| 5,827,661 A | 10/1998 | Blais | |
| 5,853,993 A * | 12/1998 | Dellinger et al. | 435/6.14 |
| 5,888,724 A | 3/1999 | Silverstein et al. | |
| 5,981,179 A | 11/1999 | Lorinez et al. | |

(Continued)

FOREIGN PATENT DOCUMENTS

EP 0 163 220 12/1985
EP 0 167 366 B1 1/1986

(Continued)

OTHER PUBLICATIONS

International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6. (Note that the page number of this literature listed on the ISR is incorrect).
Vernick et al., "The HPV DNA virus hybrid capture assay: What is it- and where do we go from here?" MLO Med. Lab. Obs., (Mar. 2003), pp. 8-10, 13, vol. 35, No. 3.
Supplementary European Search Report of PCT/US2006/060603, dated Jul. 7, 2010 (8 pages).
Broker et al., "A Molecular Portrait of Human Papillomavirus Carcinogenesis", Cancer Cells, vol. 7, pp. 197-208, 1989 (Roche EU Opposition).

(Continued)

*Primary Examiner* — Prabha Chunduru
(74) *Attorney, Agent, or Firm* — Baker Donelson Bearman, Caldwell & Berkowitz, PC

(57) ABSTRACT

Target-specific hybrid capture (TSHC) provides a nucleic acid detection method that is not only rapid and sensitive, but also highly specific and capable of discriminating highly homologous nucleic acid sequences. The method produces DNA/RNA hybrids which can be detected by a variety of methods.

60 Claims, 10 Drawing Sheets

U.S. PATENT DOCUMENTS

| | | | |
|---|---|---|---|
| 5,994,079 | A | 11/1999 | De La Rosa et al. |
| 6,027,897 | A | 2/2000 | Lorincz et al. |
| 6,043,038 | A | 3/2000 | Sivaraja et al. |
| 6,057,099 | A | 5/2000 | Nathan et al. |
| 6,083,925 | A | 7/2000 | Li et al. |
| 6,110,676 | A | 8/2000 | Coull et al. |
| 6,110,682 | A | 8/2000 | Dellinger et al. |
| 6,110,687 | A | 8/2000 | Nilsen |
| 6,207,385 | B1 | 3/2001 | Stanley |
| 6,221,581 | B1 | 4/2001 | Engelhardt et al. |
| 6,225,053 | B1 | 5/2001 | Garcia et al. |
| 6,228,578 | B1 | 5/2001 | Impraim et al. |
| 6,228,580 | B1 | 5/2001 | Blumenfeld et al. |
| 6,232,462 | B1 | 5/2001 | Collins et al. |
| 6,268,128 | B1 | 7/2001 | Collins et al. |
| 6,277,579 | B1 | 8/2001 | Lazar et al. |
| 6,280,954 | B1 | 8/2001 | Ulfendahl |
| 6,326,136 | B1 | 12/2001 | Lazar et al. |
| 6,355,424 | B1 | 3/2002 | Lorincz et al. |
| 6,436,662 | B1 | 8/2002 | Mielzynska et al. |
| 6,521,190 | B1 | 2/2003 | Edens et al. |
| 6,544,732 | B1 | 4/2003 | Chee et al. |
| 6,583,278 | B1 | 6/2003 | Carter |
| 6,686,151 | B1 | 2/2004 | Lazar et al. |
| 6,828,098 | B2 | 12/2004 | Langmore et al. |
| 6,890,729 | B2 | 5/2005 | Mielzynska et al. |
| 6,969,585 | B2 | 11/2005 | Lorincz et al. |
| 6,977,148 | B2 | 12/2005 | Dean et al. |
| 7,001,776 | B2 | 2/2006 | Botacini das Dores et al. |
| 7,371,518 | B2 | 5/2008 | Lorincz et al. |
| 7,439,016 | B1 * | 10/2008 | Anthony et al. ............ 435/6.1 |
| 7,601,497 | B2 | 10/2009 | Nazarenko et al. |
| 7,645,571 | B2 * | 1/2010 | Anthony et al. ............ 435/6.12 |
| 7,812,144 | B2 | 10/2010 | Karlsen |
| 2001/0055766 | A1 | 12/2001 | Aristarkhov et al. |
| 2002/0012936 | A1 | 1/2002 | Lorincz et al. |
| 2003/0096232 | A1 | 5/2003 | Kris et al. |
| 2003/0108897 | A1 | 6/2003 | Drmanac |
| 2003/0175765 | A1 | 9/2003 | Kessler et al. |
| 2003/0175789 | A1 | 9/2003 | Weininger et al. |
| 2004/0180362 | A1 | 9/2004 | Lazar et al. |
| 2004/0214302 | A1 | 10/2004 | Anthony et al. |
| 2005/0032038 | A1 | 2/2005 | Fisher et al. |
| 2005/0032105 | A1 | 2/2005 | Bair et al. |
| 2005/0147996 | A1 | 7/2005 | Sorge |
| 2006/0051809 | A1 | 3/2006 | Nazarenko et al. |
| 2006/0160188 | A1 | 7/2006 | Kurnit et al. |
| 2006/0240449 | A1 | 10/2006 | McGlennen et al. |
| 2007/0154884 | A1 | 7/2007 | Lorincz |
| 2008/0200344 | A1 | 8/2008 | Cheng |
| 2008/0247914 | A1 | 10/2008 | Edens et al. |
| 2009/0032445 | A1 | 2/2009 | Doak et al. |
| 2009/0263819 | A1 | 10/2009 | Muraca |
| 2009/0286687 | A1 | 11/2009 | Dressman et al. |
| 2009/0298187 | A1 | 12/2009 | Nazarenko et al. |
| 2010/0081124 | A1 | 4/2010 | Abravaya et al. |
| 2010/0311039 | A1 | 12/2010 | Lowe et al. |

FOREIGN PATENT DOCUMENTS

| | | | |
|---|---|---|---|
| EP | 0 281 927 B1 | | 9/1988 |
| EP | 0 288 737 A1 | | 11/1988 |
| EP | 0333465 | | 9/1989 |
| EP | 0 336 454 B1 | | 11/1992 |
| EP | 0 144 914 A2 | | 6/1995 |
| EP | 0 415 978 B1 | | 3/1996 |
| EP | 0 703 296 A1 | | 3/1996 |
| EP | 1 806 410 A2 | | 7/2007 |
| EP | 2 184 368 A1 | | 5/2010 |
| JP | 2009 106220 | | 5/2009 |
| WO | 84/02721 | | 7/1984 |
| WO | 8607387 | | 12/1986 |
| WO | 88/03957 | | 6/1988 |
| WO | 91/08312 A1 | | 6/1991 |
| WO | 93/10263 A1 | | 5/1993 |
| WO | 95/17430 A1 | | 6/1995 |
| WO | 96/40992 | | 5/1996 |
| WO | 97/05277 | | 2/1997 |
| WO | 97/10364 | | 3/1997 |
| WO | 97/31256 A2 | | 8/1997 |
| WO | 98/18488 | | 5/1998 |
| WO | 98/22620 | | 5/1998 |
| WO | 98/59044 A1 | | 12/1998 |
| WO | 99/02488 | | 1/1999 |
| WO | 99/32654 A1 | | 7/1999 |
| WO | 99/36571 A2 | | 7/1999 |
| WO | 99/49224 | | 9/1999 |
| WO | 99/50459 A2 | | 10/1999 |
| WO | 00/60116 A1 | | 10/2000 |
| WO | 01/36681 | | 5/2001 |
| WO | 0196608 | | 12/2001 |
| WO | 2004/087950 | | 10/2004 |
| WO | 2005/080602 A2 | | 9/2005 |
| WO | 2007/056723 | | 5/2007 |
| WO | 2007/130519 A2 | | 11/2007 |
| WO | 2008/036061 | | 3/2008 |
| WO | 2008/139938 A1 | | 11/2008 |
| WO | 2009/057993 A1 | | 5/2009 |
| WO | 2009/123996 | | 10/2009 |
| WO | 2010/004251 A1 | | 1/2010 |
| WO | 2010/028382 | | 3/2010 |
| WO | 2010/127228 A1 | | 11/2010 |

OTHER PUBLICATIONS

Higgins et al., "Transcription Patterns of Human Papillomavirus Type 16 in Genital Intraepithelial Neoplasia: Evidence for Promoter Usage within the E7 Open Reading Frame during Epithelial Differentiation", Journal of General Virology, vol. 73, pp. 2047-2057, 1992 (Roche EU Opposition).

Karlsen et al., "Use of Multiple PCR Primer Sets for Optimal Detection of Human Papillomavirus", Journal of Clinical Microbiology, pp. 2095-2100, Sep. 1996 (Roche EU Opposition).

Park et al., "Physical Status and Expression of HPV Genes in Cervical Cancers", Gynecologic Oncology, vol. 65, pp. 121-129, 1997 (Roche EU Opposition).

Stoler et al., "Human Papillomavirus Type 16 and 18 Gene Expression in Cervical Neoplasias", Human Pathology, vol. 23, No. 2, pp. 117-128, Feb. 1992 (Roche EU Opposition).

De Villiers et al., "Classification of Papillomaviruses", Virology, vol. 324, pp. 17-27, 2004.

Howley et al., "A Rapid Method for Detecting and Mapping Homology between Heterologous DNAs", Journal of Biological Chemisny, vol. 254, No. 11, pp. 4879-4883, Jun. 10, 1979.

Law et al., "Conserved Polynucleotide Sequences Among the Genomics of Papillomaviruses", Journal of Virology, vol. 32, No. 1, pp. 199-207, Oct. 1979.

Heilman et al., "Cloning of Human Papilloma Virus Genomic DNAs and Analysis of Homologous Polynucleotide Sequences", Journal of Virology, vol. 36, No. 2, pp. 395-407, Nov. 1980.

Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.

Lorincz, A.T., "Molecular Methods for the Detection of Human Papillomavirus Infection", Obstetrics and Gynecology Clinics of North America, vol. 23, No. 3, pp. 707-730, Sep. 1996.

B.D. Hames, et al., "Nucleic Acid Hybridization. A Practical Approach." 1985.

Greg T. Hermanson, et al., "Immobilized Affinity Ligand Techniques." 1992.

Richard F. Taylor, "Protein Immobilization. Fundamentals and Applications." 1991.

Blair et al. "Herpes Simplex Virus Viron Stimulatory Protein mRNA Leader Contains Sequence Elements Which Increase Both Virus-Induced Transcription and tnRNA Stability," Journal of Virology, vol. 61, No. 8, pp. 2499-2508, Aug. 1987.

Brendan et al. "Related Functional Domains in Virus DNA Polymerases,"The EMBO Journal. vol. 6, No. 1, pp. 160-175, 1987.

Chandler et al., Detection of Dengue-2 Viral RNA by Reversible Target Capture Flybridization., J. Clin. Microbiol., vol. 31 (10), pp. 2641-2647, 1993.

Mazzulli et al, 1999, Multicenter Comparison of the Digene Hybrid Capture CMV DNA Assay (version 2.0) the pp65 Antignenemia Assay, and Cell Culture for Detection of Cytomegalovirus Viremia, J Clin. Microbiol., vol. 37, No. 4, pp. 958-963, 1999.

Murakami et al., Fluorescent-Labeled Oligonucleotide Probes: Detection of Hybrid Formation in Solution by Fluorscence Polarization Spectroscopy, Nucleic Acids Res., vol. 19 (15), pp. 4097-4102, 1991.

Dunn and Hassell: "A Novel Method to Map Transcripts: Evidence for Homology between an Adenovirus niRNA and Discrete Multiple Regions of the Viral Genome" Cell, 12:23-36, Sep. 1977.

Coutlee et al., "Nonisotopic Detection of RNA in an Enzyme Imunoassay using a Monoclonal Antibody Against DNA-RNA Hybrids" Analytical Biochemistry 181:153-162, 1989.

Chen et al., "DNA Optical Sensor: A Rapid Method for the Detection of DNA Hybridization" Biosensors & Bioelectronics 13:451-458, 1998.

Chevrier et al., "Isolation of a Specific DNA fragment and Development of a PCR Based Method for the Detection of *Mycobacterium genavense*" FEMS Immunology and Medical Microbiology 23:243-452, 1999.

Hakala et al., "Simultaneous Detection of Several Oligonucleotides by Time-Resolved Fluorometry: The Use of a Mixture of Categorized Microparticles in a Sandwich Type Mixed-Phase Hybridization Assay" Nucleic Acid Research, 26:5581-5588, 1998.

Gelmetti et al., "Detection of Rabbit Haemorrhagic Disease Virus (RHDV) by In Situ Hybridisation With a Digoxigenin Labelled RNA Probe" Journal of Virological Methods 72:219-226, 1998.

Radtkey et al., "Rapid, High Fidelity Analysis of Simple Sequence Repeats on an Electronically Active DNA Microchip" Nucleic Acids Research 28:i-vi, 2000.

Namimatsu et al., "Detection of *Salmonella* by Using the Colorimetric DNA/rRNA Sandwich Hybridization in Microtiter Wells" J. Vet. Med. Sci. 62:615-619, 2000.

Lazar et al., 1999 "Hybrid Capture®: a Sensitive Signal Amplification-based Chemiluminescent Test for the Detection and Quantitation of Human Viral and Bacterial Pathogens".1. Clin. Ligand Assay 22:139-151.

Newman et al., 1989 "Solution Hybridization and Enzyme Immunoassay for Biotinylated DNA:RNA Hybrids to Detect Enteroviral RNA in Cell Culture" MoL Cell Probes 3:375-382.

Lamoureux et al., 1997 "Detection of *Campylobacter jejuni* in Food and Poultry Viscera Using Immunomagnetic Separation and Microtitre Hybridization" J. Appl. Microbiol. 83:641-651.

Coutlee et al., 1990 "Quantitative Detection of Messenger RNA by Solution Hybridization and Enzyme Immunoassay" Biol. Chem. 265:11601-11604.

Stollar, B.D. and A. Rashtchian, 1987 "Immunochemical Approaches to Gene Probe Assays" Anal. Biochem. 161:387-394.

Blais, B.W., 1994 "Transcriptional Enhancement of the *Listeria monocytogenes* PCR and Simple Immunoenzymatic Assay of the Product Using Anti-RNA:DNA Antibodies" AppL Environ. Microbiol. 60:348-352.

Coutlee et al., 1991 "Detection of Transcripts of Human Papillomaviruses 16 and 18 in Cancer-derived Cell Lines and Cervical Biopsies by Enzyme Immunoassay for DNA-RNA Hybrids Following Solution Hybridization" J. Clin. Microbiol. 29:968-974.

Viscidi et al., 1989 "Monoclonal Antibody Solution Hybridization Assay for Detection of Human Immunodeficiency Virus Nucleic Acids" J. Clin. Microbiol. 27:120-125.

Boguslawski et al., 1986 "Characterization of Monoclonal Antibody to DNA:RNA and Its Application to Immunodetection of Hybrids" J. Immunol. Methods 89:123-130.

Coutlee et al., 1989 "Immunodetection of DNA with Biotinylated RNA Probes: A Study of Reactivity of a Monoclonal Antibody to DNA-RNA Hybrids" Anal. Biochem. 181:96-105.

Coutlee et al., 1991 "Immunodetection of DNA with Biotinylated RNA Probes: A Study of Reactivity of a Monoclonal Antibody to DNA-RNA Hybrids" Anal. Biochem. 198:217 (Published erratum).

Coutlee et al., 1989 "Comparison of Colorimetric Fluorescent, and Enzymatic Amplification Substrate Systems in an Enzyme Immunoassay for Detection of DNA-RNA Hybrids" J. Clin. Microbiol. 27:1002-1007.

Dalrymple et al., DNA sequence of the herpes simplex virus type 1 gene whose product is responsible for transcriptional activation of immediate early promoters, Nucleic Acids Research, 1985, vol. 13, No. 21, pp. 7865-7879.

McLauchlan et al., DNA sequence homology between two co-linear loci on the HSV genome which have different transforming abilities, The EMBO Journal, 1983, vol. 2, No. 11, pp. 1953-1961.

Goldsborough et al., Nucleotide Sequence of Human Papillomavirus Type 31: A Cervical Neoplasia Associated Virus, Virology, 1989, vol. 171, pp. 306-311.

McGeoch et al., "DNA Sequence and Genetic Content of the Hindlll 1 Region in the Short Unique Component of the Herpes Simplex Virus Type 2 Genome; Identification of the Gene Encoding Glycoprotein G, and Evolutionary Comparisons," J. Gen. Virol., 1987, vol. 68, pp. 19-38.

McGeoch et al., The Complete DNA Sequence of the Long Unique Region in the Genome of Herpes Simplex Virus Type I, 1 Gen Virol., 1988, vol. 69, pp. 1531-1574.

Yamada et al., Human Papillomavirus Type 16 Variant Lineages in United States Populations Characterized by Nucleotide Sequence Analysis of the E6, L2, and LI Coding Segments, J. Virol., Dec. 1995, vol. 69, No. 12, pp. 7743-7753.

Swain et al., Nucleotide Sequence of the Herpes Simplex Virus Type 2 Thymidine Kinase Gene,' Virol., Jun. 1983, vol. 46, No. 3, pp. 1045-1050.

Delius et al., Primer-Directed Sequencing of Human Papillomavirus Types, Current Topics in Microbiology and Immunology, 1994, vol. 185, pp. 13-31.

Blair et al., Herpes Simplex Virus Virion Stimulatory Protein mRNA Leader Contains Sequence Elements Which Increase Both Virus-Induced Transcription and mRNA Stability, J. Virol., Aug. 1987, vol. 62, No. 2, pp. 444-453.

Larder et al., Related functional domains in virus DNA polymerases, The EMBO J., 1987, vol. 6, No. 1, pp. 169-175.

McGeoch et al., Structures of Herpes Simplex Virus Type 1 Genes Required for Replication of Virus DNA, J. Virol., vol. 62, No. 2, pp. 444-453.

Zientara et al., 1998 "Use of reverse transcriptase-polymerase chain reaction (RT-PCR) and dot-blot hybridization for the detection and identification of African horse sickness virus nucleic acids" Arch Virol 14:317-327.

Mansy et al., 1999 "A PCR Based DNA Hybridisation Capture System for the Detection of Human Cytomegalovirus. A Comparative Study with Other Identification Methods" Journal of Virological Methods 80:113-122.

Poulsen et al., 1999 "Detection of Clinical Vancomycin-Resistant *Enterococci* in Denmark by Multiplex PCR and Sandwich Hybridization" APMIS 107:404-12.

Sjoroos et al., 1998 "Time-Resolved Fluorometry Based Sandwich Hybridisation Assay for HLA-DQA1 Typing" Disease Markers 14:9-19.

Edman et al., 2000 "Pathogen Analysis and Genetic Predisposition Testing Using Microelectronic Arrays and Isothermal Amplification" Journal of Investigative Medicine, 48:93-101.

Monteiro et al.,1997 Evaluation of Performances of Three DNA Enzyme Immunoassays for Detection of *Helicobacter pylori* PCR Products from Biopsy Specimens Journal of Clinical Microbiology, 35:2931-2936.

Chiu et al., 1998 "Sandwich-type Deoxyribonucleic Acid Hybridization Assays Based on Enzyme Amplified Time-Resolved Fluorometry" Analyst , 123:1315-1319.

White et al., 1999 "Signal Amplification System for DNA Hybridization Assays Based on in vitro Expression of a DNA Label Encoding Apoaequorin" Nucleic Acids Research 27:i-viii.

Hakala et al., 1998 "Detection of Oligonucleotide Hybridization on a Single Microparticle by Time-Resolved Fluorometry: Quantitation and Optimization of a Sandwich Type Assay" Bioconjugate Chem. 9:316-321.

Zammatteo et al., 1997 "Comparison between Microwell and Bead Supports for the Detection of Human *Cytomegalovirus* Amplicons by Sandwich Hybridization" Analytical Biochemistry 253:180-189.

Fisher et al., 1997 "A System for the Quantitation of DNA Using a Microtiter Plate-Based Hybridization and Enzyme Amplification Technology" Analytical Biochemistry 251:280-287.

Wicks et al., 1998 "A Sandwich Hybridization Assay Employing Enzyme Amplification for Determination of Specific Ribosomal RNA from Unpurified Cell Lysates" Analytical Biochemistry 259:258-264.

Bruckner-Lea et al., 2000 "Rotating Rod Renewable Microcolumns for Automated, Solid-Phase DNA Hybridization Studies" Anal. Chem. 72:4135-4141.

Allen et al., 1998 "High Resolution Genetic Typing of the Class II HLA-DRB 1 Locus Using Group-Specific Amplification and SSO-Hybridisation in Microplates" Hereditas 129:161-167.

Chomvarin et al., 2000 "Development of EIA for Detection of Chlamydia trachomatis in Genital Specimens" The Southeast Asian Journal of Tropical Medicine and Public Health, 31:96-103.

Alexandre et al., 1998 "Quantitative Determination of CMV DNA Using a Combination of Competitive PCR Amplification and Sandwich Hybridization" BioTechniques, 25: 676-683.

Casademont et al., 2000 "Rapid Detection of Campylobacter fetus by Polymerase Chain Reaction Combined With Non-Radioactive Hybridization Using an Oligonucleotide Covalently Bound to Microwells" Molecular and Cellular Probes 14:233-240.

Hara et al., "Small Sample Whole-Genome Amplification," Optics East 2005, UCRL-PROC-216415, Lawrence Livermore National Laboratory, Oct. 21, 2005.

Brigotti, et al., Nucleic Acids Res., vol. 26, No. 18, pp. 4306-4307, 1998.

International Search Report and Written Opinion of PCT/US2010/048714, dated Dec. 10, 2010 (14 pages).

International Preliminary Report on Patentability and Written Opinion of PCT/US2009/041033, dated Oct. 19, 2010 (6 pages).

International Search Report and Written Opinion of PCT/US2010/047769, dated Nov. 9, 2010 (11 pages).

Pachowics, et al., "Sequence specific large volume sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.

Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.

Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.

Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.

Nazarenko et al., "A novel method of HPV genotyping using Hybrid Capture sample preparation method combined with GP5+/6+ PCR and multiplex detection on Luminex XMAP," Journal of Virological Methods, Dec. 1, 2008, pp. 76-81, vol. 154, No. 1-2, Elsevier BV, XP025680302.

Taha et al., "Universal Collection Medium (UCM) is as suitable as the Standard Transport Medium (STM) for Hybrid Capture II (HC-2) assay," Journal of Virological Methods, May 1, 2006, pp. 32-35, vol. 36, No. 1, Elsevier BV, XP025178639.

Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.

Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.

Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.

Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.

Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.

Lowe et al., "HPV Genotype Detection Using Hybrid Capture Sample Preparation Combined with Whole Genome Amplification and Multiplex Detection with Luminex XMAP," Journal of Molecular Diagnostics; Nov. 6, 2010; pp. 847-853; vol. 12; No. 6; American Society for Investigative Pathology.

Partial European Search Report of EP10185824; mailed Feb. 16, 2011 (8 pages).

Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.

Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.

PCT/US2009/062041, International Searching Authority, Oct. 26, 2009 (5 pages).

U.S. Appl. No. 12/588,304, titled "Automated Assay and System," filed Oct. 9, 2009 (not yet published).

U.S. Appl. No. 12/588,306, titled "Open Platform Automated Sample Processing System," filed Oct. 9, 2009 (not yet published).

U.S. Appl. No. 12/622,131, titled "Multiple-Input Analytical System," filed Nov. 19, 2009 (not yet published).

U.S. Appl. No. 12/605,540, titled "Fast Results Hybrid Capture Assay and System," filed Oct. 26, 2009 (not yet published).

U.S. Appl. No. 12/605,605, titled "Fast Results Hybrid Capture Assay on an Automated Platform," filed Oct. 26, 2009 (not yet published).

Bhan et al., "2',5'-Linked oligo-3'-deoxyribonucleoside phosphorothioate chimeras: thermal stability and antisense inhibition of gene expression," Nucleic Acids Research, 1997, vol. 25, No. 16, pp. 3310-3317 (XP-002560367).

Genetech Diagnostics Pvt. Ltd., "Digene HBV Test Hybrid Capture II," Jun. 6, 2008 (XP-002560368).

Hantz et al., "Evaluation of accuracy of three assays for human papillomavirus detection and typing: Hybrid Capture 2, HPV Consensus kit and Amplicor HPV," Pathologie Biologie, Feb. 2008, vol. 56, No. 1, pp. 29-35 (XP002560369).

Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146 (XP002560370).

Boston Bioproducts Inc., "Protein Extraction buffers," Sep. 2, 2007 (XP002560371).

Bart "General Principles of Immunoprecipitation," Jul. 31, 2008 (XP002560372).

Mittendorf T, et al., "HPV-DNA-Diagnostik zur Zervixkarzinomfrüherkennung; Deutsche Agentur für HTA des Deutschen Instituts für Medizinische Dokumentation und Information," Aug. 1, 2007.

Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.

Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.

Malloy C, et al., "HPV DNA Testing: Technical and Programmatic Issues for Cervical Cancer Prevention in Low-Resource Settings," Path, Dec. 2000.

Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.

Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).

Bohm S, et al., "The Predominant mRNA Class in HPV16-Infected Genital Neoplasias does not Encode the E6 or the E7 Protein," Int. J. Cancer: 55, 791-798 (1993).

Middleton, K, et al., "Organization of Human Papillomavirus Productive Cycle during Neoplastic Progression Provides a Basis for Selection of Diagnostic markers," Journal of Virology, Oct. 2003, pp. 10186-10201.

Stoler, M, et al., "Human Papillomavirus Type 16 and 18 Gene Expression in Cervical Neoplasias," Human Pathol. 23 (1992), pp. 117-128.

Higgins, G, et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.

Karlsen, F, et al., "Use of Multiple PCR Primer Sets for Optimal Detection of Human Papillomavirus," J. Clin. Microbiol. 34 (1996), pp. 2095-2100.

Park, JS, et al., "Physical Status and Expression of HPV Genes in Cervical Cancers," Gynec. Oncol. 95 (1997), pp. 121-129.

Broker, TR, et al., "A Molecular Portrait of Human Papillomavirus Carcinogenesis," Cancer Cells 7 (1989), pp. 197-207.

Letter dated Jan. 6, 2010 to EPO re EP 1 038 022 (46 pages).

Letter to EPO dated Mar. 2, 2009 re EP 1 038 022 (15 pages).

Letter to EPO dated Oct. 6, 2008 re EP 1 038 022 (27 pages).

Letter to EPO dated Aug. 8, 2008 re EP 1 038 022 (11 pages).

EPO decision dated May 27, 2008 re Opposition of EP 1 038 022 (19 pages).

Letter to EPO dated Jan. 25, 2008 re EP 1 038 022 (10 pages).

Letter to EPO dated Jan. 23, 2008 re EP 1 038 022 (6 pages).

Communication from EPO dated May 14, 2007 re EP 1 038 022 (8 pages).

Letter to EPO dated Oct. 4, 2006 re EP 1 038 022 (11 pages).

Letter to EPO dated Apr. 18, 2006 re EP 1 038 022 (10 pages).

Partial International Search Report for PCT/US2009/062061, mail date Jan. 5, 2010.

Partial International Search Report for PCT/US2009/062041, mail date Jan. 5, 2010.

Thai et al., "An HPV 16, 18, and 45 genotyping test based on Hybrid Capture technology," Journal of Clinical Virology 45, S1 (2009) pp. 593-597.

Kitagawa et al., "Comparison of Poly(A) Poly(dT) and Poly(I) Poly(dC) as Immunogens for the Induction of Antibodies to RNA-DNA Hybrids," Molecular Immunology, vol. 19, No. 3, pp. 413-420, 1982.

Ishikawa et al., "Enzyme-Labeling of Antiboldies and Their Fragments for Enzyme Immunoassay and Immunohistochemical Staining," Journal of Immunoassay and Immunochemistry, 4: 3, 209-327.

Means et al., "Chemical Modifications of Proteins: History and Applications," Bioconjugate Chem. 1990, 1, 2-12.

Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.

Jakobovits et al., "Germ-line transmission and expression of a human-derived yeast artificial chromosome," pp. 255-258, Nature, vol. 362, Mar. 18, 1993.

International Search Report for PCT/US2009/041033, dated Dec. 22, 2009.

Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.

Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517.

GenBank Accession No. K02718, "Human papillomavirus type 16 (HPV16), complete genome.", Mar. 18, 1994. See http://www.ncbi.nlm.nihgov/nuccore/333031.

GenBank Accession No. X74479, "human papillomavirus type 45 genomic DNA.", Apr. 18, 2005. See http://www.ncbi.nlm.nih.gov/nuccore/397022.

GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.

GenBank Accession No. J04353, "Human papillomavirus type 31 (HPV-31), complete genome.", Mar. 18, 1994. See http://www.ncbi.nlm.nih.gov/nuccore/333048.

GenBank Accession No. M12732, "Human papillomavirus type 33, complete genome.", Mar. 21, 1994. See http://www.ncbi.nlm.nih.gov/nuccore/333049.

GenBank Accession No. M74117, "Human papillomavirus type 35, complete genome.", May 10, 2002. See http://www.ncbi.nlm.nih.gov/nuccore/333050.

GenBank Accession No. M62849, "Human papillomavirus ORFs.", Jan. 26, 2001. See http://www.ncbi.nlm.nih.gov/nuccore/333245.

GenBank Accession No. M62877, "Human papillomavirus type 51 genomic DNA, partial sequence.", Oct. 29, 1999. See http://www.ncbi.nlm.nih.gov/nuccore/333087.

GenBank Accession No. X74481, "Human papillomavirus type 52 genomic DNA.", Apr. 18, 2005. See http://www.ncbi.nlm.nih.gov/nuccore/397038.

GenBank Accession No. X74483, "Human papillomavirus type 56 genomic DNA.", Apr. 18, 2005. See http://www.ncbi.nlm.nih.gov/nuccore/397053.

GenBank Accession No. D90400, "Human papillomavirus type 58, complete genome.", Dec. 7, 2007. See http://www.ncbi.nlm.nih.gov/nuccore/222386.

GenBank Accession No. X77858, "Human papillomavirus type 59, complete viral genome.", Apr. 18, 2005. See http://www.ncbi.nlm.nih.gov/nuccore/555236.

GenBank Accession No. U31794, "Human papillomavirus type 66, complete genome.", Oct. 18, 1995. See http://www.ncbi.nlm.nih.gov/nuccore/1020290.

GenBank Accession No. X67161, "Human papillomavirus type L1 gene for major capsid protein.", Apr. 18, 2005. See http://www.ncbi.nlm.nih.gov/nuccore/1197494.

GenBank Accession No. AB027021, "Human papillomavirus type 82 DNA, complete genome.", Jun. 22, 2000. See http://www.ncbi.nlm.nih.gov/nuccore/6970427.

PCT/US2009/062061, International Searching Authority, Oct. 26, 2009 (6 pages).

International Search Report for PCT/US2009/062041, Patent Cooperation Treaty, Mar. 31, 2010 (17 pages).

International Search Report and Written Opinion of PCT/US2011/22887, dated Jun. 1, 2011.

International Preliminary Report on Patentability and Written Opinion of PCT/US2009/062061, dated May 12, 2011.

International Preliminary Report on Patentability and Written Opinion of PCT/US2009/062041, dated May 12, 2011.

GenBank Submission FJ429103. 2009 [Retrieved from the Internet May 20, 2011: <URL:http://www.ncbl.nlm.nih.gov/nuccore/FJ429103.1>]; in entirety.

International Search Report and Written Opinion of PCT/US2010/022264 dated Jun. 7, 2010 (19 pages).

Cohenford et al., "C-195. Rapid Detection of *Chlamydia trachomatis* from Specimens Collected from the ThinPrep Pap Test using Molecular Beacons and the Roche LightCycler," Abstracts of the General Meeting of the American Society for Microbiology, The Society, Washington, DC. (Jan. 1, 2001), p. 195, vol. 101, XP001098006.

Gentech Diagnostics: "Chlamydia DNA Test Kit," (Jun. 6, 2008), XP002578832, Retrieved from the Internet: URL: http://www.gentechin.com/chlamydiatestkit.htm.

Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.

Darwin et al., "Comparison of Digene Hybrid Capture 2 and Conventional Culture for Detection of *Chlamydia trachomatis* and *Neisseria gonorrhoeae* in Cervical Specimens," Journal of Clinical Microbiology, (Feb. 2002), pp. 641-644, vol. 40, No. 2, XP002578833.

Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.

Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.

International Search Report and Written Opinion based on PCT/US2001/037012 mailed Apr. 17, 2012.

Lowe et al; "A Hybrid-Capture Assay to Detect HPV MRNA Ratios in Cervical Specimens"; Journal of Virological Methods; vol. 179; No. 1; Jan. 2012; pp. 142-147.

International Search Report Based on Application No. PCT/US2012/026380 Mailed Oct. 15, 2012.

International Search Report Based on Application No. PCT/US2012/020684 Mailed Oct. 25, 2012.

Clad et al.; "Performance of the Aptima High-Risk Human Papillomavirus MRNA Assay in a Refferal Population in Comparison With Hybrid Capture 2 and Cytology", Journal of Clinical Microbiology; Mar. 2011; LNKD-PUBMED:21191046; vol. 49; No. 3; Dec. 29, 2010; pp. 1071-1076; Abstract.

Li et al; Detection of Human Papillomavirus Genotypes With Liquid Bead Microarray in Cervical Lesions of Northern Chinese Patients, Cancer Genetics and Cytogenetics, Elsevier Science Publishing, New York, NY, US; vol. 182; No. 1 Mar. 6, 2008; pp. 12-17; Abstract.

Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.

Han et al.; "Simultaneous Amplification and Identification of 25 Human Papillomavirus Types With Templex Technology"; Journal of Clinical Microbiology 200611 US LNKD-DOI:10.1128/JCM.01762-06; vol. 44; No. 11; Nov. 2006; pp. 4157-4162; Abstract.

Database EMBL [Online]; Jul. 19, 2007; "Sequence 25 From Patent EP1806410"; XP002675256;.Retrieved From EBI Accession No. EMBL:CS642417; Database Accession No. CS642417; The Whole Document.

Database EMBL [Online]; Dec. 14, 2010; "Sequence 26 From Patent US 7812144"; XP00267527;.Retrieved From EBI Accession No. EMBL:GX640151; Database Accession No. GX640151; The Whole Document.

Database Geneseq [Online]; Jan. 22, 2009; "HPV-16 E7/E6 Gene Target Sequence, Bases 752-774"; XP002675258, Retrieved From EBI Accesssion No. GSN:ATS82292; Database Accession No. ATS82292; The Whole Document.

Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.

Database Geneseq [Online]; Apr. 1, 2010; "HPV16 E7 Gene Forward RT-PCR Primer SEQ ID 49"; XP002675260; Retrieved From EBI Accession No. GSN:AXU96631; Database Accession No. AXU96631; The Whole Document.

Database Geneseq [Online]; Apr. 21, 2005; "E7 Coding Region (1-87) Amplifying Sense PCR Primer, SEQ ID No. 37"; XP002675261; Retrieved From EBI Accession No. GSN:ADX15568; Database Accession No. ADX15568; Sequence.

\* cited by examiner

TSHC-Plus Version 2

SEQUENCE LISTING

<160> NUMBER OF SEQ ID NOS: 162

<210> SEQ ID NO 1
<211> LENGTH: 42
<212> TYPE: DNA
<213> ORGANISM: Artificial Sequence
<220> FEATURE:
<223> OTHER INFORMATION: Nucleic acid probe

<400> SEQUENCE: 1
ttattattac gttcatgtcg gcaaacagct cgtttattat ta            42

<210> SEQ ID NO 2
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 2
ttattattac gtcctggatg gcgatacggc ttattatta            39

<210> SEQ ID NO 3
<211> LENGTH: 21
<212> TYPE: DNA
<213> ORGANISM: Artificial Sequence

```
<220> FEATURE:
<223> OTHER INFORMATION: Nucleic acid probe

<400> SEQUENCE: 3
cgtcctggat ggcgatacgg c                                    21

<210> SEQ ID NO 4
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 4
cgttcatgtc ggcaaacagc tcgt                                 24

<210> SEQ ID NO 5
<211> LENGTH: 45
<212> TYPE: DNA
<213> ORGANISM: Artificial Sequence
<220> FEATURE:
<223> OTHER INFORMATION: Nucleic acid probe

<400> SEQUENCE: 5
cgttcatgtc ggcaaacagc tcgtcgtcct ggatggcgat acggc          45

<210> SEQ ID NO 6
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 6
gatggggtta tttttcctaa gatggggcgg gtcc                      34

<210> SEQ ID NO 7
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 7
taccccgatc atcagttatc cttaaggt                             28

<210> SEQ ID NO 8
<211> LENGTH: 19
<212> TYPE: DNA
<213> ORGANISM: Artificial Sequence
<220> FEATURE:
<223> OTHER INFORMATION: Nucleic acid probe

<400> SEQUENCE: 8
aaaccgttcc atgaccgga                                       19

<210> SEQ ID NO 9
<211> LENGTH: 22
<212> TYPE: DNA
<213> ORGANISM: Artificial Sequence
<220> FEATURE:
<223> OTHER INFORMATION: Nucleic acid probe

<400> SEQUENCE: 9
atcgcgtgtt ccagagacag gc                                   22
```

```
<210> SEQ ID NO 10
<211> LENGTH: 17
<212> TYPE: DNA
<213> ORGANISM: Artificial Sequence
<220> FEATURE:
<223> OTHER INFORMATION: Nucleic acid probe

<400> SEQUENCE: 10
caacgcccaa aataata                                                  17

<210> SEQ ID NO 11
<211> LENGTH: 20
<212> TYPE: DNA
<213> ORGANISM: Artificial Sequence
<220> FEATURE:
<223> OTHER INFORMATION: Nucleic acid probe

<400> SEQUENCE: 11
gtccccgaac cgatctagcg                                               20

<210> SEQ ID NO 12
<211> LENGTH: 22
<212> TYPE: DNA
<213> ORGANISM: Artificial Sequence
<220> FEATURE:
<223> OTHER INFORMATION: Nucleic acid probe

<400> SEQUENCE: 12
cgaaccataa accattcccc at                                            22

<210> SEQ ID NO 13
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 13
cacgcccgtg gttctggaat tcgac                                         25

<210> SEQ ID NO 14
<211> LENGTH: 41
<212> TYPE: DNA
<213> ORGANISM: Artificial Sequence
<220> FEATURE:
<223> OTHER INFORMATION: Nucleic acid probe

<400> SEQUENCE: 14
tttattagat ggggttattt ttcctaagat ggggcgggtc c                       41

<210> SEQ ID NO 15
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 15
ggttattttt cctaag                                                   16

<210> SEQ ID NO 16
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 16
```

```
attattggtt atttttccta agattatt                                        28

<210> SEQ ID NO 17
<211> LENGTH: 40
<212> TYPE: DNA
<213> ORGANISM: Artificial Sequence
<220> FEATURE:
<223> OTHER INFORMATION: Nucleic acid probe

<400> SEQUENCE: 17
acgacgccct tgactccgat tcgtcatcgg atgactccct                           40

<210> SEQ ID NO 18
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 18
atgcgccagt gtatcaatca gctgtttcgg gt                                   32

<210> SEQ ID NO 19
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 19
caaaacgtcc tggagacggg tgagtgtcgg cgaggacg                             38

<210> SEQ ID NO 20
<211> LENGTH: 20
<212> TYPE: DNA
<213> ORGANISM: Artificial Sequence
<220> FEATURE:
<223> OTHER INFORMATION: Nucleic acid probe

<400> SEQUENCE: 20
gtccccgacc cgatctagcg                                                 20

<210> SEQ ID NO 21
<211> LENGTH: 23
<212> TYPE: DNA
<213> ORGANISM: Artificial Sequence
<220> FEATURE:
<223> OTHER INFORMATION: Nucleic acid probe

<400> SEQUENCE: 21
gcagactgcg ccaggaacga gta                                             23

<210> SEQ ID NO 22
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 22
gtgcccacgc ccgtggttct ggaattcgac agcga                                35

<210> SEQ ID NO 23
<211> LENGTH: 35
<212> TYPE: DNA
<213> ORGANISM: Artificial Sequence
```

```
<220> FEATURE:
<223> OTHER INFORMATION: Nucleic acid probe

<400> SEQUENCE: 23
gcagactgcg ccaggaacga gtagttggag tactg                         35

<210> SEQ ID NO 24
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 24
aagaggtcca ttgggtgggg ttgatacggg aaagac                        36

<210> SEQ ID NO 25
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 25
cgtaatgcgg cggtgcagac tcccctg                                  27

<210> SEQ ID NO 26
<211> LENGTH: 39
<212> TYPE: DNA
<213> ORGANISM: Artificial Sequence
<220> FEATURE:
<223> OTHER INFORMATION: Nucleic acid probe

<400> SEQUENCE: 26
ccaactaccc cgatcatcag ttatccttaa ggtctcttg                     39

<210> SEQ ID NO 27
<211> LENGTH: 47
<212> TYPE: DNA
<213> ORGANISM: Artificial Sequence
<220> FEATURE:
<223> OTHER INFORMATION: Nucleic acid probe

<400> SEQUENCE: 27
aaaaaaaaac aaaacgtcct ggagacgggt gagtgtcggc gaggacg            47

<210> SEQ ID NO 28
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 28
caaaacgtcc tggagacggg tgagtgtcgg cgaggacg                      38

<210> SEQ ID NO 29
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 29
caaaacgtcc ggagacgggt gagtgcggcg aggacg                        36
```

-continued

```
<210> SEQ ID NO 30
<211> LENGTH: 18
<212> TYPE: DNA
<213> ORGANISM: Artificial Sequence
<220> FEATURE:
<223> OTHER INFORMATION: Nucleic acid probe

<400> SEQUENCE: 30
aggaaaaata accccatc                                                 18

<210> SEQ ID NO 31
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 31
gacccgcccc atctt                                                    15

<210> SEQ ID NO 32
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 32
ggacccgccc catcttagga aaataaccc catc                                34

<210> SEQ ID NO 33
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 33
aaaaataacc cca                                                      13

<210> SEQ ID NO 34
<211> LENGTH: 11
<212> TYPE: DNA
<213> ORGANISM: Artificial Sequence
<220> FEATURE:
<223> OTHER INFORMATION: Nucleic acid probe

<400> SEQUENCE: 34
cgccccatct t                                                        11

<210> SEQ ID NO 35
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 35
ccatcttagg aaaaa                                                    15

<210> SEQ ID NO 36
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 36
```
ataactgatg atcgg                                           15

<210> SEQ ID NO 37
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 37
ccacccaatg gacctc                                          16

<210> SEQ ID NO 38
<211> LENGTH: 18
<212> TYPE: DNA
<213> ORGANISM: Artificial Sequence
<220> FEATURE:
<223> OTHER INFORMATION: Nucleic acid probe

<400> SEQUENCE: 38
gtctttcccg tatcaacc                                        18

<210> SEQ ID NO 39
<211> LENGTH: 12
<212> TYPE: DNA
<213> ORGANISM: Artificial Sequence
<220> FEATURE:
<223> OTHER INFORMATION: Nucleic acid probe

<400> SEQUENCE: 39
cgccgcatta cg                                              12

<210> SEQ ID NO 40
<211> LENGTH: 12
<212> TYPE: DNA
<213> ORGANISM: Artificial Sequence
<220> FEATURE:
<223> OTHER INFORMATION: Nucleic acid probe

<400> SEQUENCE: 40
aggggagtct gc                                              12

<210> SEQ ID NO 41
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 41
ctgtttgccg aca                                             13

<210> SEQ ID NO 42
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 42
tatcgccatc cag                                             13

<210> SEQ ID NO 43
<211> LENGTH: 14
<212> TYPE: DNA
<213> ORGANISM: Artificial Sequence

```
<220> FEATURE:
<223> OTHER INFORMATION: Nucleic acid probe

<400> SEQUENCE: 43
atgatcgggg tagt                                                      14

<210> SEQ ID NO 44
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 44
agagacctta aggata                                                    16

<210> SEQ ID NO 45
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 45
attccagaac cacgg                                                     15

<210> SEQ ID NO 46
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 46
ttccagaacc acg                                                       13

<210> SEQ ID NO 47
<211> LENGTH: 11
<212> TYPE: DNA
<213> ORGANISM: Artificial Sequence
<220> FEATURE:
<223> OTHER INFORMATION: Nucleic acid probe

<400> SEQUENCE: 47
tccagaacca c                                                         11

<210> SEQ ID NO 48
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 48
gttcctggcg cag                                                       13

<210> SEQ ID NO 49
<211> LENGTH: 12
<212> TYPE: DNA
<213> ORGANISM: Artificial Sequence
<220> FEATURE:
<223> OTHER INFORMATION: Nucleic acid probe

<400> SEQUENCE: 49
ttcctggcgc ag                                                        12
```

<210> SEQ ID NO 50
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 50
gcccgcgccg ccagcactac tttc                                              24

<210> SEQ ID NO 51
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 51
aaacgttggg aggtgtgtgc gtcatcctgg agcta                                  35

<210> SEQ ID NO 52
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 52
gccaaaaccg agtgaggttc tgtgt                                             25

<210> SEQ ID NO 53
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 53
aaacgttggg aggtgtgtgc gtca                                              24

<210> SEQ ID NO 54
<211> LENGTH: 23
<212> TYPE: DNA
<213> ORGANISM: Artificial Sequence
<220> FEATURE:
<223> OTHER INFORMATION: Nucleic acid probe

<400> SEQUENCE: 54
tgctcgtcac gaagtcactc atg                                               23

<210> SEQ ID NO 55
<211> LENGTH: 21
<212> TYPE: DNA
<213> ORGANISM: Artificial Sequence
<220> FEATURE:
<223> OTHER INFORMATION: Nucleic acid probe

<400> SEQUENCE: 55
cattactgcc cgcaccggac c                                                 21

<210> SEQ ID NO 56
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 56

```
gccgtggtgt tcctgaacac cagg                                              24

<210> SEQ ID NO 57
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 57
agtcagggtt gcccgacttc gtcac                                             25

<210> SEQ ID NO 58
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 58
caggcgtcct cggtctcggg cggggc                                            26

<210> SEQ ID NO 59
<211> LENGTH: 20
<212> TYPE: DNA
<213> ORGANISM: Artificial Sequence
<220> FEATURE:
<223> OTHER INFORMATION: Nucleic acid probe

<400> SEQUENCE: 59
cccacgtcac cgggggcccc                                                   20

<210> SEQ ID NO 60
<211> LENGTH: 25
<212> TYPE: DNA
<213> ORGANISM: Artificial Sequence
<220> FEATURE:
<223> OTHER INFORMATION: Nucleic acid probe

<400> SEQUENCE: 60
gccggtcgcg tgcgacgccc aaggc                                             25

<210> SEQ ID NO 61
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 61
ccgacgcgtg ggtatctagg gggtcg                                            26

<210> SEQ ID NO 62
<211> LENGTH: 26
<212> TYPE: DNA
<213> ORGANISM: Artificial Sequence
<220> FEATURE:
<223> OTHER INFORMATION: Nucleic acid probe

<400> SEQUENCE: 62
cgggacggcg agcggaaagt caacgt                                            26

<210> SEQ ID NO 63
<211> LENGTH: 9
<212> TYPE: DNA
<213> ORGANISM: Artificial Sequence
```

```
<220> FEATURE:
<223> OTHER INFORMATION: Nucleic acid probe

<400> SEQUENCE: 63 ggcgcgggc                                                                    9

<210> SEQ ID NO 64
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 64
gaaagtagtg ctggc                                                            15

<210> SEQ ID NO 65
<211> LENGTH: 11
<212> TYPE: DNA
<213> ORGANISM: Artificial Sequence
<220> FEATURE:
<223> OTHER INFORMATION: Nucleic acid probe

<400> SEQUENCE: 65
tgctggcggc g                                                                11

<210> SEQ ID NO 66
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 66
acacctccca acg                                                              13

<210> SEQ ID NO 67
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 67
ctccaggatg acg                                                              13

<210> SEQ ID NO 68
<211> LENGTH: 12
<212> TYPE: DNA
<213> ORGANISM: Artificial Sequence
<220> FEATURE:
<223> OTHER INFORMATION: Nucleic acid probe

<400> SEQUENCE: 68
tcggttttgg tc                                                               12

<210> SEQ ID NO 69
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 69
acacagaacc tca                                                              13
```

```
<210> SEQ ID NO 70
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 70
cacacacctc cca                                                         13

<210> SEQ ID NO 71
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 71
cgacccccta gata                                                        14

<210> SEQ ID NO 72
<211> LENGTH: 11
<212> TYPE: DNA
<213> ORGANISM: Artificial Sequence
<220> FEATURE:
<223> OTHER INFORMATION: Nucleic acid probe

<400> SEQUENCE: 72
ccacgcgtcg g                                                           11

<210> SEQ ID NO 73
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 73
acgttgactt tccgc                                                       15

<210> SEQ ID NO 74
<211> LENGTH: 10
<212> TYPE: DNA
<213> ORGANISM: Artificial Sequence
<220> FEATURE:
<223> OTHER INFORMATION: Nucleic acid probe

<400> SEQUENCE: 74
cgccgtcccg                                                             10

<210> SEQ ID NO 75
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 75
gtacagatgg taccggggtt gtagaagtat ctg                                   33

<210> SEQ ID NO 76
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 76
```
ctgcaacaag acatacatcg accggtccac c                                      31

<210> SEQ ID NO 77
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 77
gaagtaggtg aggctgcatg tgaagtggta g                                      31

<210> SEQ ID NO 78
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 78
cagctctgtg cataactgtg gtaactttct ggg                                    33

<210> SEQ ID NO 79
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 79
gaggtcttct ccaacatgct atgcaacgtc ctg                                    33

<210> SEQ ID NO 80
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 80
gtgtaggtgc atgctctata ggtacatcag gcc                                    33

<210> SEQ ID NO 81
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 81
caatgccgag cttagttcat gcaatttccg agg                                    33

<210> SEQ ID NO 82
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 82
gaagtagtag ttgcagacgc ccctaaaggt tgc                                    33

<210> SEQ ID NO 83
<211> LENGTH: 30
<212> TYPE: DNA
<213> ORGANISM: Artificial Sequence

```
<220> FEATURE:
<223> OTHER INFORMATION: Nucleic acid probe

<400> SEQUENCE: 83
gaacgcgatg gtacaggcac tgcagggtcc                                    30

<210> SEQ ID NO 84
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 84
gaacgcgatg gtacaggcac tgca                                          24

<210> SEQ ID NO 85
<211> LENGTH: 24
<212> TYPE: DNA
<213> ORGANISM: Artificial Sequence
<220> FEATURE:
<223> OTHER INFORMATION: Nucleic acid probe

<400> SEQUENCE: 85
acgcccaccc aatggaatgt accc                                          24

<210> SEQ ID NO 86
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 86
tctgcgtcgt tggagtcgtt cctgtcgtgc tc                                 32

<210> SEQ ID NO 87
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 87
ttattattac tacatacatt gccgccatgt tcgcca                             36

<210> SEQ ID NO 88
<211> LENGTH: 46
<212> TYPE: DNA
<213> ORGANISM: Artificial Sequence
<220> FEATURE:
<223> OTHER INFORMATION: Nucleic acid probe

<400> SEQUENCE: 88
ttattattat gttgccctct gtgccccgt tgtctatagc ctccgt                   46

<210> SEQ ID NO 89
<211> LENGTH: 38
<212> TYPE: DNA
<213> ORGANISM: Artificial Sequence
<220> FEATURE:
<223> OTHER INFORMATION: Nucleic acid probe

<400> SEQUENCE: 89
ttattattag gagcagtgcc caaaagatta aagtttgc                           38
```

```
<210> SEQ ID NO 90
<211> LENGTH: 37
<212> TYPE: DNA
<213> ORGANISM: Artificial Sequence
<220> FEATURE:
<223> OTHER INFORMATION: Nucleic acid probe

<400> SEQUENCE: 90
ttattattac acggtgctgg aatacggtga gggggtg                                37

<210> SEQ ID NO 91
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 91
ttattattaa cgcccaccca atggaatgta ccc                                    33

<210> SEQ ID NO 92
<211> LENGTH: 35
<212> TYPE: DNA
<213> ORGANISM: Artificial Sequence
<220> FEATURE:
<223> OTHER INFORMATION: Nucleic acid probe

<400> SEQUENCE: 92
ttattattaa tagtattgtg gtgtgtttct cacat                                  35

<210> SEQ ID NO 93
<211> LENGTH: 30
<212> TYPE: DNA
<213> ORGANISM: Artificial Sequence
<220> FEATURE:
<223> OTHER INFORMATION: Nucleic acid probe

<400> SEQUENCE: 93
ttattattag ttggagtcgt tcctgtcgtg                                        30

<210> SEQ ID NO 94
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 94
ttattattac ggaatttcat tttggggctc t                                      31

<210> SEQ ID NO 95
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 95
gctcgaaggt cgtctgctga gctttctact act                                    33

<210> SEQ ID NO 96
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 96
```

```
gcgccatcct gtaatgcact tttccacaaa gc                               32

<210> SEQ ID NO 97
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 97
tagtgctagg tgtagtggac gcaggaggtg g                                31

<210> SEQ ID NO 98
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 98
ggtcacaaca tgtattacac tgccctcggt ac                               32

<210> SEQ ID NO 99
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 99
cctacgtctg cgaagtcttt cttgccgtgc c                                31

<210> SEQ ID NO 100
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 100
ctgcattgtc actactatcc ccaccactac tttg                             34

<210> SEQ ID NO 101
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 101
ccacaaggca cattcataca tacacgcacg ca                               32

<210> SEQ ID NO 102
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 102
gttctaaggt cctctgccga gctctctact gta                              33

<210> SEQ ID NO 103
<211> LENGTH: 36
<212> TYPE: DNA
<213> ORGANISM: Artificial Sequence
```

```
<220> FEATURE:
<223> OTHER INFORMATION: Nucleic acid probe

<400> SEQUENCE: 103
ttattattat gcggttttgg gggtcgacgt ggaggc                              36

<210> SEQ ID NO 104
<211> LENGTH: 36
<212> TYPE: DNA
<213> ORGANISM: Artificial Sequence
<220> FEATURE:
<223> OTHER INFORMATION: Nucleic acid probe

<400> SEQUENCE: 104
ttattattaa gacctgcccc ctaagggtac atagcc                              36

<210> SEQ ID NO 105
<211> LENGTH: 49
<212> TYPE: DNA
<213> ORGANISM: Artificial Sequence
<220> FEATURE:
<223> OTHER INFORMATION: Nucleic acid probe

<400> SEQUENCE: 105
ttattattac agcattgcag cctttttgtt acttgcttgt aatagctcc                49

<210> SEQ ID NO 106
<211> LENGTH: 34
<212> TYPE: DNA
<213> ORGANISM: Artificial Sequence
<220> FEATURE:
<223> OTHER INFORMATION: Nucleic acid probe

<400> SEQUENCE: 106
ttattattaa tcctgtaatg cacttttcca caaa                                34

<210> SEQ ID NO 107
<211> LENGTH: 31
<212> TYPE: DNA
<213> ORGANISM: Artificial Sequence
<220> FEATURE:
<223> OTHER INFORMATION: Nucleic acid probe

<400> SEQUENCE: 107
ttattattag cctggtcaca acatgtatta c                                   31

<210> SEQ ID NO 108
<211> LENGTH: 33
<212> TYPE: DNA
<213> ORGANISM: Artificial Sequence
<220> FEATURE:
<223> OTHER INFORMATION: Nucleic acid probe

<400> SEQUENCE: 108
ttattattac aggatctaat tcattctgag gtt                                 33

<210> SEQ ID NO 109
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 109
tgcggttttg gggtcgacg tggaggc                                         27
```

```
<210> SEQ ID NO 110
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 110
gcctccacgt cgac                                                       14

<210> SEQ ID NO 111
<211> LENGTH: 11
<212> TYPE: DNA
<213> ORGANISM: Artificial Sequence
<220> FEATURE:
<223> OTHER INFORMATION: Nucleic acid probe

<400> SEQUENCE: 111
ccccaaaacc g                                                          11

<210> SEQ ID NO 112
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 112
ggtacattcc attggg                                                     16

<210> SEQ ID NO 113
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 113
tgggcgttaa taataa                                                     16

<210> SEQ ID NO 114
<211> LENGTH: 12
<212> TYPE: DNA
<213> ORGANISM: Artificial Sequence
<220> FEATURE:
<223> OTHER INFORMATION: Nucleic acid probe

<400> SEQUENCE: 114
accatcgcgt tc                                                         12

<210> SEQ ID NO 115
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 115
ggaccctgca gtgc                                                       14

<210> SEQ ID NO 116
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 116
```
ctgtaccatc gcgtt                                          15

<210> SEQ ID NO 117
<211> LENGTH: 12
<212> TYPE: DNA
<213> ORGANISM: Artificial Sequence
<220> FEATURE:
<223> OTHER INFORMATION: Nucleic acid probe

<400> SEQUENCE: 117
tgcagtgcct gt                                             12

<210> SEQ ID NO 118
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 118
ccacctcctg cgt                                            13

<210> SEQ ID NO 119
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 119
attacaggat ggcgc                                          15

<210> SEQ ID NO 120
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 120
gctttctgga aaagtg                                         16

<210> SEQ ID NO 121
<211> LENGTH: 18
<212> TYPE: DNA
<213> ORGANISM: Artificial Sequence
<220> FEATURE:
<223> OTHER INFORMATION: Nucleic acid probe

<400> SEQUENCE: 121
ccactacacc tagcacta                                       18

<210> SEQ ID NO 122
<211> LENGTH: 17
<212> TYPE: DNA
<213> ORGANISM: Artificial Sequence
<220> FEATURE:
<223> OTHER INFORMATION: Nucleic acid probe

<400> SEQUENCE: 122
cagatacttc tacaacc                                        17

<210> SEQ ID NO 123
<211> LENGTH: 16
<212> TYPE: DNA
<213> ORGANISM: Artificial Sequence

```
<220> FEATURE:
<223> OTHER INFORMATION: Nucleic acid probe

<400> SEQUENCE: 123
ccggtaccat ctgtac                                                   16

<210> SEQ ID NO 124
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 124
ggtggaccgg tcg                                                      13

<210> SEQ ID NO 125
<211> LENGTH: 18
<212> TYPE: DNA
<213> ORGANISM: Artificial Sequence
<220> FEATURE:
<223> OTHER INFORMATION: Nucleic acid probe

<400> SEQUENCE: 125
atgtatgtct tgttgcag                                                 18

<210> SEQ ID NO 126
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 126
ctaccacttc acatgc                                                   16

<210> SEQ ID NO 127
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 127
agcctcacct acttc                                                    15

<210> SEQ ID NO 128
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 128
cccagaaagt taccac                                                   16

<210> SEQ ID NO 129
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 129
agttatgcac agagct                                                   16
```

```
<210> SEQ ID NO 130
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 130
caggacgttg catagc                                                     16

<210> SEQ ID NO 131
<211> LENGTH: 17
<212> TYPE: DNA
<213> ORGANISM: Artificial Sequence
<220> FEATURE:
<223> OTHER INFORMATION: Nucleic acid probe

<400> SEQUENCE: 131
atgttggaga agacctc                                                    17

<210> SEQ ID NO 132
<211> LENGTH: 17
<212> TYPE: DNA
<213> ORGANISM: Artificial Sequence
<220> FEATURE:
<223> OTHER INFORMATION: Nucleic acid probe

<400> SEQUENCE: 132
ggcctgatgt acctata                                                    17

<210> SEQ ID NO 133
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 133
gagcatgcac ctacac                                                     16

<210> SEQ ID NO 134
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 134
ctcggaaatt gcatg                                                      15

<210> SEQ ID NO 135
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 135
aactaagctc ggcatt                                                     16

<210> SEQ ID NO 136
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 136
```

```
gcaaccttta gggg                                                14
```

<210> SEQ ID NO 137
<211> LENGTH: 19
<212> TYPE: DNA
<213> ORGANISM: Artificial Sequence
<220> FEATURE:
<223> OTHER INFORMATION: Nucleic acid probe

<400> SEQUENCE: 137

```
cgtctgcaac tactacttc                                           19
```

<210> SEQ ID NO 138
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 138

```
gtaccgaggg cagt                                                14
```

<210> SEQ ID NO 139
<211> LENGTH: 18
<212> TYPE: DNA
<213> ORGANISM: Artificial Sequence
<220> FEATURE:
<223> OTHER INFORMATION: Nucleic acid probe

<400> SEQUENCE: 139

```
gtaatacatg ttgtgacc                                            18
```

<210> SEQ ID NO 140
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 140

```
ggcacggcaa gaaa                                                14
```

<210> SEQ ID NO 141
<211> LENGTH: 17
<212> TYPE: DNA
<213> ORGANISM: Artificial Sequence
<220> FEATURE:
<223> OTHER INFORMATION: Nucleic acid probe

<400> SEQUENCE: 141

```
gacttcgcag acgtagg                                             17
```

<210> SEQ ID NO 142
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 142

```
caaagtagtg gtggg                                               15
```

<210> SEQ ID NO 143
<211> LENGTH: 19
<212> TYPE: DNA
<213> ORGANISM: Artificial Sequence

```
<220> FEATURE:
<223> OTHER INFORMATION: Nucleic acid probe

<400> SEQUENCE: 143
gatagtagtg acaatgcag                                                19

<210> SEQ ID NO 144
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 144
tgcgtgcgtg tatgta                                                   16

<210> SEQ ID NO 145
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 145
tgaatgtgcc ttgtgg                                                   16

<210> SEQ ID NO 146
<211> LENGTH: 18
<212> TYPE: DNA
<213> ORGANISM: Artificial Sequence
<220> FEATURE:
<223> OTHER INFORMATION: Nucleic acid probe

<400> SEQUENCE: 146
agtagtagaa agctcagc                                                 18

<210> SEQ ID NO 147
<211> LENGTH: 15
<212> TYPE: DNA
<213> ORGANISM: Artificial Sequence
<220> FEATURE:
<223> OTHER INFORMATION: Nucleic acid probe

<400> SEQUENCE: 147
agacgacctt cgagc                                                    15

<210> SEQ ID NO 148
<211> LENGTH: 17
<212> TYPE: DNA
<213> ORGANISM: Artificial Sequence
<220> FEATURE:
<223> OTHER INFORMATION: Nucleic acid probe

<400> SEQUENCE: 148
tacagtagag agctcgg                                                  17

<210> SEQ ID NO 149
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 149
cagaggacct tagaac                                                   16
```

```
<210> SEQ ID NO 150
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 150
gagcacgaca ggaacg                                              16

<210> SEQ ID NO 151
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 151
actccaacga cgcaga                                              16

<210> SEQ ID NO 152
<211> LENGTH: 28
<212> TYPE: DNA
<213> ORGANISM: Artificial Sequence
<220> FEATURE:
<223> OTHER INFORMATION: Nucleic acid probe

<400> SEQUENCE: 152
gctggatgtg tctgcggcgt tttatcat                                 28

<210> SEQ ID NO 153
<211> LENGTH: 27
<212> TYPE: DNA
<213> ORGANISM: Artificial Sequence
<220> FEATURE:
<223> OTHER INFORMATION: Nucleic acid probe

<400> SEQUENCE: 153
actgttcaag cctccaagct gcgcctt                                  27

<210> SEQ ID NO 154
<211> LENGTH: 32
<212> TYPE: DNA
<213> ORGANISM: Artificial Sequence
<220> FEATURE:
<223> OTHER INFORMATION: Nucleic acid probe

<400> SEQUENCE: 154
atgataaaac gccgcagaca catccagcga ta                            32

<210> SEQ ID NO 155
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 155
atgataaaac gccg                                                14

<210> SEQ ID NO 156
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 156
```

```
cagacacatc cagc                                                          14

<210> SEQ ID NO 157
<211> LENGTH: 13
<212> TYPE: DNA
<213> ORGANISM: Artificial Sequence
<220> FEATURE:
<223> OTHER INFORMATION: Nucleic acid probe

<400> SEQUENCE: 157
aaggcacagc ttg                                                           13

<210> SEQ ID NO 158
<211> LENGTH: 14
<212> TYPE: DNA
<213> ORGANISM: Artificial Sequence
<220> FEATURE:
<223> OTHER INFORMATION: Nucleic acid probe

<400> SEQUENCE: 158
gaggcttgaa cagt                                                          14

<210> SEQ ID NO 159
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 159
tatcgctgga tgtgtc                                                        16

<210> SEQ ID NO 160
<211> LENGTH: 16
<212> TYPE: DNA
<213> ORGANISM: Artificial Sequence
<220> FEATURE:
<223> OTHER INFORMATION: Nucleic acid probe

<400> SEQUENCE: 160
tcggcgtttt atcatg                                                        16

<210> SEQ ID NO 161
<211> LENGTH: 21
<212> TYPE: DNA
<213> ORGANISM: Artificial Sequence
<220> FEATURE:
<223> OTHER INFORMATION: Synthetic Primer
<300> PUBLICATION INFORMATION:
<301> AUTHORS: Kleas, et al.
<303> JOURNAL: Molecular Medicine
<304> VOLUME: 77
<306> PAGES: 299-302
<307> DATE: 1999

<400> SEQUENCE: 161
aagacccagg tccagatgaa g                                                  21

<210> SEQ ID NO 162
<211> LENGTH: 20
<212> TYPE: DNA
<213> ORGANISM: Artificial Sequence
<220> FEATURE:
<223> OTHER INFORMATION: Synthetic primer
<300> PUBLICATION INFORMATION:
<301> AUTHORS: Kleas, et al.
<303> JOURNAL: Molecular Medicine
<304> VOLUME: 77
```

```
<306> PAGES: 299-302
<307> DATE: 1999

<400> SEQUENCE: 162
agaatgcaag aagcccagac                                              20
```

DETECTION OF NUCLEIC ACIDS BY TYPE-SPECIFIC HYBRID CAPTURE METHOD

CROSS REFERENCE TO RELATED APPLICATIONS

This is a continuation of U.S. application Ser. No. 10/311,645, filed Apr. 4, 2003, which is a §371 National Stage of PCT/US01/19353, filed on Jun. 15, 2001, which is a continuation-in-part of U.S. application Ser No. 09/594,839, filed Jun. 15, 2000, the contents of each which are incorporated herein by reference in their entireties.

FIELD OF INVENTION

This invention relates to the field of nucleic acid detection methods in general and more particularly relates to the detection of nucleic acids by target-specific hybrid capture method.

BACKGROUND OF THE INVENTION

The detection of specific nucleic acid sequences present in a biological sample is important for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting and quantitating specific nucleic acid sequences is nucleic acid hybridization.

Various hybridization methods are available for the detection and study of nucleic acids. In a traditional hybridization method, the nucleic acids to be identified are either in a solution or affixed to a solid carrier. The nucleic acids are detected using labeled nucleic acid probes which are capable of hybridizing to the nucleic acids. Recently, new hybridization methods have been developed to increase the sensitivity and specificity of detection. One example is the hybrid capture method described in U.S. application Ser. No. 07/792,585. Although these new hybridization methods offer significant improvements over the traditional methods, they still lack the ability to fully discriminate between highly homologous nucleic acid sequences.

It is therefore an object of the present invention to provide a hybridization method which is not only rapid and sensitive, but is also highly specific and capable of discriminating highly homologous nucleic acid target sequences.

SUMMARY OF THE INVENTION

The present invention provides a novel nucleic acid detection method, referred to herein as target-specific hybrid capture ("TSHC"). TSHC is a highly specific and sensitive method which is capable of discriminating and detecting highly homologous nucleic acid target sequences.

In one embodiment, the method relates to detecting a target nucleic acid wherein the targeted nucleic acid, which is single-stranded or partially single-stranded, is hybridized simultaneously, or sequentially, to a capture sequence probe and an unlabeled signal sequence probe. These probes hybridize to non-overlapping regions of the target nucleic acid and not to each other so that double-stranded hybrids are formed. The hybrids are captured onto a solid phase and detected. In a preferred embodiment, a DNA/RNA hybrid is formed between the target nucleic acid and the signal sequence probe. Using this method, detection may be accomplished, for example, by binding a labeled antibody capable of recognizing a DNA/RNA hybrid to the double-stranded hybrid, thereby detecting the hybrid.

In another embodiment, the signal sequence probe used in the detection method is a nucleic acid molecule which comprises a DNA/RNA duplex and a single stranded nucleic acid sequence which is capable of hybridizing to the single-stranded or partially single-stranded target nucleic acid. Detection may be accomplished, for example, by binding a labeled antibody capable of recognizing the DNA/RNA duplex portion of the signal sequence probe, thereby detecting the hybrid formed between the target nucleic acid, the capture sequence probe and the signal sequence probe.

In yet another embodiment, the signal sequence probe used in the detection method is a molecule which does not contain sequences that are capable of hybridizing to the single-stranded or partially single-stranded target nucleic acid. Bridge probes comprising sequences that are capable of hybridizing to the target nucleic acid as well as sequences that are capable of hybridizing to the signal sequence probe are used. In this embodiment, the signal sequence probe comprises a DNA/RNA duplex portion and a single stranded DNA sequence portion containing sequences complementary to sequences within the bridge probe. The bridge probe, which hybridizes to both the target nucleic acid and the signal sequence probe, therefore serves as an intermediate for connecting the signal sequence probe to the target nucleic acid and the capture sequence probe hybridized to the target nucleic acid.

In another embodiment of the TSHC method of the invention, blocker probes comprising oligonucleotides complementary to the capture sequence probes are used in the method to eliminate excess capture sequence probe, thereby reducing the background signal in detection and increasing specificity of the assay.

The present invention also relates to novel probes. These probes are nucleic acid sequences which can function in various hybridization assays, including, for example, the TSHC assay.

DETAILED DESCRIPTION OF THE INVENTION

Figure 1:
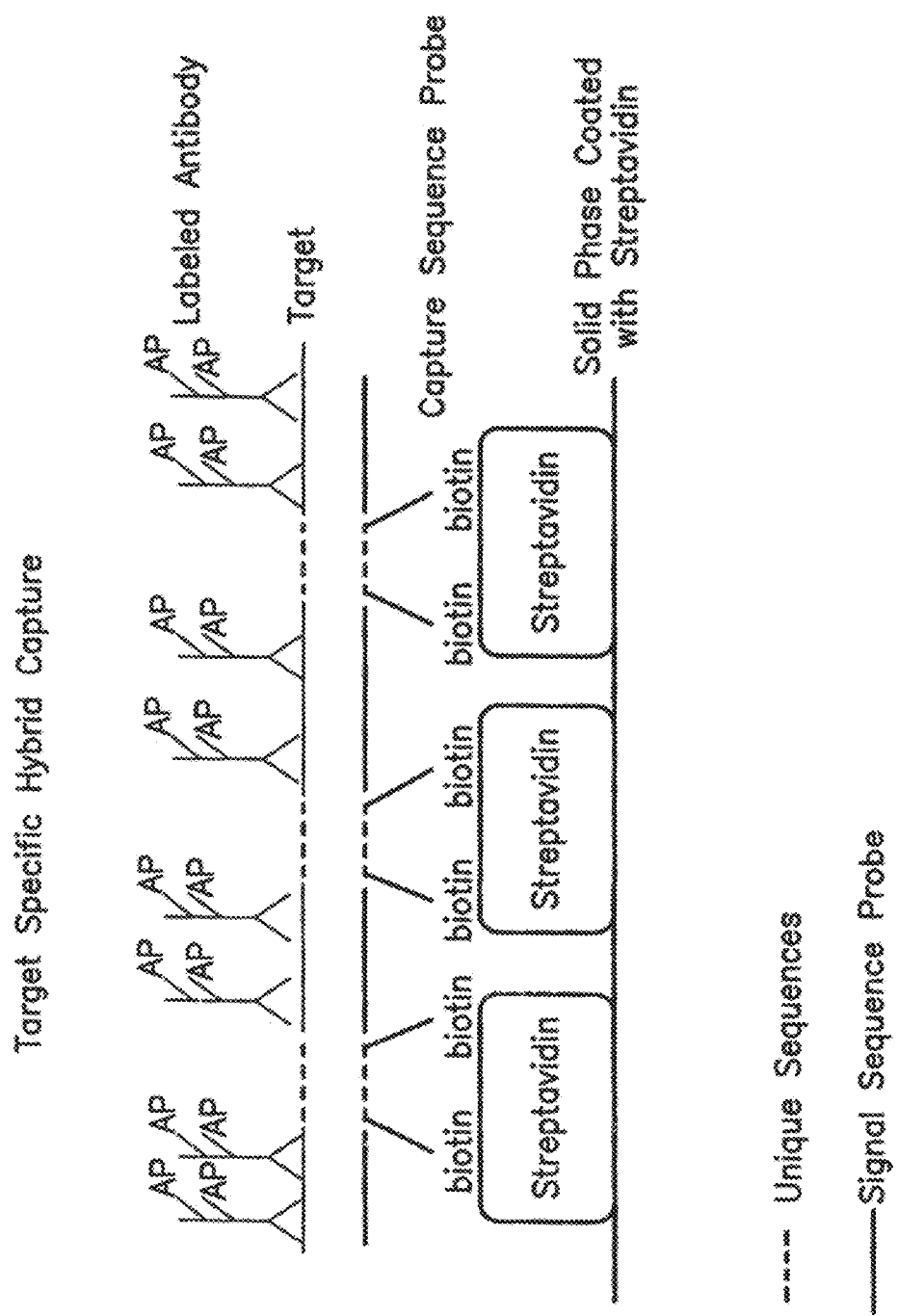
FIG. 1 is a schematic diagram illustrating one embodiment of the target-specific hybrid capture method.
Figure 2:
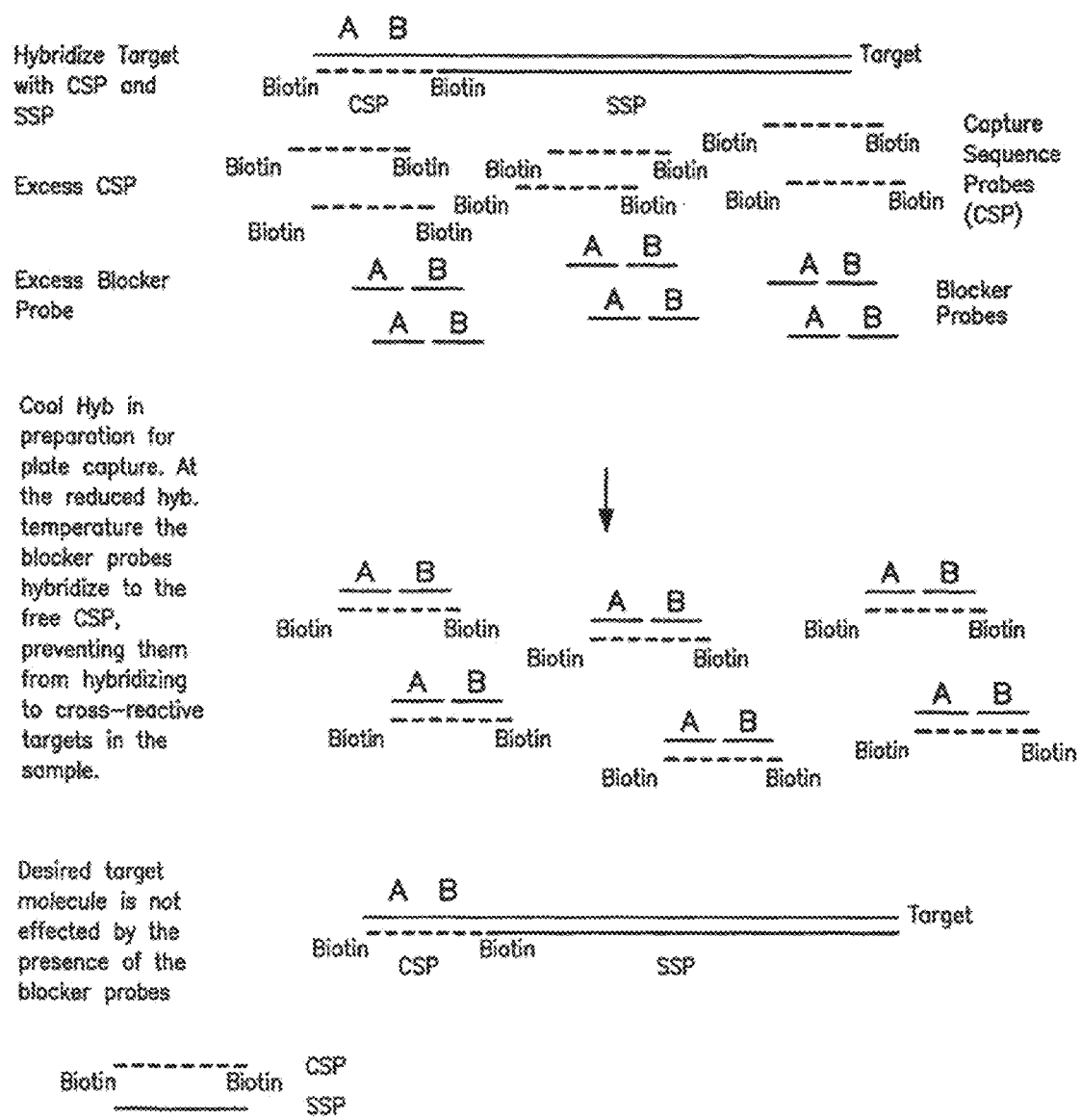
FIG. 2 is a schematic diagram illustrating one embodiment of the target-specific hybrid capture method.
Figure 3:
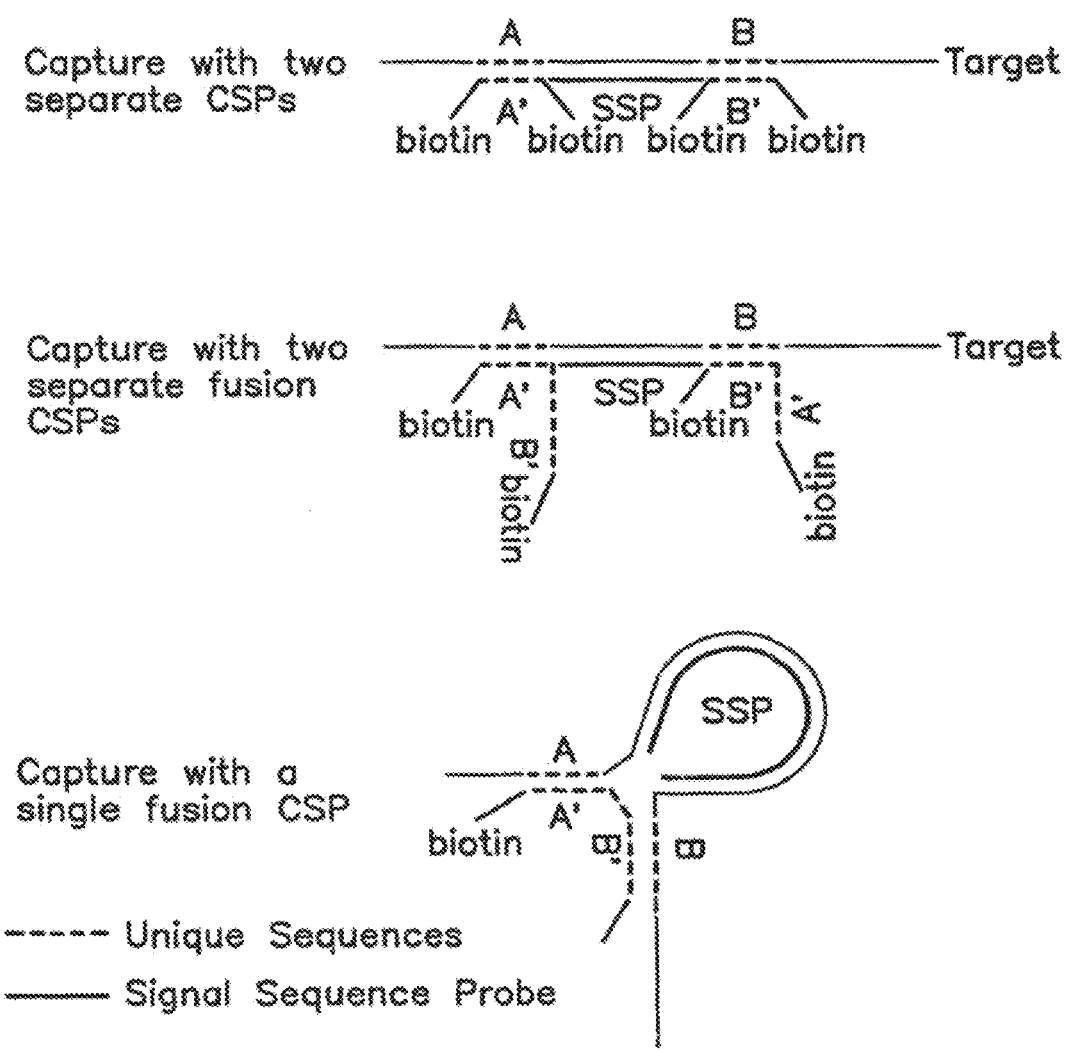
FIG. 3 is a schematic diagram illustrating possible mechanisms of action of an embodiment that employs fused capture sequence probes in target-specific hybrid capture detection.

The present invention provides a method for detecting the presence of nucleic acids in test samples. More specifically, the invention provides a highly specific and sensitive method which is capable of discriminating and detecting highly homologous nucleic acid sequences. Preferred uses for this invention are well known to the skilled artisan and may be applied to the detection and discrimination of a variety of mutations including, but not limited to insertions, deletions, inversions, repeated sequences, and multiple as well as single nucleotide polymorphisms (SNPs). Additionally, this invention may also be group specific for the detection of nucleic acid targets that share similar sequence elements.

Any source of nucleic acid, in purified or non-purified form, can be utilized as the test sample. For example, the test sample may be a food or agricultural product, or a human or veterinary clinical specimen. Typically, the test sample is a biological fluid such as urine, blood, plasma, serum, sputum or the like. Alternatively the test sample may be a tissue specimen suspected of carrying a nucleic acid of interest. The target nucleic acid in the test sample may be present initially as a discrete molecule so that the sequence to be detected constitutes the entire nucleic acid, or may only be a component of a larger molecule. It is not necessary that the nucleic acid sequence to be detected be present initially in a pure form. The test sample may contain a complex mixture of nucleic acids, of which the target nucleic acid may correspond to a gene of interest contained in total human genomic DNA or RNA or a portion of the nucleic acid sequence of a pathogenic organism which organism is a minor component of a clinical sample.

The target nucleic acid in a test sample can be DNA or RNA, such as messenger RNA, from any source, including bacteria, yeast, viruses, and the cells or tissues of higher organisms such as plants or animals. Methods for the extraction and/or purification of such nucleic acids are well known in the art. Target nucleic acids may be double-stranded or single-stranded. In the present method, it is preferred that the target nucleic acids are single-stranded or made single-stranded by conventional denaturation techniques prior to the hybridization steps of the method. In a preferred embodiment, base denaturation technique is used to denature the double-stranded target DNA.

The term "oligonucleotide" as the term is used herein refers to a nucleic acid molecule comprised of two or more deoxyribonucleotides or ribonucleotides. A desired oligonucleotide may be prepared by any suitable method, such as purification from a naturally occurring nucleic acid, by molecular biological means, or by de novo synthesis. Examples of oligonucleotides are nucleic acid probes described herein.

Nucleic acid probes are detectable nucleic acid sequences that hybridize to complementary RNA or DNA sequences in a test sample. Detection of the probe indicates the presence of a particular nucleic acid sequence in the test sample. In one embodiment, the target-specific hybrid capture method employs two types of nucleic acid probes: capture sequence probe (CSP) and signal sequence probe (SSP). A capture sequence probe comprises a nucleic acid sequence which is capable of hybridizing to unique region(s) within a target nucleic acid and being captured onto a solid phase. A signal sequence probe comprises a nucleic acid sequence which is capable of hybridizing to regions within a target nucleic acid that are adjacent to the unique regions recognized by the CSP. The sequences of CSP and SSP are selected so that they would not hybridize to the same region of a target nucleic acid or to each other.

In addition, the CSP and the SSP are selected to hybridize to regions of the target within 50,000 bases of each other. The distance between the sequence to which the CSP hybridizes within the target nucleic acid and the sequence to which the SSP hybridizes is preferably between 1 to 50,000 bases, more preferably, the distance is less than 3,000 bases. Most preferably, the distance is less than 1,000 bases.

The CSP used in the detection method can be DNA, RNA, peptide nucleic acids (PNAs), locked nucleic acids (LNAs), or other nucleic acid analogues. A "locked nucleic acid" as defined herein is a novel class of oligonucleotide analogues which form duplexes with complementary DNA and RNA with high thermal stability and selectivity. The usual conformational freedom of the furanose ring in standard nucleosides is restricted in LNAs due to the methylene linker connecting the 2'-O position to the 4'-C position. PNAs are oligonucleotides in which the sugar-phosphate backbone is replaced with a polyamide or "pseudopeptide" backbone. In a preferred embodiment, the CSP is DNA. The CSP has a minimum length of 6 bases, preferably between 15 to 100 bases long, and more preferably between 20 to 40 bases long. The CSP is substantially complementary to the sequence within a target nucleic acid to which it hybridizes. The sequence of a CSP is preferably at least 75% complementary to the target hybridization region, more preferably, 100% complementary to this sequence. It is also preferred that the CSP contains less than or equal to 75% sequence identity, more preferably less than 50% sequence identity, to non-desired sequences believed to be present in a test sample. The sequence within a target nucleic acid to which a CSP binds is preferably 6 bases long, more preferably 20-40 bases long. It may also be preferred that the sequences to which the CSP hybridizes are unique sequences or group-specific sequences. Group-specific sequences are multiple related sequences that form discrete groups.

In one embodiment, the CSP used in the detection method may contain one or more modifications in the nucleic acid which allows specific capture of the probe onto a solid phase. For example, the CSP may be modified by tagging it with at least one ligand by methods well-known to those skilled in the art including, for example, nick-translation, chemical or photochemical incorporation. In addition, the CSP may be tagged at multiple positions with one or multiple types of labels. For example, the CSP may be tagged with biotin, which binds to streptavidin; or digoxigenin, which binds to anti-digoxigenin; or 2,4-dinitrophenol (DNP), which binds to anti-DNP. Fluorogens can also be used to modify the probes. Examples of fluorogens include fluorescein and derivatives, phycoerythrin, allo-phycocyanin, phycocyanin, rhodamine, Texas Red or other proprietary fluorogens. The fluorogens are generally attached by chemical modification and bind to a fluorogen-specific antibody, such as anti-fluorescein. It will be understood by those skilled in the art that the CSP can also be tagged by incorporation of a modified base containing any chemical group recognizable by specific antibodies. Other tags and methods of tagging nucleotide sequences for capture onto a solid phase coated with substrate are well known to those skilled in the art. A review of nucleic acid labels can be found in the article by Landegren, et al., "DNA Diagnostics-Molecular Techniques and Automation", *Science*, 242:229-237 (1988), which is incorporated herein by reference. In one preferred embodiment, the CSP is tagged with biotin on both the 5' and the 3' ends of the nucleotide sequence. In another embodiment, the CSP is not modified but is captured on a solid matrix by virtue of sequences contained in the CSP capable of hybridization to the matrix.

The SSP used in the detection method may be a DNA or RNA. In one particular embodiment of the invention, the SSP and target nucleic acid form a DNA/RNA hybrid. Therefore, in this embodiment, if the target nucleic acid is a DNA, then the preferred SSP is an RNA. Similarly, if the target nucleic acid is RNA, then the preferred SSP is a DNA. The SSP is generally at least 15 bases long. However, the SSP may be up to or greater than 1000 bases long. Longer SSPs are preferred.

The SSP may comprise a single nucleic acid fragment, or multiple smaller nucleic acid fragments each of which is preferably between 15 to 100 bases in length.

Figure 6A:
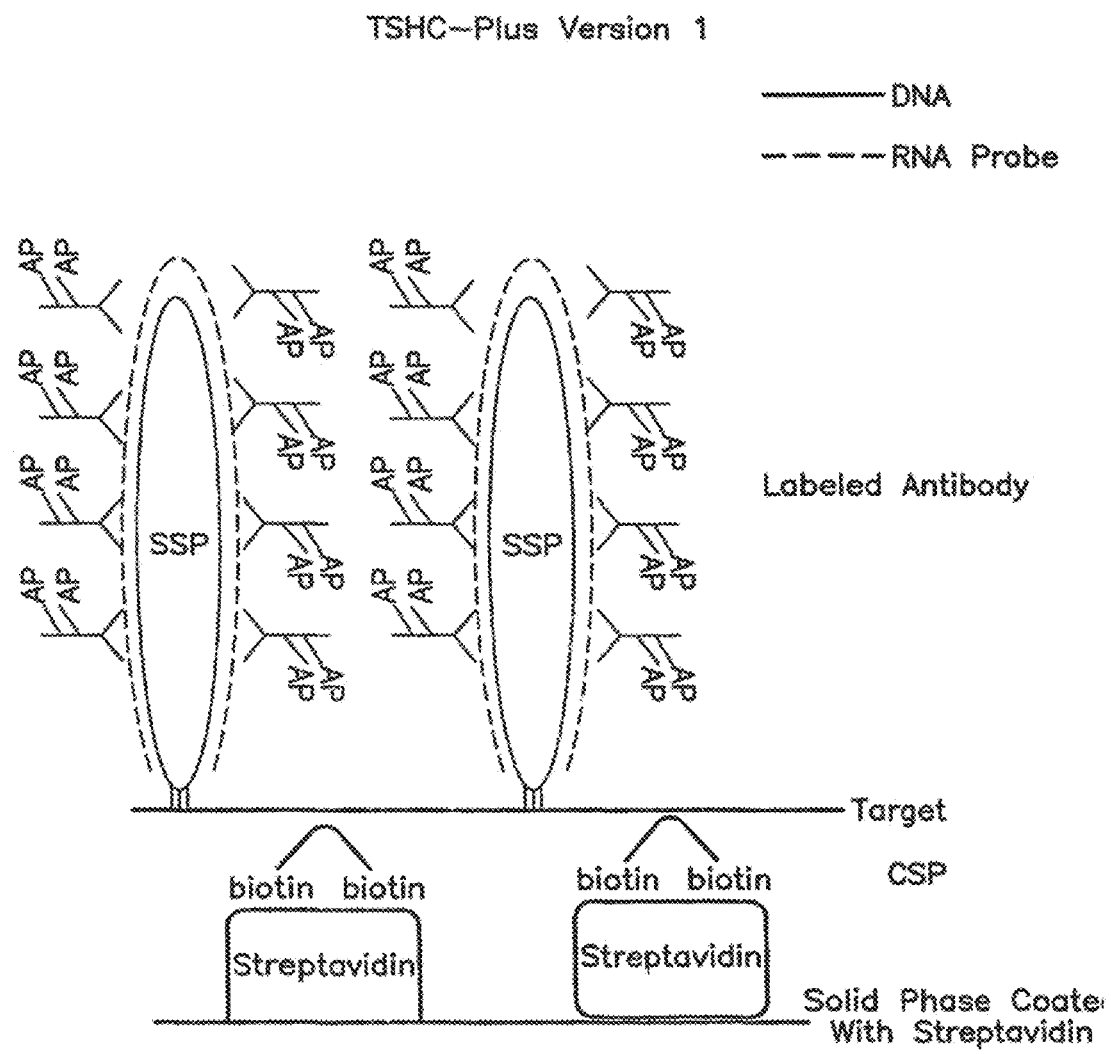
FIGS. 6A-6D show the various embodiments of the target-specific hybrid capture-plus method.

In another embodiment, the SSP used in the detection method comprises a DNA/RNA duplex and a single stranded nucleic acid sequence capable of hybridizing to the target nucleic acid (FIG. 6A). The SSP may be prepared by first cloning a single stranded DNA sequence complementary to sequences within the target nucleic acid into a single-stranded DNA vector, then hybridizing RNA complementary to the DNA vector sequence to generate a DNA/RNA duplex. For example, if M13 is used as the DNA vector, M13 RNA is hybridized to the M13 DNA sequence in the vector to generate a DNA/RNA duplex. The resulting SSP contains a DNA/RNA duplex portion as well as a single stranded portion capable of hybridizing to sequences within the target nucleic acid. The single stranded DNA should be at least 10 bases long, and may be up to or greater than 1000 bases long. Alternatively, the DNA/RNA duplex portion of the SSP may be formed during or after the reaction in which the single stranded portion of the SSP is hybridized to the target nucleic acid. The SSP can be linear, circular, or a combination of two or more forms. The DNA/RNA duplex portion of the SSP provides amplified signals for the detection of captured hybrids using anti-DNA/RNA antibodies as described herein.

Figure 6B:
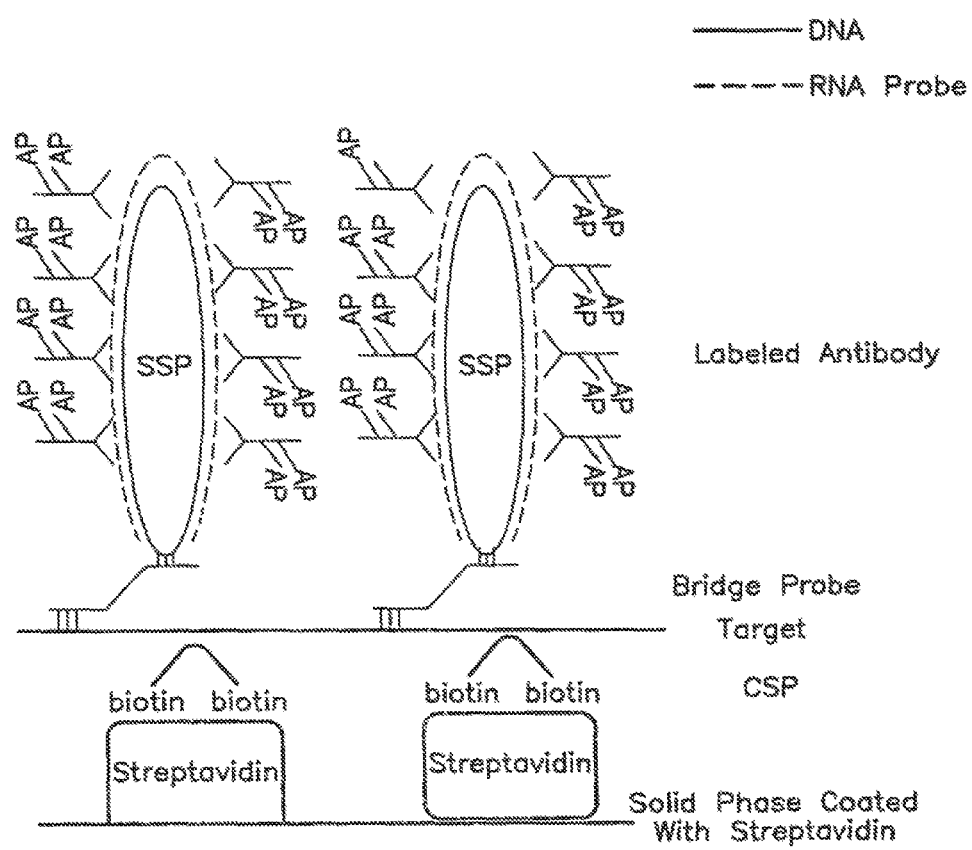
Figure 6C:
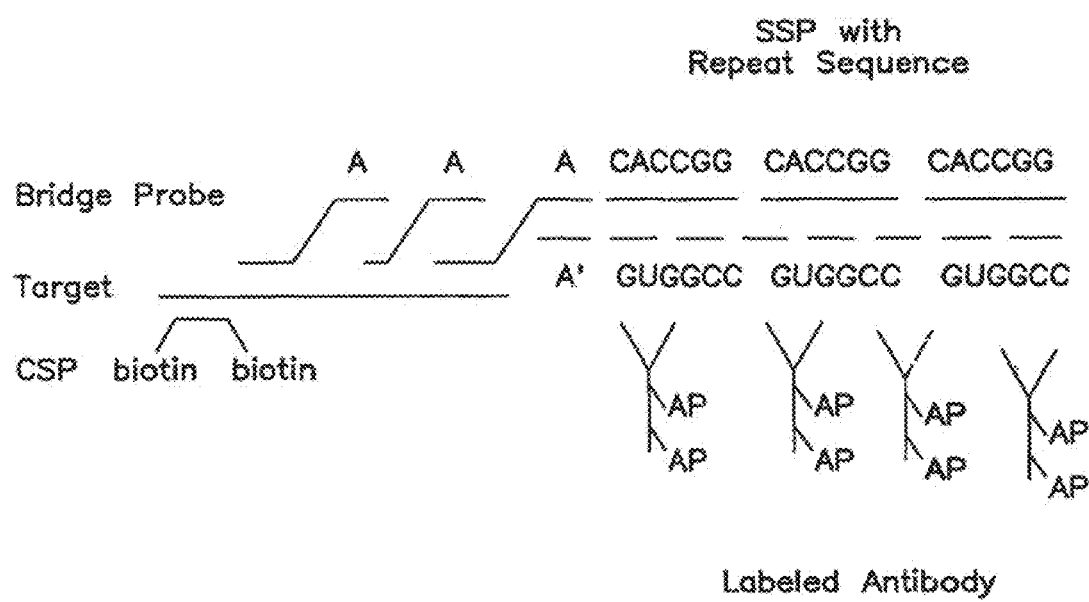
Figure 6D:
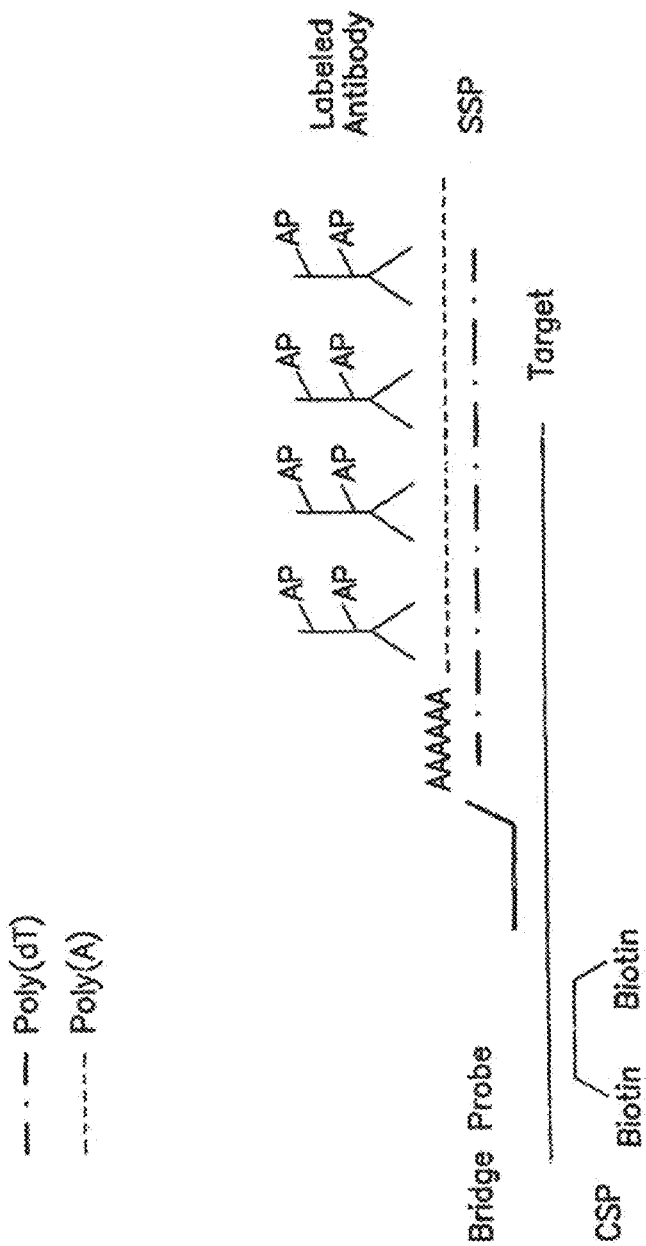

In yet another embodiment, the SSP used in the detection method is a molecule which does not contain sequences that are capable of hybridizing to the target nucleic acid. In this embodiment, bridge probes comprising sequences capable of hybridizing to the target nucleic acid as well as sequences capable of hybridizing to the SSP are used. The bridge probes can be DNA, RNA, peptide nucleic acids (PNAs), locked nucleic acids (LNAs), or other nucleic acid analogues. In one embodiment (FIG. 6B), the SSP comprises a DNA/RNA duplex portion and a single stranded portion containing sequences complementary to sequences within the bridge probe. The bridge probe, which is capable of hybridizing to both the target nucleic acid and the SSP, therefore serves as an intermediate for connecting the SSP to the target nucleic acid and the CSP hybridized to the target nucleic acid. The SSP may be prepared as described above. In another embodiment (FIG. 6C), the SSP used in the detection method comprises multiple sets of repeat sequences as well as a single stranded RNA sequence capable of hybridizing to the bridge probe. A DNA oligonucleotide probe containing sequences complementary to the repeat sequences may be used to hybridize to the SSP to generate the RNA/DNA duplex needed for signal amplification. In yet another embodiment (FIG. 6D), the bridge probe contains a poly(A) tail in addition to sequences which are capable of hybridizing to the target nucleic acid. The SSP used in this example comprises poly(dT) DNA sequences. The bridge probe therefore is capable of hybridizing to the SSP via its poly(A) tail. An RNA probe comprising poly(A) sequences may be used to hybridize to the remaining poly(dT) DNA sequences within SSP to form an RNA/DNA duplex. The SSP comprising poly(dT) sequences and the RNA probe comprising poly(A) sequences are preferably 100 to 5,000 bases long.

The SSP used in the detection method of the invention can be unmodified, or modified as with the CSP using methods described above and/or known in the art. In a preferred embodiment, the SSP is a covalently unmodified probe.

It is understood that multiple CSPs and/or SSPs can be employed in the detection method of the invention.

In another embodiment, an oligonucleotide probe comprising complementary sequences of two or more distinct regions of the target nucleic acid are fused together and used as the capture sequence probe in the method of the invention. Alternatively a single probe can be designed and produced which contains sequences complementary to single or multiple target nucleic acids. This type of probe is also referred to herein as a "fused" CSP. As shown in Example 5, the fused capture sequence probe works as effectively as the combination of two unfused CSPs when used at the same concentration.

Figure 7:
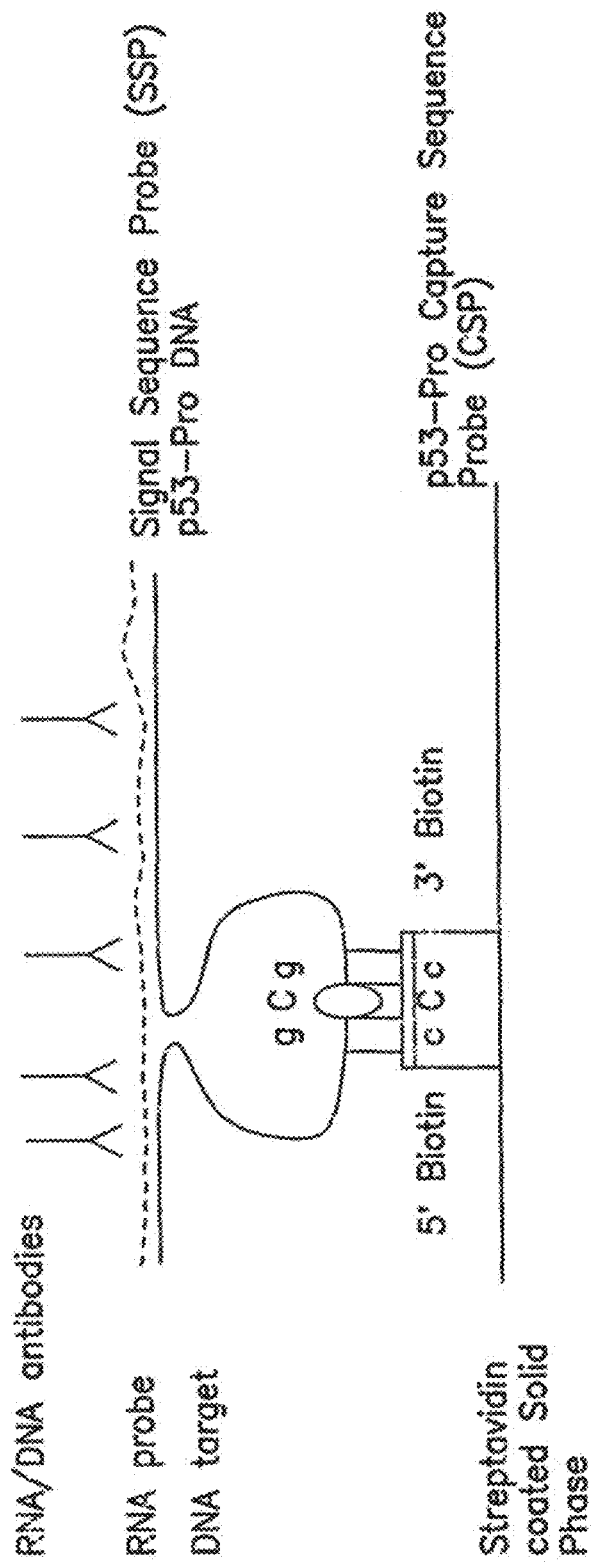
FIG. 7 shows the deletion probe embodiment of the target-specific hybrid capture method.

In a further embodiment of this invention, "deletion nucleic acid probes" may be used in TSHC. In order to minimize the number of transcription templates needed to be constructed, deletion nucleic acid probes, for example RNA, are designed such that 1) the length of probe used is maximized; and 2) probes are prevented from overlapping with the region targeted by the CSP. These deletion probes contain internal deletions in the nucleic acid template used to generate the probes. In addition, these deletion probes hybridize to nucleic acid targets creating "bubbles" of unhybridized nucleic acid that is accessible for CSP hybridization. This method also provides a very convenient means for making probes since the nucleic acid for the entire target may be cloned into a transcription vector and then sequences may be removed once they have been identified as useful regions for CSP hybridization. In addition, this method permits the use of nearly full length whole genome probes that do not overlap (i.e. do not hybridize to the same region) with the CSPs. Any commercially available mutagenesis kit can be used to design targeted deletions within a transcription template. Typically, the deletions of the nucleic acid template used for SSP synthesis are performed directly with the template cloned in the transcription vector. Deletions in the template are made such that the sequences overlapping the region hybridized by the CSP are removed. The deletions may be as small as the CSP region itself, but generally and more preferably, approximately 100 to 300 nucleotides on the 5' and 3' ends of the region hybridized by the CSP are deleted. (See FIG. 7).

The nucleic acid probes of the invention may be produced by any suitable method known in the art, including for example, by chemical synthesis, isolation from a naturally-occurring source, recombinant production and asymmetric PCR (McCabe, 1990 In: *PCR Protocols: A guide to methods and applications*. San Diego, Calif., Academic Press, 76-83). It may be preferred to chemically synthesize the probes in one or more segments and subsequently link the segments. Several chemical synthesis methods are described by Narang et al. (1979 *Meth. Enzymol.* 68:90), Brown et al. (1979 *Meth. Enzymol.* 68:109) and Caruthers et al. (1985 *Meth. Enzymol.* 154:287), which are incorporated herein by reference. Alternatively, cloning methods may provide a convenient nucleic acid fragment which can be isolated for use as a promoter primer. A double-stranded DNA probe is first rendered single-stranded using, for example, conventional denaturation methods prior to hybridization to the target nucleic acids.

Hybridization is conducted under standard hybridization conditions well known to those skilled in the art. Reaction conditions for hybridization of a probe to a nucleic acid sequence vary from probe to probe, depending on factors such as probe length, the number of G and C nucleotides in the sequence, and the composition of the buffer utilized in the hybridization reaction. Moderately stringent hybridization conditions are generally understood by those skilled in the art as conditions approximately 25° C. below the melting temperature of a perfectly base-paired double stranded DNA. Higher specificity is generally achieved by employing incubation conditions having higher temperatures, in other words more stringent conditions. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes in great detail, including a description of the factors involved and the level of stringency necessary to guarantee hybridization with specificity. Hybridization is typically performed in a buffered aqueous solution, for which conditions such as temperature, salt concentration, and pH are selected to provide sufficient stringency such that the probes hybridize specifically to their respective target nucleic acid sequences but not any other sequence.

Generally, the efficiency of hybridization between probe and target improve under conditions where the amount of probe added is in molar excess to the template, preferably a 2 to $10^6$ molar excess, more preferably $10^3$ to $10^6$ molar excess. The concentration of each CSP provided for efficient capture is at least 25 fmoles/ml (25 pM) in the final hybridization solution, preferably between 25 fmoles to $10^4$ fmoles/ml (10 nM). The concentration of each SSP is at least 15 ng/ml in the final hybridization solution, preferably 150 ng/ml. Table A shows the conversion of SSP concentrations expressed in ng/ml to molar basis.

TABLE A

CONVERSION OF SSP CONCENTRATION FROM ng/ml TO fmoles/ml

| SSP Concentration in ng/ml | SSP Concentration in fmoles/ml (pM) | |
|---|---|---|
| | SSP is a 3 kb RNA | SSP is a 5 kb RNA |
| 15 ng/ml | 15.1 | 9 |
| 150 ng/ml | 151 | 90 |
| 600 ng/ml | 606 | 364 |

Hybridization of the CSP and the SSP to the target nucleic acid may be performed simultaneously or sequentially and in either order. In one embodiment, hybridization of the CSP and hybridization of the SSP to the target nucleic acid are performed simultaneously. The hybrid formed is then captured onto a solid phase coated with a substrate to which ligand attached to the CSP binds with specificity. In another embodiment, hybridization of the SSP to the target nucleic acid is performed after the hybridization of the CSP to the target nucleic acid. In this case, the CSP may be immobilized on a solid phase before or after hybridization. In this embodiment, both the CSP and the target may be bound to the solid phase during the SSP hybridization reaction. Most preferably, the CSP and SSP are hybridized to the target nucleic acid, forming a hybridized complex, wherein said complex is then captured onto a solid phase coated with a substrate to which ligand attached to the CSP binds with specificity.

In order to identify and detect specific polynucleotide sequences with added specificity and sensitivity, assays can be designed such that conditions are optimal for increasing signal detection and reducing background interference. Preferred methods for achieving added stringency include the TSHC heated capture step and/or through the use of blocker probes. Since capture efficiency of the hybridized complex comprising CSP, SSP, and target nucleic acid is influenced by several assay conditions, a heated capture may be useful for reducing false reactivity and detecting mutations of at least one nucleotide. Preferably, the heated capture method is employed for the detection of single nucleotide polymorphisms. Briefly, the heated capture method for capturing or binding the hybridized complex to a solid phase utilizes an elevated range of temperatures. In order to immobilize CSP hybridized targets following hybridization, the hybridization solution is placed into wells of a 96-well plate, for example, and the plate is shaken for 15 minutes to 2 hours at temperatures ranging from 20° C. to 90° C. shaking at 1100 rpms. Optionally, hybridization at room temperature for 1 hour shaking at 1100 rpms may be preferred. Capture temperatures above room temperature may be preferred for an added level of stringency as hybridization (and "promiscuous hybridization") does occur during the plate capture step. Another means for attaining a higher degree of specificity and sensitivity is through the use of blocker probes.

One embodiment of this invention provides a heated capture method using elevated temperatures for capturing a hybridized SSP and target nucleic acid complex to a CSP immobilized to a solid phase, either simultaneously or sequentially, where the elevated temperature prevents non-specific hybridization of the CSP from occurring during the plate capture step. The elevated temperature also affects SSP hybridization specificity. The CSP used in TSHC may be a nucleic acid or modified nucleic acid, preferably DNA, which contains a modification that permits capture onto a solid phase. One example of such a modification is a biotin label and more preferably multiple biotin labels. The CSP contains a minimum of 6 base pairs, preferably 16 to 50 bases with a preferred melting temperature (Tm) above 65° C. Preferred CSPs may comprise sequences complementary to unique sequences within the target molecule of nucleic acids present in the sample, although this is not necessary for targeting multiple nucleic acid species. For example, if a gene family is the target, the CSP may preferably comprise a sequence element common to one or more members of the gene family. For most applications, the CSP preferably contains at most 75% sequence identity and more preferably less than 50%, to non-desired targets suspected of being present in the sample. The assay can utilize CSPs that differ in only a single nucleotide and selectively detect targets that differ in only a single nucleotide. This degree of discrimination can be facilitated by using the heated plate capture step. When CSP hybridization is performed in solution, the samples are subsequently reacted with a solid phase for capture. For example, if a biotin-labeled CSP is used, avidin or some other biotin binding protein may be used to coat the solid phase for capture. Another embodiment of this invention encompasses the simultaneous hybridization and capture, wherein hybridization is performed directly on the capture solid phase, for example on a capture plate.

In yet another embodiment of this invention, the TSHC method can be used to distinguish and detect nucleic acid targets with SNPs. This Hybrid Capture-Single Nucleotide Polymorphism (HC-SNP) detection method can detect SNPs with high sensitivity and specificity. An example illustrating the extended capability of TSHC for distinguishing and detecting nucleic acid targets with SNPs is described herein, where in labeled capture oligonucleotides (CSP) are used, in addition to signal sequence probes (SSP), and a target nucleic acid molecule. The CSPs may hybridize and capture nucleic acid targets to a solid phase or surface (for example, a 96-well plate). Labeling methods are well known in the art and may also be employed to facilitate target nucleic acid immobilization.

In one example, a target nucleic acid capture is achieved through the high affinity interaction between a biotin on the CSP and a streptavidin on the solid surface. Simultaneously, an RNA signal sequence probe (SSP) complementary to a DNA target and not overlapping with the capture region is hybridized to the DNA target. The RNA/DNA hybrids are recognized by antibody directed against RNA/DNA hybrids labeled with alkaline phosphatase. In this example, a chemiluminescent phosphorylated substrate is then added and subsequently, the activated substrate may be detected and measured by a luminometer. The signal to noise ratios are determined using a known negative control. Further, the concentration of the target can be determined by using known concentrations of target molecules as calibrators. The specificity of binding and capturing the hybrid to a solid phase is modulated, regulated, or adjusted by temperatures of greater than room temperature, by the addition of blocker probes, or by temperatures of greater than room temperature and the addition of blocker probes. For additional stringency, blocker probes may be used either with or without the heated capture method. Alternatively, the capture step may be performed at room temperature and may optionally utilize blocker probes.

Another embodiment of this invention further provides a blocker oligonucleotide method where in many cases, obviates the need for a heated capture step. This may be achieved by hybridizing blocker oligonucleotides to capture oligonucleotides at room temperature, thereby preventing further hybridization of the CSP to undesired targets during the capture step. Capture probes may preferably require the presence of blocker probes, which are complementary to the capture probe. The length of the blocker probes can vary from blockers complementary to the full length CSP to very short blockers complementary to only a small portion of the CSP. For example, blocker probes can be 4-10 base pairs shorter than the length of the CSP. The presence of the blocker probes reduces background and enables a higher degree of sensitivity. The heated capture step and blocker probes may be used either separately or together, wherein the specificity of binding and capturing the hybrid to a solid phase is modulated, regulated, or adjusted by temperatures of greater than room temperature and the addition of blocker probes.

It will be understood by those skilled in the art that a solid phase or matrix includes, for example, polystyrene, polyethylene, polypropylene, polycarbonate or any solid plastic material in the shape of plates, slides, dishes, beads, particles, microparticles, cups, strands, chips and strips. A solid phase also includes glass beads, glass test tubes and any other appropriate glass product. A functionalized solid phase such as plastic or glass that has been modified so that the surface contains carboxyl, amino, hydrazide, aldehyde groups, nucleic acid or nucleotide derivatives can also be used. Any solid phase such as plastic or glass microparticles, beads, strips, test tubes, slides, strands, chips or microtiter plates can be used.

In one preferred embodiment, the CSP is labeled with biotin, and streptavidin-coated or avidin-coated solid phase is employed to capture the hybrid. More preferably, streptavidin-coated microtiter plates are used. These plates may be coated passively or covalently.

The captured hybrid may be detected by conventional means well-known in the art, such as with a labeled polyclonal or monoclonal antibody specific for the hybrid, an antibody specific for one or more ligands attached to the SSP, a labeled antibody, or a detectable modification on the SSP itself.

One preferred method of detection detects the captured hybrid by using an antibody capable of binding to the RNA/DNA hybrid (referred to herein as the "RNA/DNA antibody". In this embodiment, the anti-RNA/DNA antibody is preferably labeled with an enzyme, a fluorescent molecule or a biotin-avidin conjugate and is non-radioactive. The label can be detected directly or indirectly by conventional means known in the art such as a colorimeter, a luminometer, or a fluorescence detector. One preferred label is, for example, alkaline phosphatase. Other labels known to one skilled in the art can also be employed as a means of detecting the bound double-stranded hybrid.

Detection of captured hybrid is preferably achieved by binding the conjugated antibody to the hybrid during an incubation step. Surfaces are then washed to remove any excess conjugate. These techniques are known in the art. For example, manual washes may be performed using either an Eppendorf™ Repeat Pipettor with a 50 ml Combitip™ (Eppendorf, Hamburg, Germany), a Corning repeat syringe (Corning, Corning, N.Y.), a simple pump regulated by a variostat, or by gravity flow from a reservoir with attached tubing. Commercially available tube washing systems available from Source Scientific Systems (Garden Grove, Calif.) can also be used.

Bound conjugate is subsequently detected by a method conventionally used in the art, for example, colorimetry or chemiluminescence as described at Coutlee, et al., *J. Clin. Microbial* 27:1002-1007 (1989). Preferably, bound alkaline phosphatase conjugate is detected by chemiluminescence by adding a substrate which can be activated by alkaline phosphatase. Chemiluminescent substrates that are activated by alkaline phosphatase are well known in the art.

In another embodiment, the target specific hybrid capture method of the invention employs blocker probes in addition to the CSP and SSP. A blocker probe comprises sequences that are complementary to the sequences of the CSP. The sequence of a blocker probe is preferably at least 75% complementary to the sequence of the CSP, more preferably, 100% complementary to the CSP. The addition of the blocker probes to the hybridization reaction mixture prevents non-hybridized CSP from hybridizing to cross-reactive nucleic acid sequences present in the target and therefore increases the specificity of the detection.

The blocker probe is generally at least 5 bases long, preferably 12 bases long. The concentration of the blocker probe in the hybridization reaction is preferably in excess to that of the CSP and SSP. Preferably, the blocker probe is present in a 2-fold molar excess, although, it may be present in an up to 10,000-fold molar excess. The blocker probes can be DNA, RNA, peptide nucleic acids (PNAs) or other nucleic acid analogues.

In one embodiment, blocker probes complementary to the full-length or near full-length of the CSP are used. Following the reaction in which the hybrid between CSP, SSP and the target nucleic acid is formed, one or more blocker probes may be added to the reaction and the hybridization is continued for a desired time. The hybridization products are then detected as described above.

In another embodiment, blocker probes complementary to only a portion of the CSP and shorter than the CSP are used. These blocker probes have a lower melting temperature than that of the CSP. Preferably, the melting temperature of the blocker probe is 10 degrees lower than that of the CSP. In this case, the blocker probe is preferably added to the target nucleic acids simultaneously with the CSP and the SSP. Since the blocker probe has a lower melting temperature than the CSP, the initial temperature for hybridization is chosen such that the blocker probe does not interfere with the hybridization of the CSP to its target sequences. However, when the temperature of the hybridization mixtures is adjusted below the temperature used for target hybridization, the blocker probe hybridizes to the CSP and effectively blocks the CSP from hybridizing to cross-reactive nucleic acid sequences. For example, when the hybridization products are incubated at room temperature on a streptavidin-coated microtiter plate during hybrid capture, the blocker probes may be added.

The following examples illustrate use of the present amplification method and detection assay and kit. These examples are offered by way of illustration, and are not intended to limit the scope of the invention in any manner. All references described herein are expressly incorporated in toto by reference.

EXAMPLE 1

Target-Specific Hybrid Capture (TSHC) Assay Protocol

Herpes Simplex Virus 1 (HSV-1) and Herpes Simplex Virus 2 (HSV-2) viral particles of known concentration (Advanced Biotechnologies, Inc., Columbia, Md.) or clinical samples were diluted using either Negative Control Media (Digene Corp., Gaithersburg, Md.) or Negative Cervical Specimens (Digene). Various dilutions were made and aliquoted into individual microfuge tubes. A half volume of the Denaturation Reagent 5100-0431 (Digene) was added. Test samples were incubated at 65° C. for 45 minutes for denaturation of nucleic acids in the samples.

Following denaturation, a hybridization solution containing signal sequence probes (SSPs) (600 ng/ml each) and capture sequence probes (CSPs) (2.5 pmoles/ml each) was added to the sample, and incubated at 74° C. for 1 hour. Blocker probes in a solution containing one volume of 4× Probe Diluent (Digene), one volume of Denaturation Reagent, and two volumes of the Negative Control Media were then added to the hybridization mixture and incubated at 74° C. for 15 minutes.

In a second series of experiments, following denaturation of nucleic acids, a hybridization mixture containing SSPs (600 ng/ml each), CSPs (2.5 pmoles/ml each), and blocker probes (250 pmoles/ml each) was added to the samples and incubated for one hour at 74° C.

Tubes containing reaction mixtures were cooled at room temperature for 5 minutes, and aliquots were taken from each tube and transferred to individual wells of a 96-well streptavidin capture plate (Digene). The plates were shaken at 1100 rpms for 1 hour at room temperature. The supernatants were then decanted and the plates were washed twice with Hybrid Capture 2 wash buffer (Digene) and inverted briefly to remove residual wash buffer. The alkaline-phosphatase anti-RNA/DNA antibody detection reagent-1 (DR-1; Digene) was then added to each well and incubated for 30 minutes at room temperature (about 20° C. to 25° C.). The wells were then subjected to multiple wash steps which include: 1) three washes with Sharp wash buffer (Digene) at room temperature; 2) incubation of the plate with the Sharp wash buffer for 10 minutes at 60° C. on a heat block; 3) two washes with the Sharp wash buffer at room temperature; and 4) one wash with the SNM wash buffer (Digene) at room temperature. Following removal of the residual liquid, luminescent substrate 5100-0350 (Digene) was added to each well and incubated for 15 minutes at room temperature. The individual wells were then read on a plate luminometer to obtain the relative light unit (RLU) signal.

Solutions containing Negative Control Media or known HSV Negative Cervical Specimens were used as negative controls for the test samples. The signal to noise ratio (S/N) was calculated as the ratio of the average RLU obtained from a test sample to the average RLU of the negative control. The signal to noise ratio was used as the basis for determining capture efficiency and the detection of target nucleic acids. A S/N value of 2 or greater was arbitrarily assigned as a positive signal while a S/N value less than 2 was considered negative. The coefficient of variation (CV) which is a determination of the variability of the experiment within one sample set was calculated by taking the standard deviation of the replicates, dividing them by the average and multiplying that value by 100 to give a percent value.

The capture sequence probes and the blocker probes used in experiments described in Examples 2-13 were synthesized using the method described by Cook et al. (1988 *Nucl. Acid. Res.* 16: 4077-95). Unless otherwise noted, the capture sequence probes used in the experiments described herein were labeled with biotins at their 5' and 3' ends.

The signal sequence probes used in experiments described in Examples 2-13 are RNA probes, but this invention is not limited to SSPs comprising RNA. These probes were prepared using the method described by Yisraeli et al. (1989, *Methods in Enzymol.*, 180: 42-50).

EXAMPLE 2

The following tables describe the various probes used in experiments described in Examples 3-13.

TABLE 1

HSV-1 CLONES FROM WHICH HSV-1 PROBES ARE DERIVED

| Clone Name | Host Vector | Cloning Site(s) | Insert Size (bp) | Sequence Location within HSV-1 |
|---|---|---|---|---|
| RH3 | Dgx3 | Hind III, Eco RI | 5720 | 39850-45570 |
| R10 | Blue Script SK+ | Eco RI | 4072 | 64134-68206 |
| RH5B | Blue Script SK+ | Eco RV, Eco RI | 4987 | 105108-110095 |
| H19 | Blue Script SK+ | Hind III | 4890 | 133467-138349 |

TABLE 2

HSV-2 CLONES FROM WHICH HSV-2 PROBES ARE DERIVED

| Clone Name | Host Vector | Cloning Site(s) | Insert Size (bp) | Sequence Location in HSV-2 |
|---|---|---|---|---|
| E4A | Blue Script SK+ | Bam HI | 3683 | 23230-26914 |
| E4B | Blue Script SK+ | Bam HI Eco RI | 5600 | 26914-32267 |
| I8 | Blue Script SK+ | Hind III | 2844 | 41624-44474 |
| EI8 | Dgx3 | Hind III, Eco RI | 3715 | 44474-48189 |
| 4L | Blue Script KS+ | Bam HI, Eco RI | 4313 | 86199-90512 |

TABLE 3

CAPTURE SEQUENCE PROBES FOR HSV-1

| Probe | Sequence | Size (bp) | Location within HSV-1 |
|---|---|---|---|
| TS-1 | (TTATTATTA)CGTTTCATGTCGGCAAACAGCTCGT(TTATTATTA) [SEQ ID NO: 1] | 24 | 105040-105063 |
| TS-2 | (TTATTATTA)CGTCCTGGATGGCGATACGGC(TTATTATTA) [SEQ ID NO: 2] | 21 | 110316-110336 |
| VH-3 | CGTCCTGGATGGCGATACGGC [SEQ ID NO: 3] | 21 | 110316-110336 |
| NC-1 | CGTTCATGTCGGCAAACAGCTCGT [SEQ ID NO: 4] | 24 | 105040-105063 |
| VH-4 (fusion of VH3, NC-1) | CGTTCATGTCGGCAAACAGCTCGT-CGTCCTGGATGGCGATACGGC [SEQ ID NO: 5] | 45 | 105040-105063; 110316-110336 |
| HZ-1 | GATGGGTTATTTTTCCTAAGATGGGGCGGGTCC [SEQ ID NO: 6] | 34 | 133061-133094 |
| VH-2 | TACCCCGATCATCAGTTATCCTTAAGGT [SEQ ID NO: 7] | 28 | 138367-138394 |
| FD-1 | AAACCGTTCCATGACCGGA [SEQ ID NO: 8] | 19 | 39281-39299 |
| RA-2 | ATCGCGTGTTCCAGAGACAGGC [SEQ ID NO: 9] | 22 | 39156-39177 |
| NC-2 | CAACGCCCAAAATAATA [SEQ ID NO: 10] | 17 | 46337-46353 |
| FD-2 | GTCCCCGAaCCGATCTAGCG (note small cap a is mutated base) [SEQ ID NO: 11] | 20 | 45483-45502 |
| RA-4 | CGAACCATAAACCATTCCCCAT [SEQ ID NO: 12] | 22 | 46461-46382 |
| ON-3 | CACGCCCGTGGTTCTGGAATTCGAC [SEQ ID NO: 13] | 25 | 64105-64129 |
| HZ-2 | (TTTATTA)GATGGGGTTATTTTTCCTAAGATGGGGCGGGTCC [SEQ ID NO: 14] | 34 | 133061-133094 |
| ZD-1 | GGTTATTTTTCCTAAG [SEQ ID NO: 15] | 16 | 133064-133079 |
| ZD-2 | (ATTATT)GGTTATTTTTCCTAAG(ATTATT) [SEQ ID NO: 16] | 16 | 133064-133079 |
| F6R | ACGACGCCTTGACTCCGATTCGTCATCGGATGACTCCCT [SEQ ID NO: 17] | 40 | 87111-87150 |
| DRH19 | ATGCGCCAGTGTATCAATCAGCTGTTTCGGGT [SEQ ID NO: 18] | 32 | 133223-133254 |
| F15R | CAAAACGTCCTGGAGACGGGTGAGTGTCGGCGAGGACG [SEQ ID NO: 19] | 38 | 141311-141348 |
| VH-1 | GTCCCCGACCCGATCTAGCG [SEQ ID NO: 20] | 20 | 45483-45502 |
| ON-4 | GCAGACTGCGCCAGGAACGAGTA [SEQ ID NO: 21] | 23 | 68404-68426 |
| PZ-1 | GTGCCCACGCCCGTGGTTCTGGAATTCGACAGCGA [SEQ ID NO: 22] | 35 | 64105-64139 |

TABLE 3-continued

CAPTURE SEQUENCE PROBES FOR HSV-1

| Probe | Sequence | Size (bp) | Location within HSV-1 |
|---|---|---|---|
| PZ-2 | GCAGACTGCGCCAGGAACGAGTAGTTGGAGTACTG [SEQ ID NO: 23] | 35 | 68404-68438 |
| FG-2 | AAGAGGTCCATTGGGTGGGGTTGATACGGGAAAGAC [SEQ ID NO: 24] | 36 | 105069-105104 |
| FG-3 | CGTAATGCGGCGGTGCAGACTCCCCTG [SEQ ID NO: 25] | 27 | 110620-110646 |
| FG-4 | CCAACTACCCCGATCATCAGTTATCCTTAAGGTCTCTTG [SEQ ID NO: 26] | 39 | 138362 - 138400 |
| Hsv1-LF15R (SH-3) | (AAAAAAAAA)CAAAACGTCCTGGAGACGGGTGAGTGTCGGCGAGGACG [SEQ ID NO: 27] | 38 | 141311-141348 |
| Hsv1-F15-2B (GZ-1) | CAAAACGTCCTGGAGACGGGTGAGTGTCGGCGAGGACG [SEQ ID NO: 28] | 38 | 141311-141348 |
| Hsv1-F15-3B (GZ-2) | CAAAACGTCC-bio-U-GGAGACGGGTGAGTG-bio-U-CGGCGAGGACG [SEQ ID NO: 29] | 38 | 141311-141348 |

* Sequences in parentheses are "tail" sequences not directed at HSV.

TABLE 4

BLOCKER PROBES FOR HSV-1

| Probe | Sequence | Size (bp) | Capture Probe to which it hybridizes |
|---|---|---|---|
| EA-1 | AGGAAAAATAACCCCATC [SEQ ID NO: 30] | 18 | HZ-1 |
| EA-2 | GACCCGCCCCATCTT [SEQ ID NO: 31] | 15 | HZ-1 |
| ZD-3 | GGACCCGCCCCATCTTAGGAAAAATAACCCCATC [SEQ ID NO: 32] | 34 | HZ-1 |
| NG-7 | AAAAATAACCCCA [SEQ ID NO: 33] | 13 | HZ-1 |
| NG-8 | CGCCCCATCTT [SEQ ID NO: 34] | 11 | HZ-1 |
| NG-4 | CCATCTTAGGAAAAA [SEQ ID NO: 35] | 15 | HZ-1 |
| GP-1 | ATAACTGATGATCGG [SEQ ID NO: 36] | 15 | VH-Z |
| EA-3 | CCACCCAATGGACCTC [SEQ ID NO: 37] | 16 | FG-2 |
| EA-4 | GTCTTTCCCGTATCAACC [SEQ ID NO: 38] | 18 | FG-2 |
| EB-7 | CGCCGCATTACG [SEQ ID NO: 39] | 12 | FG-3 |
| EB-8 | AGGGGAGTCTGC [SEQ ID NO: 40] | 12 | FG-3 |
| GP-3 | CTGTTTGCCGACA [SEQ ID NO: 41] | 13 | VH-4 |
| GP-4 | TATCGCCATCCAG [SEQ ID NO: 42] | 13 | VH-4 |
| EB-9 | ATGATCGGGGTAGT [SEQ ID NO: 43] | 14 | FG-4 |
| EB-10 | AGAGACCTTAAGGATA [SEQ ID NO: 44] | 16 | FG-4 |
| NG-1 | ATTCCAGAACCACGG [SEQ ID NO: 45] | 15 | ON-3 |
| NG-2 | TTCCAGAACCACG [SEQ ID NO: 46] | 13 | ON-3 |
| NG-3 | TCCAGAACCAC [SEQ ID NO: 47] | 11 | ON-4 |
| GP-5 | GTTCCTGGCGCAG [SEQ ID NO: 48] | 13 | ON-4 |
| GP-6 | TTCCTGGCGCAG [SEQ ID NO: 49] | 12 | ON-4 |

TABLE 5

CAPTURE SEQUENCE PROBES FOR HSV-2

| Probe | Sequence | Size (bp) | Location within HSV-2 |
|---|---|---|---|
| NF-1 | GCCCGCGCCGCCAGCACTACTTTC [SEQ ID NO: 50] | 24 | 41610-41587 |

TABLE 5-continued

CAPTURE SEQUENCE PROBES FOR HSV-2

| Probe | Sequence | Size (bp) | Location within HSV-2 |
|---|---|---|---|
| FG-1 | AAACGTTGGGAGGTGTGTGCGTCATC CTGGAGCTA [SEQ ID NO: 51] | 35 | 48200-48234 |
| LE-3 | GACCAAAACCGAGTGAGGTTCTGTGT [SEQ ID NO: 52] | 26 | 48732-48757 |
| NF-2 | AAACGTTGGGAGGTGTGTGCGTCA [SEQ ID NO: 53] | 24 | 48200-48223 |
| RA-3 | TGCTCGTCACGAAGTCACTCATG [SEQ ID NO: 54] | 23 | 22756-22734 |
| ON-2 | CATTACTGCCCGCACCGGACC [SEQ ID NO: 55] | 21 | 23862-23842 |
| LE-1 | GCCGTGGTGTTCCTGAACACCAGG [SEQ ID N0: 56] | 24 | 27666-27643 |
| LE-4 | AGTCAGGGTTGCCCGACTTCGTCAC [SEQ ID NO: 57] | 25 | 22891-22867 |
| NF-3 | CAGGCGTCCTCGGTCTCGGGCGGGC [SEQ ID NO: 58] | 26 | 32847-32822 |
| NF-4 | CCCACGTCACCGGGGGCCCC [SEQ ID N0: 59] | 20 | 26743-26724 |
| LE-2 | GCCGGTCGCGTGCGACGCCCAAGGC [SEQ ID NO: 60] | 25 | 33130-33106 |
| SG-3 | CCGACGCGTGGGTATCTAGGGGGTCG [SEQ ID NO: 61] | 26 | 90559-90534 |
| SG-4 | CGGGACGGCGAGCGGAAAGTCAACGT [SEQ ID N0: 62] | 26 | 86194-86169 |

TABLE 6

BLOCKER PROBES FOR HSV-2

| Probe Name | Sequence | Size (bp) | Capture Probe to which it hybridizes |
|---|---|---|---|
| HX-4 | GGCGCGGGC [SEQ ID NO: 63] | 9 | NF-1 |
| HX-5 | GAAAGTAGTGCTGGC [SEQ ID NO: 64] | 15 | NF-1 |
| GP-7 | TGCTGGCGGCG [SEQ ID NO: 65] | 11 | NF-1 |
| AZ-3 | ACACCTCCCAACG [SEQ ID NO: 66] | 13 | FG-1 |
| AZ-4 | CTCCAGGATGACG [SEQ ID NO: 67] | 13 | FG-1 |
| GR-1 | TCGGTTTGGTC [SEQ ID NO: 68] | 12 | LE-3 |
| GR-2 | ACACAGAACCTCA [SEQ ID NO: 69] | 13 | LE-3 |
| GP-8 | CACACACCTCCCA [SEQ ID NO: 70] | 13 | NF-2 |
| BR-10 | CGACCCCCTAGATA [SEQ ID NO: 71] | 14 | SG-3 |
| BR-11 | CCACGCGTCGG [SEQ ID NO: 72] | 11 | SG-3 |
| HX-6 | ACGTTGACTTTCCGC [SEQ ID NO: 73] | 15 | SG-4 |
| BR-15 | CGCCGTCCCG [SEQ ID NO: 74] | 10 | SG-4 |

TABLE 7

CAPTURE SEQUENCE PROBES FOR HPV

| Probe | Sequence | Size (bp) | HPV Type and Sequence Location |
|---|---|---|---|
| ZL-1 | GTACAGATGGTACCGGGGTTGTAGAAGTATCTG [SEQ ID NO: 75] | 33 | HPV16 5360-5392 |
| ZL-4 | CTGCAACAAGACATACATCGACCGGTCCACC [SEQ ID NO: 76] | 31 | HPV16 495-525 |
| DP-1 | GAAGTAG0TGAGGCTGCATGTGAAGTGGTAG [SEQ ID NO: 77] | 31 | HPV16 5285-5315 |
| DP-4 | CAGCTCTGTGCATAACTGTGGTAACTTTCTGGG [SEQ ID NO: 78] | 33 | HPV16 128-160 |
| SWI | GAGGTCTTCTCCAACATGCTATGCAACGTCCTG [SEQ ID NO: 79] | 33 | HPV31 505-537 |
| SH-4 | GTGTAGGTGCATGCTCTATAGGTACATCAGGCC [SEQ ID NO: 80] | 33 | HPV31 5387-5419 |
| VS-1 | CAATGCCGAGCTTAGTTCATGCAATTTCCGAGG [SEQ ID NO: 81] | 33 | HPV31 132-164 |
| VS-4 | GAAGTAGTAGTTGCAGACGCCCCTAAAGGTTGC [SEQ ID NO: 82] | 33 | HPV31 5175-5207 |
| AH-1 | GAACGCGATGGTACAGGCACTGCAGGGTCC [SEQ ID NO: 83] | 30 | HPV18 5308-5337 |

TABLE 7-continued

CAPTURE SEQUENCE PROBES FOR HPV

| Probe | Sequence | Size (bp) | HPV Type and Sequence Location |
|---|---|---|---|
| AH-2 | GAACGCGATGGTACAGGCACTGCA [SEQ ID NO: 84] | 24 | HPV18 5314-5337 |
| AL-1 | ACGCCCACCCAATGOAATGTACCC [SEQ ID NO: 85] | 24 | HPV18 4451-4474 |
| PA-4 | TCTGCGTCGTTGGAGTCGTTCCTGTCGTGCTC [SEQ ID NO: 86] | 32 | HPV18 535-566 |
| 18-1AB | (TTATTATTA)CTACATACATTGCCGCCATGTTCGCCA [SEQ ID NO: 87] | 36 | HPV18 1369-1395 |
| 18-2AB | (TTATTATTA)TGTTGCCCTCTGTGCCCCCGTTGTCTATAGCCTCCGT [SEQ ID NO: 88] | 46 | HPV18 1406-1442 |
| 18-3AB | (TTATTATTA)GGAGCAGTGCCCAAAAGATTAAAGTTTGC [SEQ ID NO: 89] | 38 | HPV18 7524-7552 |
| 18-4AB | (TTATTATTA)CACGGTGCTGGAATACGGTGAGGGGGTG [SEQ ID NO: 90] | 37 | HPV18 3485-3512 |
| 18-5AB | (TTATTATTA)ACGCCCACCCAATGGAATGTACCC [SEQ ID NO: 91] | 33 | HPV18 4451-4474 |
| 18-6AB | (TTATTATTA)ATAGTATTGTGGTGTGTTTCTCACAT [SEQ ID NO: 92] | 35 | HPV18 81-106 |
| 18-7AB | (TTATTATTA)GTTGGAGTCGTTCCTGTCGTG [SEQ ID NO: 93] | 30 | HPV18 538-558 |
| 18-8AB | (TTATTATTA)CGGAATTTCATTTTGGGGCTCT [SEQ ID NO: 94] | 31 | HPV18 634-655 |
| PE-1 | GCTCGAAGGTCGTCTGCTGAGCTTTCTACTACT [SEQ ID NO: 95] | 33 | HPV18 811-843 |
| PZ-2 | GCGCCATCCTGTAATGCACTTTTCCACAAAGC [SEQ ID NO: 96] | 32 | HPV45 77-108 |
| PZ-5 | TAGTGCTAGGTGTAGTGGACGCAGGAGGTGG [SEQ ID NO: 97] | 31 | HPV45 5295-5325 |
| CS-1 | GGTCACAACATGTATTACACTGCCCTCGGTAC (SEQ ID NO: 98] | 32 | HPV45 500-531 |
| CS-4 | CCTACGTCTGCGAAGTTTCTTGCCGTGCC [SEQ ID NO: 99] | 31 | HPV45 533-563 |
| PF-1 | CTGCATTGTCACTACTATCCCCACCACTATTTG [SEQ ID NO: 100] | 34 | HPV45 1406-1439 |
| PF-4 | CCACAAGGCACATTCATACATACACGCACGCA [SEQ ID NO: 101] | 32 | HPV45 7243-7274 |
| PA-1 | GTTCTAAGGTCCTCTGCCGAGCTCTCTACTGTA [SEQ ID NO: 102] | 33 | HPV45 811-843 |
| 45-5AB | (TTATTATTA)TGCGGTTTTGGGGGTCGACGTGGAGGC [SEQ ID NO: 103] | 36 | HPV45 3444-3470 |
| 45-6AB | (TTATTATTA)AGACCTGCCCCCTAAGGGTACATAGCC [SEQ ID NO: 104] | 36 | HPV45 4443-4469 |
| 45-8AB | (TTATTATTA)CAGCATTGCAGCCTTTTTGTTACTTGCTTGTAATAGCTCC [SEQ ID NO: 105] | 49 | HPV45 1477-1516 |

TABLE 7-continued

CAPTURE SEQUENCE PROBES FOR HPV

| Probe | Sequence | Size (bp) | HPV Type and Sequence Location |
|---|---|---|---|
| 45-9AB | (TTATTATTA)ATCCTGTAATGCACTTTTCCACAAA [SEQ ID NO: 106] | 34 | HPV45 79-103 |
| 45-10AB | (TTATTATTA)GCCTGGTCACAACATGTATTAC [SEQ ID NO: 107] | 31 | HPV45 514-535 |
| 45-11AB | (TTATTATTA)CAGGATCTAATTCATTCTGAGGTT [SEQ ID NO: 108] | 33 | HPV45 633-656 |
| ON-1 | TGCGGTTTTGGGGGTCGACGTGGAGGC [SEQ ID NO: 109] | 27 | HPV45 3444-3470 |

\* Sequences in parentheses are "tail" sequences not directed at HSV.

TABLE 8

BLOCKER PROBES FOR HPV

| Probe | Sequence | Size (bp) | Capture Probe to which it hybridizes |
|---|---|---|---|
| PV-FD-1 | GCCTCCACGTCGAC [SEQ ID NO: 110] | 14 | ON-1/45-5AB |
| PV-FD-2 | CCCCAAAACCG [SEQ ID NO: 111] | 11 | ON-1/45-5AB |
| PV-FD-3 | GGTACATTCCATTGGG [SEQ ID NO: 112] | 16 | 18-5AB/AL-1 |
| PV-FD-4 | TGGGCGTTAATAATAA [SEQ ID NO: 113] | 16 | 18-5AB |
| AH-3 | ACCATCGCGTTC [SEQ ID NO: 114] | 12 | AH-2 |
| AH-4 | GGACCCTGCAGTGC [SEQ ID NO: 115] | 14 | AH-1 |
| AH-5 | CTGTACCATCGCGTT 3' [SEQ ID NO: 116] | 15 | AH-1 |
| AH-6 | TGCAGTGCCTGT [SEQ ID NO: 117] | 12 | AH-2 |
| PZ-1 | CCACCTCCTGCGT [SEQ ID NO: 118] | 13 | PZ-5 |
| PZ-3 | ATTACAGGATGGCGC [SEQ ID NO: 119] | 15 | PZ-2 |
| PZ-4 | GCTTTGTGGAAAAGTG [SEQ ID NO: 120] | 16 | P1-2 |
| PZ-6 | CCACTACACCTAGCACTA [SEQ ID NO: 121] | 18 | PZ-5 |
| ZL-2 | CAGATACITCTACAACC [SEQ ID NO: 122] | 17 | ZL-1 |
| ZL-3 | CCGGTACCATCTGTAC [SEQ ID NO: 123] | 16 | ZL-1 |
| ZL-5 | GGTGGACCGGTCG [SEQ ID NO: 124] | 13 | ZL-4 |
| ZL-6 | ATGTATGTCTTGTTGCAG [SEQ ID NO: 125] | 18 | ZL-4 |
| DP-2 | CTACCACTTCACATGC [SEQ ID NO: 126] | 16 | DP-1 |
| DP-3 | AGCCTCACCTTACTTC [SEQ ID NO: 127] | 15 | DP-1 |
| DP-5 | CCCAGAAAGTTACCAC [SEQ ID NO: 128] | 16 | DP-4 |
| DP-6 | AGTTATGCACAGAGCT [SEQ ID NO: 129] | 16 | DP-4 |
| SH-2 | CAGGACGTTGCATAGC [SEQ ID NO: 130] | 16 | SH-1 |
| SH-3 | ATGTTGGAGAAGACCTC [SEQ ID NO: 131] | 17 | SH-1 |
| SH-5 | GGCCTGATGTACCTATA [SEQ ID NO: 132] | 17 | SH-4 |
| SH-6 | GAGCATGCACCTACAC [SEQ ID NO: 133] | 16 | SH-4 |
| VS-2 | CTCGGAAATTGCATG [SEQ ID NO: 134] | 15 | VS-1 |
| VS-3 | AACTAAGCTCGGCATT [SEQ ID NO: 135] | 16 | VS-1 |
| VS-5 | GCAACCTTTAGGGG [SEQ ID NO: 136] | 14 | VS-4 |
| VS-6 | CGTCTGCAACTACTACTTC [SEQ ID NO: 137] | 19 | VS-4 |
| CS-2 | GTACCGAGGGCAGT [SEQ ID NO: 138] | 14 | CS-1 |
| CS-3 | GTAATACATGTTGTGACC [SEQ ID NO: 139] | 18 | CS-1 |
| CS-5 | GGCACGGCAAGAAA [SEQ ID NO: 140] | 14 | CS-4 |
| CS-6 | GACTTCGCAGACGTAGG [SEQ ID NO: 141] | 17 | CS-4 |
| PF-2 | CAAAGTAGTGGTGGG [SEQ ID NO: 142] | 15 | PF-1 |

TABLE 8-continued

BLOCKER PROBES FOR HPV

| Probe | Sequence | Size (bp) | Capture Probe to which it hybridizes |
|---|---|---|---|
| PF-3 | GATAGTAGTGACAATGCAG [SEQ ID NO: 143] | 19 | PF-1 |
| PF-5 | TGCGTGCGTGTATGTA [SEQ ID NO: 144] | 16 | PF-4 |
| PF-6 | TGAATGTGCCTTGTGG [SEQ ID NO: 145] | 16 | PF-4 |
| PE-2 | AGTAGTAGAAAGCTCAGC [SEQ ID NO: 146] | 18 | PE-1 |
| PE-3 | AGACGACCTTCGAGC [SEQ ID NO: 147] | 15 | PE-1 |
| PA-2 | TACAGTAGAGAGCTCOG [SEQ ID NO: 148] | 17 | PA-1 |
| PA-3 | CAGAGGACCTTAGAAC [SEQ ID NO: 149] | 16 | PA-1 |
| PA-5 | GAGCACGACAGGAACG [SEQ ID NO: 150] | 16 | PA-4 |
| PA-6 | ACTCCAACGACGCAGA [SEQ ID NO: 151] | 16 | PA-4 |

EXAMPLE 3

Effect of the Extent of Biotin Labeling on Capture Efficiency

Tests were conducted to determine the optimal number of biotin labels per capture sequence probe for TSHC detection. The general TSHC method described in Example 1 was employed. The capture efficiency of capture sequence probe F15R labeled with one, two, or three biotins, measured by signal to noise ratio (S/N), were tested. The signal sequence probe employed was H19. As shown in Table 9, two biotins per capture sequence probe were sufficient for optimal capture efficiency. Greater than a 50% increase in S/N was observed using capture sequence probe with two biotin labels compared to the single biotin labeled capture sequence probe. The addition of a third biotin label to the capture sequence probe resulted in a decrease in S/N relative to the two-biotin labeled capture sequence probe.

TABLE 9

EFFECT OF THE EXTENT OF BIOTIN LABELING ON CAPTURE EFFICIENCY

| # Biotins | HSV-1/well | RLU | CV | S/N |
|---|---|---|---|---|
| One | 0 | 54 | 3% | 1.0 |
| One | $4.5 \times 10^3$ | 236 | 2% | 4.4 |
| One | $4.5 \times 10^4$ | 1861 | 3% | 34.5 |
| One | $4.5 \times 10^5$ | 15633 | 7% | 289.5 |
| Two | 0 | 46 | 3% | 1.0 |
| Two | $4.5 \times 10^3$ | 296 | 10% | 6.4 |
| Two | $4.5 \times 10^4$ | 2558 | 1% | 55.6 |
| Two | $4.5 \times 10^5$ | 23369 | 4% | 508.0 |
| Three | 0 | 44 | 22% | 1.0 |
| Three | $4.5 \times 10^3$ | 243 | 6% | 5.5 |
| Three | $4.5 \times 10^4$ | 1820 | 2% | 51.4 |
| Three | $4.5 \times 10^5$ | 18581 | 8% | 422.3 |

EXAMPLE 4

Effect of the Distance Between the CSP and the SSP Target Sites on Capture Efficiency The effect of the distance between capture sequence probe (CSP) and signal sequence probe (SSP) hybridization sites on a HSV-1 target nucleic acid on capture efficiency was evaluated. CSPs that hybridize to HSV-1 nucleic acid sequences which are located 0.2 kb, 3 kb, 18 kb, 36 kb and 46 kb from the site of SSP hybridization were tested. The general TSHC method described in Example 1 was employed. The capture efficiencies were 100%, 50%, 30%, 19% and 7%, respectively (Table 10). A steady decline in relative capture efficiencies was observed as the distance increased from 0.2 Kb to 46 Kb.

TABLE 10

EFFECT OF DISTANCE BETWEEN TARGET SITES ON CAPTURE EFFICIENCY

| CSP | SSP | Distance Between Target Site | Relative Capture Efficiency |
|---|---|---|---|
| BRH19 | H19 | 0.2 Kb | 100% |
| F15R | H19 | 3 Kb | 50% |
| F6R | RH5B | 18 Kb | 30% |
| F15R | RH5B | 36 Kb | 19% |
| F6R | H19 | 46 Kb | 7% |

EXAMPLE 5

Effect of Fused Capture Sequence Probe on TSHC Detection of HSV-1

The binding capacity of streptavidin plates was determined to be approximately 2 pmoles of doubly-biotinylated CSPs per well. Since the CSPs are doubly biotin-labeled, a maximum of 8 CSPs (2 CSPs per SSP) is preferred in order not to exceed the binding capacity of the wells. Any increase in biotin-labeled capture sequence probe above the stated capacity resulted in a decrease in signal, the so-called "hook effect." In order to avoid this "hook effect" and still permit the use of greater than four SSP-CSP combinations, the effect of synthesizing oligonucleotides that contained the sequences of two CSPs fused together (5' and 3' sites) was tested. The fused capture sequence probes may function independently to drive hybridization to the unique target sites. In another embodiment, the fused probes may bind to two target sites with the second hybridization favored, since it is essentially a uni-molecular reaction with zero order kinetics once the probe has hybridized to the first site. The hybridization may be determined by one or both mechanisms. Previous experiments showed that two CSPs, VH3, and NC-1, when used together, gave approximately twice the S/N as the individual CSPs. Unfused capture sequence probes VH-3 and NC-1 were used at 2.5 pmoles/ml each for a total concentration of 5 pmoles/ml, fused probe VH-4 (fusion of VH-3 and NC-1) was used at 2.5 pmole/ml. As shown in Table 11, the fused probe was as effective as the combination of the two unfused probes. Therefore, TSHC detection using fused capture sequence probes permits the number of nucleic acid sequences targeted by the signal sequence probe to be at least doubled without exceeding the plate biotin-binding capacity. The experiment also demonstrates the lack of cross-reactivity of HSV-2 at $10^7$ genomes as shown by the S/N less than 2.0.

TABLE 11

COMPARISON OF FUSED VERSUS UNFUSED CAPTURE
SEQUENCE PROBES IN TSHC DETECTION OF HSV-1

| SSP | CSP | Viral Particles/ml | RLU | CV | S/N |
|---|---|---|---|---|---|
| RH5B | VH-3, NC-1 | 0 | 94 | 14% | 1.0 |
| RH5B | VH-3, NC-1 | $10^4$ HSV-1 | 164 | 5% | 1.7 |
| RH5B | VH-3, NC-1 | $10^5$ HSV-1 | 1003 | 4% | 10.7 |
| RH5B | VH-3, NC-1 | $10^7$ HSV-2 | 125 | 6% | 1.3 |
| RH5B | VH-4 (fused) | 0 | 97 | 10% | 1.0 |
| RH5B | VH-4 (fused) | $10^4$ HSV-1 | 181 | 3% | 1.9 |
| RH5B | VH-4 (fused) | $10^5$ HSV-1 | 1070 | 2% | 11.0 |
| RH5B | VH-4 (fused) | $10^7$ HSV-2 | 140 | 5% | 1.4 |

EXAMPLE 6

Capture Efficiency of Various CSPs and SSPs in TSHC Detection of HSV-1

The capture efficiency of capture sequence probes (CSPs) for each of the four HSV-1 specific signal sequence probes (SSPs), H19, RH5B, RH3 and R10, in the detection of HSV-1 by TSHC was evaluated. The criteria used for designing the capture sequence probes were: 1) the CSP hybridization site is within 1 kb either 5' or 3' of the SSP hybridization site on the HSV-1 nucleic acid sequence, preferably within 0.5 kb; and 2) the CSPs contain sequences that are unique to HSV-1, with no stretches of sequence homology to HSV-2 greater than 10 bases. The CSPs were designed to target the 5' and 3' regions adjacent to the SSP hybridization site, preferably with a 5' CSP and a 3' CSP for each SSP. The Omiga software (Oxford Molecular Group, Campbell, Calif.) was instrumental in the identification of such sites. The melting temperature (Tm) of the CSPs was designed to be between 70° C. to 85° C., to conform to the 70° C. to 75° C. hybridization temperature used in Hybrid Capture II (HCII) assay for HSV (Digene). The general TSHC method described in Example 1 was employed. Eleven CSPs (which bind to 6 different sites) for H19, six CSPs (which bind to three unique sites) for RH5B, six CSPs (which bind to six unique sites) for RH3, and two CSPs for R10 were tested, As shown in Table 12, efficient capture sequence probes were found for signal sequence probes H19, RH5B and R10.

TABLE 12

CSPs AND SSPs FOR TSHC DETECTION OF HSV-1

| SSP | CSP | Cap % | SSP | CSP | Cap % | SSP | CSP | Cap % |
|---|---|---|---|---|---|---|---|---|
| R10 | ON-3 | 100% | RH5B | TS-1 | 50% | H19 | HZ-1 | 50% |
| R10 | ON-3 | 80% | RH5B | NC-1 | 75% | H19 | HZ-2 | 20% |
| | | | RH5B | VH-4 | 130% | H19 | ZD-1 | 40% |
| | | | RH5B | TS-2 | 25% | H19 | ZD-2 | 20% |
| | | | RH5B | VH-3 | 50% | H19 | BRH19 | 70% |
| | | | | | | H19 | VH-2 | 70% |
| | | | | | | H19 | F15R | 25% |

EXAMPLE 7

Capture Efficiency of Various CSPs and SSPs in TSHC Detection of HSV-2

The capture efficiency of capture sequence probes (CSPs) for each of the four HSV-2 specific signal sequence probes (SSPs), E4A, E4B, Ei8, and i8, in the detection of HSV-2 by TSHC were evaluated. HSV-2 specific capture sequence probes (CSPs) were designed based on the same criteria as the HSV-1 CSPs except for the requirement that they be HSV-2 specific. Four CSPs for E4A, three CSPs for E4B, and two CSPs each for Ei8 and i8 were tested. The general TSHC method described in Example 1 was employed. As shown in Table 13, efficient capture sequence probes were found for i8 and Ei8.

TABLE 13

CSPs AND SSPs FOR TSHC DETECTION OF HSV-2

| SSP | CSP | Cap % | SSP | CSP | Cap % |
|---|---|---|---|---|---|
| i8 | NF-1 | 100% | Ei8 | NF-2 | 50% |
| | | | Ei8 | LE-3 | 45% |

EXAMPLE 8

Effect of Blocker Probes on HSV-1 and HSV-2 Detection

In an attempt to reduce cross-reactivity of TSHC while allowing the capture step to take place at room temperature, methods using blocker probes were developed. Blocker probes comprise sequences that are complementary to the capture sequence probes (CSPs) used for detection. These experiments were designed to prevent non-specific hybridization of the CSPs to non-targeted nucleic acids present in the sample under the lower stringency conditions, a situation often encountered during the room temperature capture step.

In one method, blacker probes that are complementary to the full length or nearly the full length of the capture sequences probe were used. The blocker probes were added to the reaction mixture in 10-fold excess relative to the CSP after hybridization of the CSP and the SSP to the target DNA molecule has occurred. Since the blocker probes have similar melting temperature as the CSPs, the CSPs were hybridized to the target nucleic acids first to prevent hybridization of the blocker probes to the CSPs before the hybridization of the CSPs to the target nucleic acids occurred. As shown in Table 14, the addition of the blocker probes resulted in a dramatic reduction in cross-reactivity while these probes had no effect on the sensitivity of HSV-1 detection. The S/N for the detection of cross-reactive HSV-2 ($10^7$ viral particles/ml) decreased from 5.0 to 0.8 when the blocker probes were used.

In another method, blocker probes that are complementary to only a portion of the CSPs and are shorter than the CSPs were used. The blocker probes were designed to have melting temperatures above room temperature but at least 10° C. below the hybridization temperature of CSPs to the target nucleic acids. Since these blocker probes hybridize to the CSPs at temperature below the CSP hybridization temperature to the target nucleic acids, the blocker probes may be added to the reaction at the same time as the CSP and SSP without effecting the hybridization efficiency of the CSPs to the target nucleic acid. These shorter blocker probes function during the room temperature capture step by hybridizing to the CSPs at the lower temperatures that are encountered during the room temperature capture step. As shown in Table 15, the addition of either single or paired shorter blocker probes in 100-fold excess relative to the CSPs resulted in a dramatic reduction in cross-reactivity but had no effect on sensitivity of HSV-1 detection. The S/N for detecting cross-reactive HSV-2

($10^7$ viral particles/ml) without the blocker probes was 10.6, but was reduced to less than or equal to 1.5 with the addition of the blocker probes.

Therefore, both methods utilizing blocker probes provide a substantial reduction in cross-reactivity. The second method utilizing blocker probes with lower melting temperature may be preferred because the addition of blocker probes at the same time as the capture sequence probe eliminates the need for an extra step for the detection method.

TABLE 14

EFFECT OF BLOCKER PROBES ADDED POST CAPTURE PROBE HYBRIDIZATION ON TSHC

| SSP | CSP | 100x Blocker Probe | Viral Particles/ml | RLU | CV | S/N |
|---|---|---|---|---|---|---|
| H19 | HZ-1 | None | 0 | 66 | 7% | 1.0 |
| H19 | HZ-1 | None | $10^5$ HSV-1 | 246 | 5% | 3.7 |
| H19 | HZ-1 | None | $10^6$ HSV-1 | 1998 | 2% | 30.3 |
| H19 | HZ-1 | None | $10^7$ HSV-2 | 327 | 2% | 5.0 |
| H19 | HZ-1 | ZD-3 | 0 | 60 | 3% | 1.0 |
| H19 | HZ-1 | ZD-3 | $10^5$ HSV-1 | 267 | 4% | 4.5 |
| H19 | HZ-1 | ZD-3 | $10^6$ HSV-1 | 2316 | 6% | 38.6 |
| H19 | HZ-1 | ZD-3 | $10^7$ HSV-2 | 49 | 2% | 0.8 |

TABLE 15

EFFECT OF BLOCKER PROBES ADDED SIMULTANEOUSLY WITH THE CAPTURE PROBES UPON TSHC DETECTION OF HSV-1

| SSP | CSP | 10x Blocker Probe | Viral Particle/ml | RLU | CV | S/N |
|---|---|---|---|---|---|---|
| H19 | HZ-1 | none | 0 | 38 | 15% | 1.0 |
| H19 | HZ-1 | none | $10^4$ HSV-1 | 71 | 2% | 1.9 |
| H19 | HZ-1 | none | $10^5$ HSV-1 | 389 | 12% | 10.2 |
| H19 | HZ-1 | none | $10^7$ HSV-2 | 401 | 18% | 10.6 |
| H19 | HZ-1 | NG-4 | 0 | 39 | 8% | 1.0 |
| H19 | HZ-1 | NG-4 | $10^4$ HSV-1 | 82 | 5% | 2.1 |
| H19 | HZ-1 | NG-4 | $10^5$ HSV-1 | 411 | 18% | 10.5 |
| H19 | HZ-1 | NG-4 | $10^7$ HSV-2 | 57 | 15% | 1.5 |
| H19 | HZ-1 | EA-1, EA-2 | 0 | 37 | 0% | 1.0 |
| H19 | HZ-1 | EA-1, EA-2 | $10^4$ HSV-1 | 75 | 8% | 2.0 |
| H19 | HZ-1 | EA-1, EA-2 | $10^5$ HSV-1 | 419 | 8% | 11.3 |
| H19 | HZ-1 | EA-1, EA-2 | $10^7$ HSV-2 | 49 | 5% | 1.3 |
| H19 | HZ-1 | NG-7, NG-8 | 0 | 42 | 10% | 1.0 |
| H19 | HZ-1 | NG-7, NG-8 | $10^4$ HSV-1 | 76 | 3% | 1.8 |
| H19 | HZ-1 | NG-7, NG-8 | $10^5$ HSV-1 | 471 | 5% | 11.2 |
| H19 | HZ-1 | NG-7, NG-8 | $10^7$ HSV-2 | 47 | 9% | 1.1 |

EXAMPLE 9

TSHC Detection Reduces Vector Background

The TSHC assay eliminates the vector contamination problem often associated with the Hybrid Capture II (HC II) detection assay (Digene). As the RNA signal sequence probes used in HC II are generated from linearized vector templates, any remaining unlinearized plasmid DNA results in the production of additional RNA probe sequences specific for vector sequences. In the HC II assay, the RNA/DNA hybrids that form as a result of these read-through transcripts are captured on the antibody coated plates and generate signal. In contrast, in the TSHC method, only those RNA/DNA hybrids that also hybridize to the capture sequence probes are detected. Accordingly, any detection of vector-related sequences is eliminated. Plasmids SK+, pBR322, DgZ, and 1066 which were known to be detectable in HSV HC II test (Digene) were tested in the TSHC assay using two RNA signal sequence probes (H19 and RH5b) and two capture sequence probes (VH-2 and VH-4). Identical sets of RNA probes were then used in the HC II method and the TSHC method for the detection of HSV-1. The general TSHC method described in Example 1 was employed. As shown in Table 16, while signal to noise ratio in standard HC II ranged from 14 to 48, the signal to noise ratio for the TSHC method was less than 2 for all plasmids tested.

TABLE 16

VECTOR BACKGROUND IN TSHC V. HCII DETECTION

| Method | SSP | CSP | Targets/ml | RLU | CV | S/N |
|---|---|---|---|---|---|---|
| TSHC | H19 + RH5B | VH-2 + VH-4 | 0 | 94 | 6% | 1.0 |
| TSHC | H19 + RH5B | VH-2 + VH-4 | 4 ng pBS SK+ | 137 | 7% | 1.5 |
| TSHC | H19 + RH5B | VH-2 + VH-4 | 2 ng pBR322 | 99 | 6% | 1.1 |
| TSHC | H19 + RH5B | VH-2 + VH-4 | 4 ng DgX | 135 | 7% | 1.4 |
| TSHC | H19 + RH5B | VH-2 + VH-4 | 4 ng 1066 | 107 | 7% | 1.1 |
| HC II | H19 + RH5B | None | 0 | 94 | 9% | 1.0 |
| HC II | H19 + RH5B | None | 4 ng pBS SK+ | 4498 | 3% | 48.1 |
| HC II | H19 + RH5B | None | 2 ng pBR322 | 1281 | 8% | 13.7 |
| HC II | H19 + RH5B | None | 4 ng DgX | 2003 | 5% | 21.4 |
| HC II | H19 + RH5B | None | 4 ng 1066 | 1536 | 2% | 16.4 |

EXAMPLE 10

Sensitivity and Specificity of Detecting HSV-1 and HSV-2 by TSHC

Figure 4:
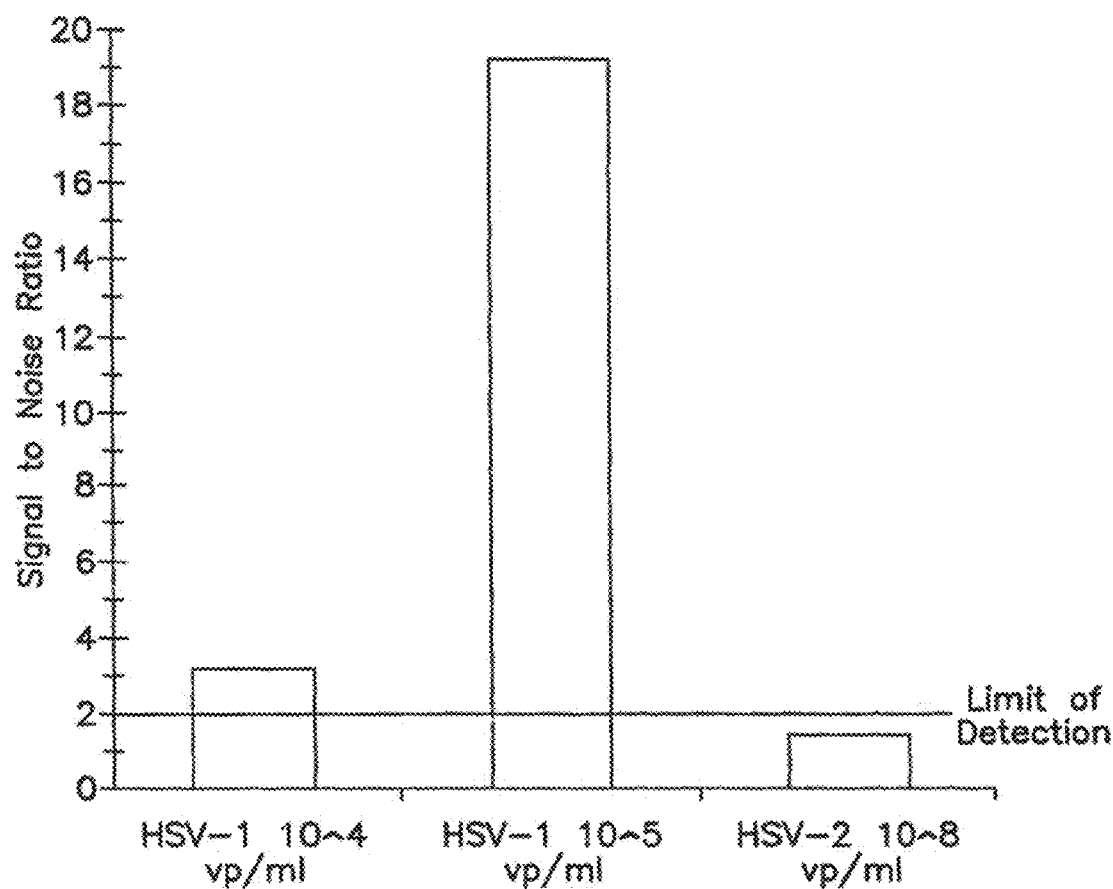
FIG. 4 shows the analytical sensitivity and specificity of target-specific hybrid capture detection of HSV-1.
Figure 5:
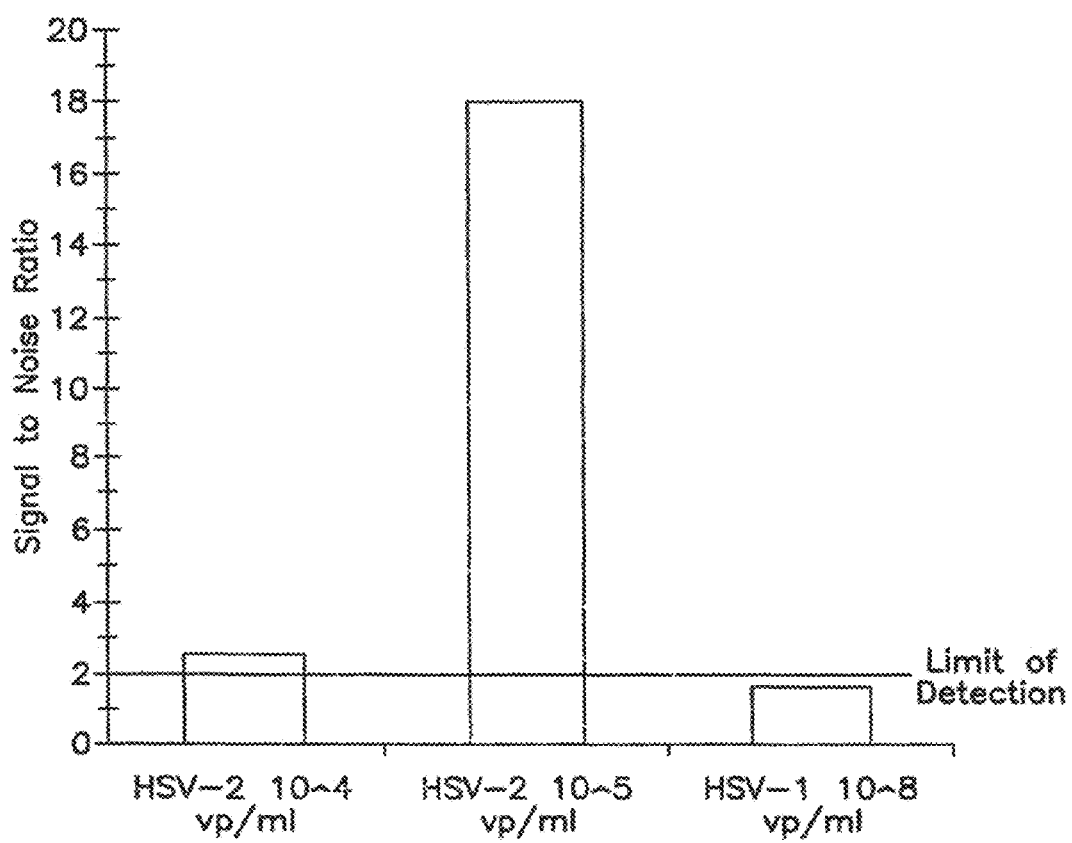
FIG. 5 shows the analytical sensitivity and specificity of target-specific hybrid capture detection of HSV-2.

The sensitivity and typing discrimination for the TSHC detection of HSV-1 and HSV-2 were assessed using the TSHC described in Example 1. In the HSV-1 TSHC assay, signal sequence probes H19 and RH5B, capture sequence probes HZ-1, VH-2 and VH-4, and blocker probes NG-7, NO-8, GP-3, GP-4, and GP-1 were used. In the HSV-2 TSHC assay, signal sequence probes i8 and Ei8, capture sequence probes NF-1 and NF-2, and blocker probes HX-4, HX-5 and GP-8 were used. HSV-1 and HSV-2 viral particles were diluted to various concentrations using the Negative Control Solution. As shown in FIGS. 4 and 5, while $10^4$ copies of the either HSV-1 or HSV-2 (450 copies/well) were detected in the respective assays, there was virtually no detection of the cross-reactive type HSV at concentrations up to and including $10^8$ copies/ml (4,500,000 copies/well). Thus, the HSV-1 and HSV-2 TSHC assays can distinguish the two HSV types at a greater than 10,000-fold range of discrimination while maintaining excellent sensitivity (450 VP/well).

The HSV-1 TSHC assay shows a linear range of detection ranging from at least $2 \times 10^3$ to $5 \times 10^3$ VP/ml (Table 17). The specificity of the assay is excellent as no cross-reactivity was detected (S/N is less than or equal to 2) in samples containing HSV-2 at a concentration as high as $2 \times 10^7$ to $5 \times 10^7$ viral particles/ml. Similarly, the HSV-2 TSHC assay also shows excellent specificity, wherein no cross-reactivity was detected in samples containing HSV-1 at a concentration as high as $5 \times 10^7$ viral particles/ml (Table 18). Similar results were obtained from TSHC detection of HSV-2 using a dilution series of HSV-2 and HSV-1 viruses (Table 19).

TABLE 17

ANALYTICAL SENSITIVITY AND SPECIFICITY
OF THE HSV1 TSHC ASSAY

| Targets | RLU | S/N |
|---|---|---|
| Negative Control | 47 | 1.0 |
| HSV2 @ 5 × 10$^7$ VP/ml | 57 | 1.2 |
| HSV2 @ 2 × 10$^7$ VP/ml | 43 | 0.9 |
| HSV1 @ 5 × 10$^3$ VP/ml | 201 | 4.3 |
| HSV1 @ 2 × 10$^3$ VP/ml | 107 | 2.3 |

TABLE 18

ANALYTICAL SENSITIVITY AND SPECIFICITY
FOF THE HSV2 TSHC ASSAY

| Targets | RLU | S/N |
|---|---|---|
| Negative Control | 40 | 1.0 |
| HSV1 @ 5 × 10$^7$ VP/ml | 78 | 2.0 |
| HSV1 @ 2 × 10$^7$ VP/ml | 55 | 1.4 |
| HSV2 @ 5 × 10$^3$ VP/ml | 218 | 5.5 |
| HSV2 @ 2 × 10$^3$ VP/ml | 106 | 2.7 |

TABLE 19

DETECTION WITH HSV-2 PROBES USING HSV-1
AND HSV-2 OF DIFFERENT DILUTION

| Targets | RLU | S/N |
|---|---|---|
| Negative Control | 43 | 1.0 |
| HSV1 @ 5 × 10$^7$ VP/ml | 112 | 2.6 |
| HSV1 @ 2 × 10$^7$ VP/ml | 57 | 1.3 |
| HSV1 @ 1 × 10$^7$ VP/ml | 38 | 0.9 |
| HSV1 @ 1 × 10$^6$ VP/ml | 38 | 0.9 |
| HSV1 @ 1 × 10$^5$ VP/ml | 33 | 0.8 |
| HSV1 @ 1 × 10$^4$ VP/ml | 52 | 1.2 |
| HSV1 @ 1 × 10$^3$ VP/ml | 43 | 1.0 |
| HSV1 @ 1 × 10$^2$ VP/ml | 39 | 0.9 |
| HSV2 @ 1 × 10$^7$ VP/ml | 257173 | 5980.8 |
| HSV2 @ 1 × 10$^6$ VP/ml | 28544 | 663.8 |
| HSV2 @ 1 × 10$^5$ VP/ml | 3200 | 74.4 |
| HSV2 @ 1 × 10$^4$ VP/ml | 266 | 6.2 |
| HSV2 @ 5 × 10$^3$ VP/ml | 181 | 4.2 |
| HSV2 @ 1 × 10$^3$ VP/ml | 62 | 1.4 |
| HSV2 @ 1 × 10$^2$ VP/ml | 44 | 1.0 |

EXAMPLE 11

Clinical Specimen Testing

A 64-member clinical specimen panel was tested for HSV-1 and HSV-2 using both TSHC and HCII methods. The panel included 15 samples containing known quantities of HSV-1 or HSV-2, and 49 samples known to be negative for HSV-1 and HSV-2 by PCR testing. Accordingly, the 15 positive samples were "Expected" to test positive in both the HCII and TSHC assays, and the 49 negative samples were "Expected" to test negative in both the HCII and TSHC tests. The general TSHC method described in Example 1 was employed. The results using the HCII method and the TSHC method are shown in Tables 20 and 21, respectively. Of the 49 samples "Expected" to yield negative result, 5 samples tested positive and 44 samples tested positive using the HCII method. In comparison, all 49 samples tested negative using the TSHC method. Therefore, the TSHC method is superior in specificity to the Hal method in the detection of HSV-1 and HSV-2.

TABLE 20

OBSERVED VERSUS EXPECTED RESULTS FOR
HCII DETECTION OF HSV1 AND HSV2

| HCII Result | Expected Result Positive | Expected Result Negative |
|---|---|---|
| Positive | 15 | 5 |
| Negative | 0 | 44 |
| Total | 15 | 49 |

TABLE 21

OBSERVED VS. EXPECTED RESULTS FOR
TSHC DETECTION OF HSV1 AND HSV2

| TSHC Result | Expected Result Positive | Expected Result Negative |
|---|---|---|
| Positive | 14 | 0 |
| Negative | 1 | 49 |
| Total | 15 | 49 |

EXAMPLE 12

Effect of Combining Probes in TSHC Detection of HSV

The effect of combining HSV-1 specific signal sequence probe and capture sequence probe sets on HSV-1 detection was assessed. TSHC detection of HSV-1 and HSV-2 cross-reactivity was performed separately with two different sets of RNA signal sequence probe/biotinylated capture sequence probe combinations (Set #1: H19 plus HZ-1; and Set #2: RH5b plus the TS-1 and TS-2). TSHC was also performed with both RNA signal sequence probe/biotinylated capture sequence probe sets combined to assess the effect of combining the two probe sets on sensitivity and cross-reactivity. The general TSHC method described in Example 1 was employed. The results shown in Table 22 clearly demonstrate an additive effect of combining the two probe sets for HSV-1 detection with no apparent increase in HSV-2 cross-reactivity.

TABLE 22

SENSITIVITY IS IMPROVED BY COMBINING
HSV-1 SPECIFIC CSPs AND SSPs

| Capture Sequence Probes | Signal Sequence Probes | VP/ml | RLU | CV | S/N |
|---|---|---|---|---|---|
| HZ-1 | H19 | 0 | 60 | 3% | 1.0 |
| HZ-1 | H19 | 10$^5$ HSV-1 | 267 | 4% | 4.5 |
| HZ-1 | H19 | 10$^6$ HSV-1 | 2316 | 6% | 38.9 |
| HZ-1 | H19 | 10$^7$ HSV2 | 49 | 2% | 0.8 |
| TS-1, TS-2 | RH5B | 0 | 78 | 6% | 1.0 |
| TS-1, TS-2 | RH5B | 10$^5$ HSV-1 | 291 | 6% | 3.8 |
| TS-1, TS-2 | RH5B | 10$^6$ HSV-1 | 2368 | 11% | 30.6 |
| TS-1, TS-2 | RH5B | 10$^7$ HSV2 | 75 | 11% | 1.0 |
| HZ-1, TS-1, TS-2 | H19, RH5B | 0 | 70 | 12% | 1.0 |
| HZ-1, TS-1, TS-2 | H19, RH5B | 10$^5$ HSV-1 | 457 | 10% | 6.5 |
| HZ-1, TS-1, TS-2 | H19, RH5B | 10$^6$ HSV-1 | 4263 | 1% | 60.9 |
| HZ-1, TS-1, TS-2 | H19, RH5B | 10$^7$ HSV2 | 67 | 6% | 1.0 |

EXAMPLE 13

TSHC Detection of HPV18 and HPV45

The relative sensitivity and specificity of TSHC and HCII detection of Human Papillomavirus 18 (HPV18) and Human Papillomavirus 45 (HPV45) was compared. Previous studies have established HPV45 as the most cross-reactive HPV type to HPV18, and conversely, HPV18 as the most cross-reactive HPV type to HPV45. In this study, the ability of the two methods to detect HPV 18 and HPV45 was assessed using HPV18 and HPV45 plasmid DNA.

Capture sequence probes (CSPs) for each of the four Human Papillomavirus types: HPV16, HPV18, HPV31, and HPV45, were designed. The criteria used for designing the capture sequence probes were: 1) the CSP hybridization sites do not overlap with the SSP sites; 2) the CSPs contain sequences unique to one HPV type with no stretches of sequence homology to other HPV types greater than 12 bases; and 3) the CSPs are of sufficient length so as to be capable of hybridizing efficiently at 70° C.

The blocker probes for each CSP were designed such that they could be added simultaneously with the CSP during hybridization to the target nucleic acid. The blocker probes have a melting temperature of at least 37° C. but no higher than 60° C., as calculated by the Oligo 5.0 program (National Biosciences, Inc., Plymouth, Minn.). Two blocker probes were used for each capture oligonucleotide to maximize the blocker effect during the room temperature plate capture step. It was also desired that the blocker probes for each CSP have similar melting temperatures.

CSPs for each of the HPV types were tested for relative capture efficiency and cross-reactivity to other HPV types. CSPs that provided the best combination of sensitivity and low cross-reactivity were used for the detection of HPV using TSHC.

In TSHC and HCII detection of HPV18, HPV18 DNA was used at a concentration of 10 pg/ml. HPV45, used for cross-reactivity testing, was used at 4 ng/ml. The general TSHC method described in Example 1 was employed. As shown in Table 23, a signal to noise ratio of 16.9 was obtained for TSHC detection of HPV18 compared to a ratio of 7.6 obtained for HCII detection of HPV 18. On the other band, cross-reactivity with HPV45 was significantly reduced using the TSHC method (S/N of 1.3 for TSHC compared to S/N of 393.3 for Hal). The results clearly show that compared to the HCII method, the TSHC method for the detection of HPV 18 was superior in both sensitivity and specificity. Results obtained in experiments comparing TSHC and HCII detection of HPV45 demonstrate that the TSHC method for the detection of HPV45 is superior in both sensitivity and specificity (Table 24).

TABLE 23

TSHC DETECTION OF HPV 18

| Method | Target | SSP | CSP | S/N |
|---|---|---|---|---|
| TSHC | 0 | 18L1 | 18-7L | 1.0 |
|  | HPV18 (10 pg/ml) | 18L1 | 18-7L | 16.9 |
|  | HPV45 (4 ng/ml) | 18L1 | 18-7L | 1.3 |
| HC II | 0 | 18L1 | none | 1.0 |
|  | HPV18 (10 pg/ml) | 18L1 | none | 7.6 |
|  | HPV45 (4 ng/ml) | 18L1 | none | 393.3 |

TABLE 24

TSHC DETECTION OF HPV 45

| Method | Target | SSP | CSP | S/N |
|---|---|---|---|---|
| TSHC | 0 | 45L1 | ON-1 | 1.0 |
|  | HPV45 (10 pg/ml) | 45L1 | ON-1 | 8.4 |
|  | HPV18 (4 ng/ml) | 45L1 | ON-1 | 1.6 |
| HC II | 0 | 45L1 | none | 1.0 |
|  | HPV45 (10 pg/ml) | 45L1 | none | 8.2 |
|  | HPV18 (4 ng/ml) | 45L1 | none | 494.0 |

EXAMPLE 14

Target-Specific Hybrid Capture-Plus Assay Protocol

Hepatitis B Virus (HBV) was used as the model system for the development of the target-specific hybrid capture-plus (TSHC-plus) assay for the detection of target nucleic acids.

The hybridization in the TSHC-plus method (FIG. 6A-6D) may be performed in a single step. In the one-step method, CSPs, SSPs containing pre-hybridized DNA/RNA duplex, bridge probes (FIGS. 6B-6D), and blacker probes are added simultaneously to the target nucleic acids. If hybridization is performed in two steps, CSPs, SSPs without pre-hybridized DNA/RNA duplex, bridge probes and blocker probes are first hybridized to the target nucleic acid. Oligonucleotide probes complementary to the single stranded nucleic acid sequence in the SSP are then added to the reaction to form the DNA/RNA duplexes. The hybrids are then detected using anti-RNA/DNA antibody as described in Example 1.

Experiments were carried out to detect HBV using TSHC-plus (Examples 15-18). The method shown in FIG. 6A was used Human hepatitis B virus (HBV adw2) plasmid DNA of known concentration (Digene Corp) was diluted using HBV negative Sample Diluent (Digene). Various dilutions were made and aliquoted into individual tubes. The negative Sample Diluent was used as a negative control. A half volume of the Denaturation Reagent 5100-0431 (Digene) was added to the test samples. Test samples were incubated at 65° C. for 45 minutes to denature the nucleic acids in the samples.

Following denaturation of the HBV sample, a hybridization solution containing capture sequence probes (CSPs), blocker probes, signal sequence probe comprising a M13 DNA/M13 RNA duplex, and a bridge probe of a single-stranded or partially single stranded DNA sequence capable of hybridizing to both an SSP and HBV sequences was added to the samples, and incubated at 65° C. for 1-2 hours. Alternatively, the denatured samples were incubated for 1 hour with a hybridization solution containing capture sequence probes (CSPs), blocker probes and M13 DNA plasmid containing HBV complementary sequences for 1 hour. Following the incubation, M13 RNA was added to the reaction and the incubation was continued for an additional hour at 65° C.

Tubes containing reaction mixtures were cooled at room temperature for 5 minutes and aliquots were taken from each tube and transferred to individual wells of a 96-well streptavidin plate (Digene). The plates were shaken at 1100 rpms for 1 hour at room temperature. The solution was then decanted and the plates were washed four times with SNM wash buffer (Digene). The alkaline-phosphatase anti-RNA/DNA antibody DR-I (Digene) was added to each well and incubated for 30 minutes at room temperature. The DR-1 (Digene) was then decanted and the plates were washed four times with SNM wash buffer (Digene). Following removal of the residual wash buffer, luminescent substrate (CDP-Star, Tropix Inc.)

was added to each well and incubated for 15 minutes at room temperature. Individual wells were read on a plate luminometer to obtain relative light unit (RLU) signals.

EXAMPLE 15

The following tables describe the various probes tested in the experiments described in Examples 16-18.

TABLE 25

CAPTURE SEQUENCE PROBES FOR HBV

| Probe | Sequence | Size (bp) | Location within HBV | Strand |
|---|---|---|---|---|
| HBV C1 | GCTGGATGTGTCTGCG-GCGTTT TATCAT (SEQ ID NO: 152) | 28 | 374-401 | Sense |
| HBV C2 | ACTGTTCAAGCCTC-CAAGCTGC GCCTT (SEQ ID NO: 153) | 27 | 1861-1877 | Sense |
| HBV C3 | ATGATAAAACGCCGCAGA-CACA TCCAGCGATA (SEQ ID NO: 154) | 32 | 370-401 | Antisense |

TABLE 26

HBV/M13 CLONES FROM WHICH SSPs ARE PREPARED

| Clone name | Vector | Cloning site | Insert Size (bp) | Location within HBV |
|---|---|---|---|---|
| SA1 | M13 mp 18 | Eco RI, Hind III | 35 | 194-228 |
| SA2 | M13 mp 18 | Eco RI, Hind III | 34 | 249-282 |
| SA1a | M13 mp 19 | Eco RI, Hind III | 35 | 194-228 |
| SA2a | M13 mp 19 | Eco RI, Hind III | 34 | 249-282 |
| SA4 | M13 mp 19 | Eco RI, Hind III | 87 | 1521-1607 |

TABLE 27

HBV BLOCKER PROBES

| Probe | Sequence | Size (bp) | CSP to which it hybridizes |
|---|---|---|---|
| B1 | ATGATAAAACGCCG (SEQ ID NO: 155) | 14 | HBV C1 |
| B2 | CAGACACATCCAGC (SEQ ID NO: 156) | 14 | HBV C1 |
| B3 | AAGGCACAGCTTG (SEQ ID NO: 157) | 13 | HBV C2 |
| B4 | GAGGCTTGAACAGT (SEQ ID NO: 158) | 14 | HBV C2 |
| B5 | TATCGCTGGATGTGTC (SEQ ID NO: 159) | 16 | HBV C3 |
| B6 | TCGGCGTTTATCATG (SEQ ID NO: 160) | 16 | HBV C3 |

EXAMPLE 16

Effect of Blocker Probes on TSHC-Plus Detection of HBV

During room temperature capture step, excess SSP (M13 RNA/HBV-M13 DNA duplex) non-specifically hybridizing to the CSP are immobilized onto the plate which results in high background signals. In an attempt to reduce background signal, blocker probes were employed in TSHC-Plus detection of HBV. The blocker probes were designed to be much shorter than the CSPs so that they are only capable of hybridizing to the capture probes at temperatures well below the hybridization temperatures used in the assay.

Blocker probe sets consisting of two separate oligonucleotides that are complementary to the CSPs were used. The blocker probes were added to the hybridization mixture in 10-fold excess relative to the CSPs. Since the blocker probes are much shorter than the CSPs, they do not hybridize with CSPs at the target hybridization temperature and therefore do not interfere with the hybridization of the CSPs to the target nucleic acids. Following the hybridization of CSP and target nucleic acids, the samples were subjected to a room temperature capture step during which the blocker probes hybridize with excess CSPs, thus preventing them from hybridizing to the SSPs. As shown in Table 28, the use of the blocker probes in the hybridization reaction greatly reduced the background signals of the assay.

TABLE 28

EFFECT OF BLOCKER PROBES ON HBV DETECTION

| Capture Probe | Blocker probe | Background Signal (RLU) |
|---|---|---|
| HBV C1 | no | 17892 |
| HBV C1 | B1, B2 | 424 |
| HBV C2 | no | 9244 |
| HBV C2 | B3, B4 | 398 |

EXAMPLE 17

Effect of the Length of SSP on TSHC-Plus Detection of HBV

The effect of the length of the DNA sequence inserted into the M13 vector for generating the SSP on TSCH-Plus detection of HBV was studied. A positive control containing 20 pg/ml of HBV plasmid DNA was used. As shown in Table 29, the use of a longer HBV complementary sequence in the SSP (87 base pairs) resulted in a substantial increase in signal of detection. The effect is unlikely due to sub-optimal hybridization temperature condition since the Tm of the shorter probes is 15 degree above the hybridization temperature. As the M13 RNA/DNA duplex formed in the SSP may act to partially block the complementary DNA sequence in the probe from hybridizing to the HBV sequences in the target nucleic acids, longer complementary sequences in the SSP may overcome this block.

TABLE 29

EFFECT OF THE LENGTH OF THE COMPLEMENTARY
SEQUENCE IN THE SSP ON TSHC-PLUS
DETECTION OF HBV

| SSP | Size of the HBV Target DNA Sequence in SSP (bp) | Tm of the HBV Target DNA Sequence in SSP | Hybridization temperature | Signal (RLU) |
|---|---|---|---|---|
| SA1 | 35 | 83° C. | 65° C. | 1741 |
| SA2 | 34 | 80° C. | 65° C. | 1857 |
| SA4 | 87 | 108° C. | 65° C. | 7978 |

EXAMPLE 18

TSHC-Plus and HC II Detection of HBV

The relative sensitivity of TSHC-Plus and HC II (Hybrid Capture II, Digene) detection of HBV was compared. HBV positive standards of three different concentrations were tested in the experiments. As shown in Table 30, the signals obtained using the TSHC-Plus detection method were approximately two-fold higher than those obtained using the HC H detection method.

TABLE 30

TSHC-PLUS AND HC II DETECTION OF HBV*

| | | Target HBV Concentration | | |
|---|---|---|---|---|
| Method | Control | 10 pg/ml | 20 pg/ml | 100 pg/ml |
| HC II | 48 | 2355 | 4225 | 21438 |
| TSHC Plus | 285 | 4856 | 7978 | 37689 |

*Signal measured as relative light unit (RLU)

EXAMPLE 19

Sample Preparation for Target Specific Hybrid Capture Detection of SNPs

An embodiment of the TSHC method for detecting SNPs provides the Hybrid Capture-SNP (HC-SNP) method that is demonstrated herein using p53 DNA as the target molecule and discriminating polymorphisms or SNPs at codon 72 of the p53 coding region (Kawajiri, et al. *Carcinogenesis.* 14:1085-1089, 1993). The two p53 polymorphisms on the anti-sense strand at codon 72, are gCg, which encodes Arginine (Arg), and the p53 codon 72, on the anti-sense strand, gGg, that encodes Proline (Pro). The two polymorphisms are referred to as p53Arg and p53Pro. This is a SNP where the HC-SNP method is used for specific detection of the nucleotide. It is understood that the HC-SNP method is not limited to these specific types of probes, probe labels, and targets, but can also encompass the full scope of variations described for the TSHC method.

Samples comprising either PCR amplicons or genomic DNA were used as a target for polymorphism detection in the HC-SNP embodiment. Using genomic DNA may be particularly beneficial for diagnostic applications. For the preparation of PCR amplicons, two primers were used, for example, the Upper Primer—5'-AAGACCCAGGTCCAGATGAAG-3' (SEQ ID NO:161) and the Lower Primer—5'-AGAATG-CAAGAAGCCCAGAC-3' (SEQ ID NO:162) (described by Klaes et al., *J. Mol. Med.* 77:299-302, 1999). These primers were specifically chosen for amplification of a p53 exon 4 region (182 base pairs), utilizing a program comprising: a) 95° C. for 4 minutes; b) 94° C. for 40 seconds; c) 62° C. for 40 seconds; d) 72° C. for 40 seconds; e) 72° C. for 6 minutes; and f) 4° C. for storage or prior to use, wherein steps b-d are repeated for 25 to 45 cycles depending on the quality of DNA template. PCR amplicons were then diluted to 1:1000 or 1:100 in TE (10 mM Tris; 1 mM EDTA), pH7.4, prior to testing. Non-limiting examples of genomic DNA samples for the preparation of genomic DNA include, but are not limited to, human fluids, cells, tissues, and archival tissues in paraffin blocks. Genomic DNA isolation was performed using the appropriate kits (Qiagen). Approximately, 10-20 µg of isolated genomic DNA per test pair was required for direct polymorphism detecting bypassing the target amplification step.

Each DNA target was tested with p53-Arg specific and p53-Pro specific capture oligos separately. Signal to noise (S/N) ratios were calculated, and the ratio of p53-Arg specific S/N over p53-Pro specific S/N were used to identify the sample genotype. An example of the SNP test results for determining the homozygotes (Arg/Arg or Pro/Pro) versus heterozygotes (Arg/Pro) are shown in Table 31. The results of these tests were confirmed by Wave analysis (Transgenomic; Santa Clara, Calif.) and DNA sequence analysis.

EXAMPLE 20

Target Specific Hybrid Capture Method for Detecting SNPs

Plasmid DNA (p53-Arg and p53-Pro) was prepared from bacterial cultures using Qiaprep Spin Miniprep Kit (Qiagen, Inc.; Valencia, Calif.). Genomic DNA (HeLa, SiHa, and Jurkat) was prepared from the cell lines using DNeasy Tissue Kit (Qiagen, Inc.). Plasmid DNA and clinical sample DNA were amplified using the PCR method previously described (45 cycles). Prior to use, PCR amplified DNA was diluted 1:1000 in TE, pH 7.4, and plasmid DNA samples were diluted to 100 pg/ml in TE, pH 7.4. Five microliters of diluted PCR amplified or plasmid DNA was used per test. Fifty microliters of extracted genomic DNA samples were used per test containing 5 µg, 7 µg, and 10 µg for HeLa, Jurkat, and SiHa, genomic DNA respectively. Each sample was tested twice independently for each assay. The first test was performed using the p53-Arg CSP and p53 SSP. The second test was performed using the p53-Pro CSP and p53 SSP.

A mixture of water and DNA target at a final volume of 50 µl per well, was added to the hybridization microplate. Denaturation Reagent 5100-0431 (Digene) (25 µl) was added per well. The plate was covered with a plate sealer and agitated for 10-30 seconds at 1100 rpm on a plate shaker. The reactions were denatured at 65° C. for 25 minutes in the microplate heater I (Robbins Dcientific Corp.; Sunnyvale, Calif.). During the denaturation step, the probe mixtures were prepared. The p53-Arg specific probe mixture consisted of 15 pmoles/ml of 16-base long Arg-specific CSP, 600 ng/ml of p53 SSP, and 4× Probe Diluent (Digene). The p53-Pro specific probe mixture consisted of 15 pmoles/ml of 16-base long Pro-specific CSP, 600 ng/ml of p53 SSP, and 4× Probe Diluent (Digene). Each probe mixture (25 µl each) was added to the denatured sample. The plate was covered with a plate sealer and agitated for 10-30 seconds at 1100 rpm using a plate shaker. The samples were allowed to hybridize at 65° C. for 1 hour in the microplate heater. Hybridized samples were incubated at room temperature for 5-10 minutes (to decrease the temperature of the plate). Hybridization reactions were transferred to a 96-well streptavidin (SA) plate (Digene), and covered with a plate sealer. The hybrids were captured onto the SA plate at 45° C. for 45 minutes with agitation at 900 rpm. Immobilization of CSP hybridized targets can be performed in hybridization solution placed into wells of a 96-well plate, for example, and the plate is shaken for 15 minutes to 2 hours at temperatures ranging from 20° C. to 90° C., preferably at room temperature for 1 hour shaking at 1100 rms. Capture temperatures above room temperature may be preferred for added levels of stringency as hybridization (and "promiscuous hybridization") does occur during the plate capture step. Supernatant was decanted and 100 μl per well of DR-1 (Digene) was added for detection of captured RNA/DNA hybrids. The plate was incubated at room temperature for 30 minutes without agitation. Supernatant was discarded and the plate was washed twice with room temperature Sharp Wash Buffer. The wells were then re-filled with Sharp Wash Buffer and the plate was incubated at 60° C. for 10 minutes. The plate was then washed twice with room temperature Sharp Wash Buffer, and once with room temperature Hybrid Capture 2 Wash Buffer. The plate was blotted from residual wash buffer (using kimtowels). A chemiluminescent phosphorylated substrate, DR-2 (100 W well) was added and reactions were incubated at room temperature for 15 minutes without agitation. The activated substrate was measured and analyzed using a plate luminometer (See Table 31).

TABLE 31

GENOTYPE DATA FROM HC-SNP

| P53 DNA TARGET | S/N using Arg-specific capture oligo | S/N using Pro-specific capture oligo | Arg/Pro Ratio | Genotype |
| --- | --- | --- | --- | --- |
| P53-Arg DNA, 100 pg/ml | 98.9 | 4.5 | 21.91 | Arg homozygous |
| P53-Pro DNA, 100 pg/ml | 10.2 | 68.0 | 0.15 | Pro homozygous |
| P53-Arg/Pro DNA, 100 pg/ml | 56.4 | 54.1 | 1.04 | Arg/Pro heterozygous |
| P53-Arg PCR | 1350.1 | 7.9 | 170.90 | Arg homozygous |
| P53-Pro PCR | 88.0 | 1093.8 | 0.08 | Pro homozygous |
| P53-Arg/Pro PCR | 874.3 | 506.5 | 1.73 | Arg/Pro heterozygous |
| HeLa DNA, 5 μg per well | 10.8 | 7.0 | 1.54 | Arg/Pro heterozygous |
| SiHa DNA, 10 μg per well | 3.8 | 15.5 | 0.25 | Pro homozygous |
| Jurkat DNA, 7 μg per well | 23.2 | 1.6 | 14.5 | Arg homozygous |
| PCR Clinical Sample 1 | 162.6 | 106.2 | 1.53 | Arg/Pro heterozygous |
| PCR Clinical Sample 2 | 51.9 | 652.5 | 0.08 | Pro homozygous |
| PCR Clinical Sample 3 | 345.3 | 2.3 | 150.13 | Arg homozygous |

The above description of various preferred embodiments has been presented for purposes of illustration and description. It is not intended to be exhaustive or limiting to the precise forms disclosed. Obvious modifications or variations are possible in light of the above teachings. The embodiments discussed were chosen and described to provide illustrations and its practical application to thereby enable one of ordinary skill in the art to utilize the various embodiments and with various modifications as are suited to the particular use contemplated. All such modifications and variations are within the system as determined by the appended claims when interpreted in accordance with the breadth to which they are fairly, legally and equitably entitled.

We claim:

1. A method of detecting a target nucleic acid consisting essentially of:
   a) hybridizing a single-stranded or partially single-stranded target nucleic acid to a capture sequence probe and a signal sequence probe, wherein the capture sequence probe and the signal sequence probe hybridize to non-overlapping regions within the target nucleic acid and not to each other, wherein said hybridization forms an RNA/DNA hybrid between said signal sequence probe and the target nucleic acid; and
   b) adding a blocker probe to the hybridization reaction, wherein said blocker probe hybridizes to excess non-hybridized capture sequence probes; and
   c) detecting the RNA/DNA hybrid by binding an antibody that recognizes the RNA/DNA hybrid to said hybrid, wherein said antibody is detectably labeled.

2. The method of claim 1, further consisting essentially of binding the hybrid formed in step a) to a solid phase to form a bound hybrid.

3. The method of claim 1, wherein the signal sequence probe is single-stranded.

4. The method of claim 1, wherein the capture sequence probe is modified with at least one ligand.

5. The method of claim 4, wherein the capture sequence probe is biotinylated.

6. The method of claim 5, wherein the capture sequence probe is linear having a 5' and a 3' end, wherein both the 5' and the 3' ends are biotinylated.

7. The method of claim 1, wherein the capture sequence probe and the signal sequence probe hybridize to regions of the target nucleic acid, wherein the regions are less than 3 kilobases apart.

8. The method of claim 1, wherein the capture sequence probe and the signal sequence probe hybridize to regions of the target nucleic acid, wherein the regions are less than 500 bases apart.

9. The method of claim 1, further consisting essentially of the step of forming single-stranded target nucleic acid prior to the hybridization step.

10. The method of claim 1, wherein hybridizations of the capture sequence probe and the signal sequence probe to the target nucleic acid are performed sequentially.

11. The method of claim 1, wherein the hybrid formed in step a) is bound onto a solid phase forming a bound hybrid.

12. The method of claim 11, wherein the bound hybrid is formed at room temperature.

13. The method of claim 11, wherein the solid phase is coated with streptavidin.

14. The method of claim 11, wherein the solid phase is a microplate.

15. The method of claim 1, wherein the antibody is labeled with alkaline-phosphatase.

16. The method of claim 1, wherein the blocker probes are added to the hybridization reaction following the hybridization of the capture sequence probes to the target nucleic acid.

17. The method of claim 1, wherein the blocker probe has a lower melting temperature than that of the capture sequence probe.

18. A method of detecting a target nucleic acid consisting essentially of:
   a) hybridizing a single stranded or partially single-stranded target nucleic acid to a capture sequence probe and a signal sequence probe, wherein the capture sequence probe and the signal sequence probe hybridize to non-overlapping regions within the target nucleic acid and not to each other, wherein the signal sequence probe comprises a DNA/RNA hybrid region, wherein said hybridization forms a complex; and
   b) adding a blocker probe after the hybridization reaction, wherein said blocker probe hybridizes to excess non-hybridized capture sequence probes; and
   c) detecting said complex.

19. The method of claim 18 wherein the signal sequence probe comprises a sequence at least 40 bases in length.

20. The method of claim 18 wherein the capture sequence probe comprises a sequence at least 6 bases in length.

21. The method of claim 20 wherein the capture sequence probe is immobilized on a solid phase.

22. The method of claim 18 wherein said complex is detected by binding an antibody that recognizes the DNA/RNA hybrid region to said region, wherein the antibody is detectably labeled.

23. The method of claim 18 wherein the capture sequence is modified with at least one ligand.

24. The method of claim 23 wherein the ligand is biotin.

25. The method of claim 24, wherein the capture sequence probe is linear having a 5' and 3' end, wherein both the 5' and 3' ends are biotinylated.

26. The method of claim 18, wherein the blocker probes comprise a length of 4-10 base pairs shorter than the length of the capture sequence probe.

27. The method of claim 1, wherein said probes comprise a nucleic acid probe consisting of a sequence selected from the group consisting of SEQ ID NO: 1 through SEQ ID NO: 160.

28. A method of detecting a target nucleic acid comprising:
   a) hybridizing a single-stranded or partially single-stranded target nucleic acid to a capture sequence probe and a signal sequence probe to form double-stranded hybrids between said probes and the target nucleic acid; and
   b) adding a blocker probe to the hybridization reaction, wherein said blocker probe hybridizes to excess non-hybridized capture sequence probes; and
   c) binding the hybrid to a solid phase forming a bound hybrid; and
   d) detecting the bound hybrid, wherein the capture sequence probe and the signal sequence probe hybridize to non-overlapping regions within the target nucleic acid and not to each other,
wherein step c) is carried out at about 20° C. to about 90° C.

29. The method of claim 28, wherein hybridization of the capture sequence probe and the signal sequence probe to the target nucleic acid are performed sequentially.

30. The method of claim 28, wherein step a) and step c) are performed sequentially.

31. The method of claim 28, wherein the signal sequence probe is single-stranded.

32. The method of claim 28, wherein the capture sequence probe is modified with at least one ligand.

33. The method of claim 28, wherein the ligand is biotin.

34. The method of claim 33, wherein the capture sequence probe is linear having a 5' and 3' end, wherein both the 5' and the 3' ends are biotinylated.

35. The method of claim 28, wherein the capture sequence probe and the signal sequence probe hybridize to regions of the target nucleic acid, wherein the regions are less than 3 kilobases apart.

36. The method of claim 28, wherein the capture sequence probe and the signal sequence probe hybridize to regions of the target nucleic acid, wherein the regions are less than 500 bases apart.

37. The method of claim 28, wherein the capture sequence probe is a fusion of two or more sequences complementary to different regions of the target nucleic acid or to different target molecules.

38. The method of claim 28, wherein the double-stranded hybrid formed is a DNA/RNA hybrid.

39. The method of claim 28, further comprising the step of forming single-stranded DNA prior to the hybridization step.

40. The method of claim 28, wherein hybridization of the capture sequence probe and the signal sequence probe to the target nucleic acid are performed simultaneously.

41. The method of claim 28, wherein step a) and step c) are performed simultaneously.

42. The method of claim 29, wherein the blocker probe has lower melting temperature than that of the capture sequence probe.

43. The method of claim 29, wherein the solid phase is coated with streptavidin.

44. The method of claim 29, wherein the solid phase is a microplate.

45. The method of claim 28, wherein the capture sequence probe comprises at least 6 bases in length.

46. The method of claim 28, wherein the bound hybrid is detected using an antibody that recognizes a hybrid.

47. The method of claim 46, wherein the hybrid is a DNA/RNA-hybrid.

48. The method of claim 46, wherein the antibody that recognizes a DNA/RNA hybrid is labeled with alkaline-phosphatase.

49. The method according to claim 28, wherein the signal sequence probe comprises a deleted capture sequence probe region and is complementary to the target nucleic acid.

50. The method according to claim 28, wherein the target nucleic acid is a single nucleotide polymorphism.

51. The method according to claim 50, wherein the specificity of binding the hybrid to a solid phase is modulated by temperatures of greater than room temperature.

52. The method according to claim 50, wherein the specificity of binding the hybrid to a solid phase is modulated by the addition of blocker probes.

53. The method according to claim 50, wherein the specificity of binding the hybrid to a solid phase is modulated by temperatures of greater than room temperature and the addition of blocker probes.

54. The method of claim 1 wherein the target nucleic acid is a deoxyribonucleic acid.

55. The method of claim 18 wherein the target nucleic acid is a deoxyribonucleic acid.

56. The method of claim 28 wherein the target nucleic acid is a deoxyribonucleic acid.

57. The method of claim 2 wherein the step of forming a bound hybrid is carried out at about 20° C. to about 90° C.

58. The method of claim 1, wherein the signal sequence probe comprises
a sequence capable of hybridizing to the 5' side of a target sequence to which a capture sequence probe is capable of hybridizing and
a sequence capable of hybridizing to the 3' side of a target sequence to which a capture sequence probe is capable of hybridizing.

59. The method of claim 18, wherein the signal sequence probe comprises
a sequence capable of hybridizing to the 5' side of a target sequence to which a capture sequence probe is capable of hybridizing and
a sequence capable of hybridizing to the 3' side of a target sequence to which a capture sequence probe is capable of hybridizing.

60. The method of claim 28, wherein the signal sequence probe comprises
a sequence capable of hybridizing to the 5' side of a target sequence to which a capture sequence probe is capable of hybridizing and
a sequence capable of hybridizing to the 3' side of a target sequence to which a capture sequence probe is capable of hybridizing.

* * * * *